US011739351B2

(12) United States Patent
Mermod et al.

(10) Patent No.: US 11,739,351 B2
(45) Date of Patent: Aug. 29, 2023

(54) EUKARYOTIC CELLS FOR PROTEIN MANUFACTURING AND METHODS OF MAKING THEM

(71) Applicant: SELEXIS S.A., Plan les Ouates (CH)

(72) Inventors: Nicolas Mermod, Plan-les-Ouates (CH); Pierre-Olivier Duroy, Plan-les-Ouates (CH); Sandra Bosshard, Plan-les-Ouates (CH); Philippe Le Mercier, Plan-les-Ouates (CH)

(73) Assignee: SELEXIS S.A., Plan les Ouates (CH)

( * ) Notice: Subject to any disclaimer, the term of this patent is extended or adjusted under 35 U.S.C. 154(b) by 1148 days.

(21) Appl. No.: 16/065,167

(22) PCT Filed: Dec. 23, 2016

(86) PCT No.: PCT/EP2016/082567
§ 371 (c)(1),
(2) Date: Jun. 22, 2018

(87) PCT Pub. No.: WO2017/109177
PCT Pub. Date: Jun. 29, 2017

(65) Prior Publication Data

US 2019/0194694 A1 Jun. 27, 2019

Related U.S. Application Data

(60) Provisional application No. 62/387,375, filed on Dec. 24, 2015.

(51) Int. Cl.

| | |
|---|---|
| ***C12N 15/90*** | (2006.01) |
| ***C12N 15/10*** | (2006.01) |
| ***C07K 14/005*** | (2006.01) |
| ***C12N 5/071*** | (2010.01) |
| ***C12N 15/861*** | (2006.01) |
| ***C12N 15/113*** | (2010.01) |
| ***C12P 21/00*** | (2006.01) |

(52) U.S. Cl.
CPC ......... *C12N 15/907* (2013.01); *C12N 5/0682* (2013.01); *C12N 15/102* (2013.01); *C12N 15/113* (2013.01); *C12N 15/861* (2013.01); *C12P 21/00* (2013.01); *C12N 2310/20* (2017.05); *C12N 2510/00* (2013.01); *C12N 2511/00* (2013.01)

(58) Field of Classification Search
CPC ............................... C12N 5/0682; C12P 21/00
See application file for complete search history.

(56) References Cited

U.S. PATENT DOCUMENTS 10,959,413 B2 3/2021 Church et al.
2003/0053991 A1* 3/2003 Kingsman ........ C07K 14/70567 424/93.2
2006/0115875 A1* 6/2006 Hu ........................ C12Q 1/708 435/69.1
2012/0231449 A1 9/2012 Mermod et al.
2015/0361451 A1 12/2015 Fourn et al.

OTHER PUBLICATIONS

Mager et al., ASMscience/MicrobiolSpectrum, 1-20, Feb. 2015.*
A.J. Shepherd et al, "Characterization of Endogenous Retrovirus in Rodent Cell Lines Used for Production of Biologies", Biologicals, vol. 31, No. 4, Dec. 1, 2003 (Dec. 1, 2003), pp. 251-260.
Carlotta Ronda et al, "Accelerating Genome Editing in CHO Cells Using CRISPR Cas9 and CRISPy, a Web Based Target Finding Tool", Biotechnolgy and Bioengineering, vol. 111, No. 8, Aug. 22, 2014 (Aug. 22, 2014), pp. 1604-1616.
Hsu Patrick D et al, "Development and Applications of CRISPR-Cas9 for Genome Engineering", Cell, vol. 157, No. 6, Jun. 5, 2014 (Jun. 5, 2014), pp. 1262-1278.
J.W. Bruce et al, "Isolation of Cell Lines That Show Novel, Murine Leukemia Virus-Specific Blocks to Early Steps of Retroviral Replication", Journal of Virology, vol. 79, No. 20, Oct. 15, 2005 (Oct. 15, 2005), pp. 12969-12978.
Jae Seong et al, "CRISPR/Cas9 -Mediated Genome Engineering of CHO Cell Factories: Application and Perspectives", Bioechnology Journal, vol. 10, No. 7, Jun. 2015 (Jun. 7, 2015), pp. 979-994.
Jordan Pinder et al, "Nuclear Domain 'Knock-in' Screen for the evaluation and Identification of Small Molecule Enhancers of CRISPR-Base Genome Editing", vol. 43, No. 19, Oct. 1, 2015 (Oct. 1, 2015), pp. 9379-9392.
L. Yang et al, "Genome -wide Inactivation of Porcine Endogenous Retroviruses (PERVs)", Science, vol. 350, No. 3264, Nov. 27, 2015 (Nov. 27, 2015), pp. 1101-1104.
Van Trung Chu et al, "Increasing the Efficiency of Homology-Directed Repair for CRISPR-Cas9-Induced Precise Gene Editing in mammalian cells" Nature Biotechnology, vol. 33, No. 5, Mar. 24, 2015 (Mar. 24, 2015), pp. 543-548.
Chinese Patent Office: Search report issued in Chinese parallel application 2016-80075813.4 citing previously cited references and reference cited in this IDS, citations are provided in English as well as indication of relevance (Y, A) (dated Nov. 29, 2021).
Japanese Patent Office: Office Action in parallel Japanese Application 2018-531448 including English translation provided by Japanese associate (dated Aug. 31, 2021).
Lie et al., Chinese hamster ovary cells contain transcriptionally active full-length type C proviruses, Journal of Virology 68(12):7840-9 (Dec. 1994).
De Marco et al., Conserved and Variable Features of Gag Structure and Arrangement in Immature Retrovirus Particles, Journal of Virology, vol. 84, No. 22, p. 11729-11736 (Nov. 2010).
L. Bent et al., ERV-L Elements: a Family of Endogenous Retrovirus-Like Elements Active throughout the Evolution of Mammals, Journal of Virology, vol. 73, No. 4, p. 3301-3308 (Apr. 1999).
R.A. Weiss, On the concept and elucidation of endogenous retroviruses, Phil Trans R Society, B 368: 20120494 (2013).

(Continued)

*Primary Examiner* — Maryam Monshipouri
(74) *Attorney, Agent, or Firm* — AGRIS & VON NATZMER, LLP; Joyce Von Natzmer

(57) ABSTRACT

Disclosed are mammalian cells and mammalian cell lines that have a reduced load of remnants of past viral/retroviral infections and methods of producing and using the same.

10 Claims, 26 Drawing Sheets

Specification includes a Sequence Listing.

(56) References Cited

OTHER PUBLICATIONS

Russian Agency for Patents and Trademarks, Englisch machine translation of examination report for the Russian counterpart application 2018118204/10(028402) based on PCT/EP2016/082567 citing Rymar et al. (Nov. 6, 2020).

Rymar S.E., Encapsulated Genetically Modified Cells of CHO-K1 as Source of Human Recombinant FGF2, Factories of experimental evolutionary organisms, No. 13, pp. 326-330 (2013) (Ukrainian language document, English abstract provided, Рымарь, С.Е. Инкапсулированные генетически иодифицированные клетки СНО-К1 как источник рекомбинантного FGF2 человека Фактори експериментальної еволюції організмів Зб. наук. пр. Бібліогр 12 назв. — рос.) .

* cited by examiner

Endogenous Retroviruses (ERV)

Motif

| Feature key | Position(s) | Length | Description | Graphical view | Feature identifier | Actions |
|---|---|---|---|---|---|---|
| Motif[i] | 111 – 114 | 4 | PTAP/PSAP motif | | | |
| Motif[i] | 130 – 134 | 5 | LYPX(n)L motif | | | |
| Motif[i] | 162 – 165 | 4 | PPXY motif | | | |

HMM logo

| | | |
|---|---|---|
| P03332 | GAG_MLVMS | 155 |
| Q27ID9 | GAG_XMRV6 | 154 |
| P03336 | GAG_MLVAV | 154 |
| P03341 | GAG_BAEVM | 152 |
| P27460 | GAG_MLVCB | 153 |
| P23090 | GAG_MLVDU | 151 |
| P10262 | GAG_FLV | 224 |
| P03340 | GAG_FSVMD | 227 |
| P26807 | GAG_MLVF5 | 156 |
| P26806 | GAG_MLVFF | 155 |
| P26805 | GAG_MLVFP | 155 |
| P21416 | GAG_GALV | 132 |
| P21435 | GAG_MLVHO | 153 |
| Q9TTC2 | GAG_KORV | 135 |
| P03334 | GAG_MSVMO | 155 |
| P32594 | GAG_MSVMT | 155 |
| P29167 | GAG_MLVBM | 154 |
| P29168 | GAG_MLVDE | 154 |
| P11269 | GAG_MLVRD | 154 |
| P03330 | GAG_WMSV | 135 |
| Q2F7J2 | GAG_XMRV3 | 154 |
| Q2F7I9 | GAG_XMRV4 | 154 |

Search for Murine retrovirus type C sequences

Consensus
Original viral seq.

Seq. from CH
Seq. from CHO-K1

Work on the sequences

- Manual alignment
- Annotation
- Design of primers
- Search for corresponding sequences
- Search in the bordering sequences for genes, specific integration markers, expression, etc Regulation of ERV in CHO cells

Nucleases facilitated gene targeting: CRISP/Cas9 system

Increased expression of rate-limiting HR and/or MMEJ factors stimulates gene correction in a dose-dependent manner Alignment of GAG RNAs from selection of CHO Gammaretrovirus-like ERV. The marks under the alignments represent mutations.

Experimental set-up for ERV inactivation

1. Do sgRNAs cleave ERV sequences efficiently?

2. Increasing knockouts by blocking HR using Rad51 siRNAs

-> mRNA (i.e. cDNA) assays by endpoint PCR

-> mRNA (i.e. cDNA) reading frame assays by sequencing

EUKARYOTIC CELLS FOR PROTEIN MANUFACTURING AND METHODS OF MAKING THEM

CROSS-REFERENCE TO RELATED APPLICATIONS

This is the U.S. national stage of international application no. PCT/EP2016/082567, filed Dec. 23, 2016 designating the United States and claiming the benefit of U.S. provisional application No. 62/387,375, filed Dec. 24, 2015, which is incorporated herein by reference in its entity.

INCORPORATION OF SEQUENCE LISTING

The sequence listing text file submitted on Nov. 20, 2018 (file name "3024-232NS-seq-11-19-18-1 ST25.txt"; size 108924 bytes; date of creation Nov. 20, 2018) is incorporated herein by reference.

BACKGROUND

Many stable, high yield mammalian cell lines used in recombinant protein manufacturing of therapeutic drugs are currently available. Processes have been optimized and improved so that cell line development could be reduced from 8 to 12 months to 4 months, while, at the same time, improving the yield and stability of protein-producing mammalian cell lines.

However, there remains a need to provide mammalian cell lines that have better safety profiles.

In particular, there is a general need to devise more efficient procedures for analyzing and documenting recombinant protein-producing mammalian cell lines, thus increasing throughput, speed and efficacy of candidate drug development, and decreasing the costs of regulatory validation as well as the risks of unforeseen and undesirable effects on protein therapeutics. Furthermore, the perils of production site closure due to undetected cell line contaminants (e.g. mycoplasma or adventitious viral agents) would be reduced by implementing a more efficient cell characterization process within the operating procedures.

All characterized mammalian cell lines and organisms contain remnants of past viral, including retroviral, infections, resulting in viral genes being integrated into the cell genome. These viral remnants are often crippled and mutated, but some of them nevertheless remain expressed and lead to the generation of viral-like particles that can be detected using e.g. electron microscopy.

CHO cells are most widely used, as they can be stable hosts for the expression of heterologous genes, have a long history of safety, produce proteins that bear human-like post-translational modification, and are relatively simple to adapt to adherence-independent and rapid growth in serum-free synthetic media in bioreactors. Nevertheless, the development and documentation of highly efficient clonal cell lines for cultures in bioreactors is often slow and labor-intensive, still suffering from a series of bottlenecks and low protein yield.

CHO cells are considered safe for therapeutic protein production relative to other cell lines. Nevertheless, they also contain remnants of infectious viral particles that require regulatory documentation, as these remnants lead to the release of viral particles by CHO cells (Lie, Y. S. et al., 1994). Furthermore, integrated proviral genomes may potentially recombine, mutate and thereby change properties, albeit at a low frequency.

CHO cells whose genome is depleted of expressed viral remnants, and thereby provide a safer mammalian cell host for therapeutic protein production, are highly desirable.

The recent development of high-throughput DNA sequencing (Next-Generation DNA Sequencing or NGS) based techniques to characterize the genome of cells used to produce proteins (e.g. CHO cells) has led to the successful characterization of transgene integrations sites (Kostyrko et al, 2016).

The publications and other materials, including patents and patent applications, used herein to illustrate the invention and, in particular, to provide additional details respecting the practice are incorporated by reference. For convenience, the publications are referenced in the following text by author and date and are listed alphabetically by author in the appended bibliography.

Given the continued detection of adventitious agents within cells used at therapeutic production sites, pressure is mounting from regulatory agencies such as the FDA to use production cell lines that are better characterized genetically. The FDA defines adventitious agents and includes retroviruses integrated into the genome of a cell (see the FDA's Guidance for Industry Characterization and Qualification of Cell Substrates and Other Biological Materials Used in the Production of Viral Vaccines for Infectious Disease Indications, February 2010). However, currently the analytical and bio-informatics tools required for the complete assembly of the genome of the various CHO cell sublines and for the analysis and interpretation of the genome sequences are often lacking.

SUMMARY OF THE INVENTION

Figure 1:
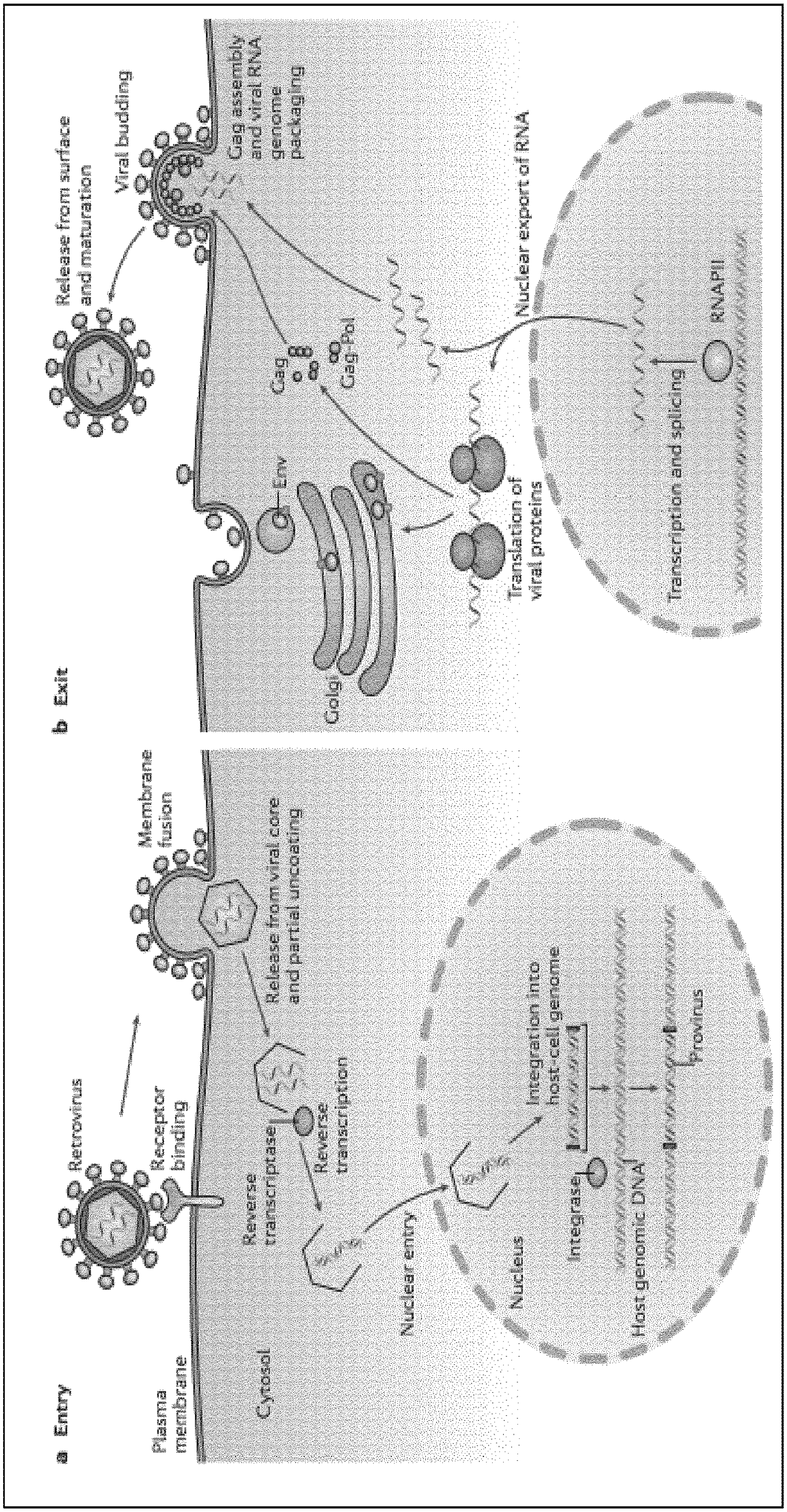
FIGS. 1*a* and 1*b* show the genesis of an endogenous retrovirus (ERV) (a) and its exit after dormant existence within the host genome (b). A multiplication of the retrovirus requires integration of genes encoding reverse transcriptase and other components of the virus cycle. ERVs are almost exclusively found in the animal kingdom.

The present invention is, in one embodiment, directed at an engineered cell, preferably of a mammalian cell line such as an engineered CHO cell, including an engineered CHO-K1 such as a CHO-M cell, comprising:

a genome of the cell, wherein the genome comprises one or more alterations comprising:
- deletions,
- additions/integrations, and/or
- substitutions, of one or more nucleic acids in one or more, generally, more than 10, 20, 30, 40, 50, 60, 80, 90 or 100 endogenous retrovirus (ERV) elements which are part of said genome.

The ERV elements may be from gamma retroviral ERVs, including Koala epidemic viral (KoRV), Mouse Mammary Tumor Viral (MMTV), Mouse Leukemia Viral (MLV) ERVs. The one or more alterations may preferably suppress or eliminate release of or be adapted to suppress or eliminate one or more, preferably more than 60%, 70%, 80%, 90%, 95% or 100% of said ERVs.

The one or more altered (ERV) elements may be or may be from a gag, pol and/or env gene, preferably from the gag gene, encoding, a MA (matrix), CA (capsid), NC (nucleocapsid), a further domain encoding proteins such as pp12 or p6 and/or may be long terminal repeats (LTRs) of a ERV.

The one or more ERV elements may in particular encode a Gag (groups antigen) protein, a Pol (reverse transcriptase) protein and/or an Env (envelope) protein.

The additions/insertions, deletions or substitutions may comprise more than 2, 3, 4, 5, 10, 15, 20, 25, 30, 40, 45, 50, 55, 60, 65, 70, 75, 80, 85, 90, 95, 100, 150 or 200 nucleic acids.

The alterations may be targeted to the one or more (ERV) elements, which may be or may be from one or more gag, pol and/or env genes, preferably gag genes, and sequences of the gene may be subjected to the targeted integrations of, e.g., a transgene encoding a marker protein such as GFP (green fluorescent protein), or to amino-acid substitutions leading to a dominant-negative phenotype.

The ERV elements may are from a gag gene and at least 1, 2, 3, 4, 5, 6, 7, 8, 9, 10 or more or 10%, 20%, 30%, 40%, 50%, 60%, 70%, 80%, 90%, 95%, 98%, 99% or all of the elements may comprise said alterations.

The alterations may be in consensus sequences of the EVR elements, and the consensus sequence may be at least 5, 10, 15, 20, 25, 30, 35, 40, 45, 50 base pairs long, preferably between 15 and 25 or between 30 and 50 base pairs long (compare FIG. 21B).

The engineered cell may release no or substantially no ERVs.

The cell may also comprise heterologous nucleic acid sequences encoding, inhibiting or activating one or more proteins of a recombination pathway, and/or heterologous nucleic acid sequences encoding one or more sequences or proteins suppressing expression of the one or more proteins of a recombination pathway, preferably Nbs1, Mre11, Rad51, Ligase 1 and/or Ligase 3.

The heterologous nucleic acid sequences may be present as a vector/expressed by a vector that is preferably not integrated into the genome of the cell.

The engineered cell may also further comprise heterologous donor DNA, preferably on a vector, encoding one or more marker proteins such as GFP (green fluorescent protein).

The engineered cell may further comprise a transgene. The transgene may be a marker gene encoding a marker protein such as GFP and/or a biotherapeutic which may preferably be expressed from a vector integrated into the genome.

The one or more alterations may be or comprise the substitution of one or more myristoylated amino acids within a myristoylation motif in one or more of the ERV elements, such as a gag gene or an ERV element being from the gag gene, with a non-myristoylated amino acid.

Figure 12A:
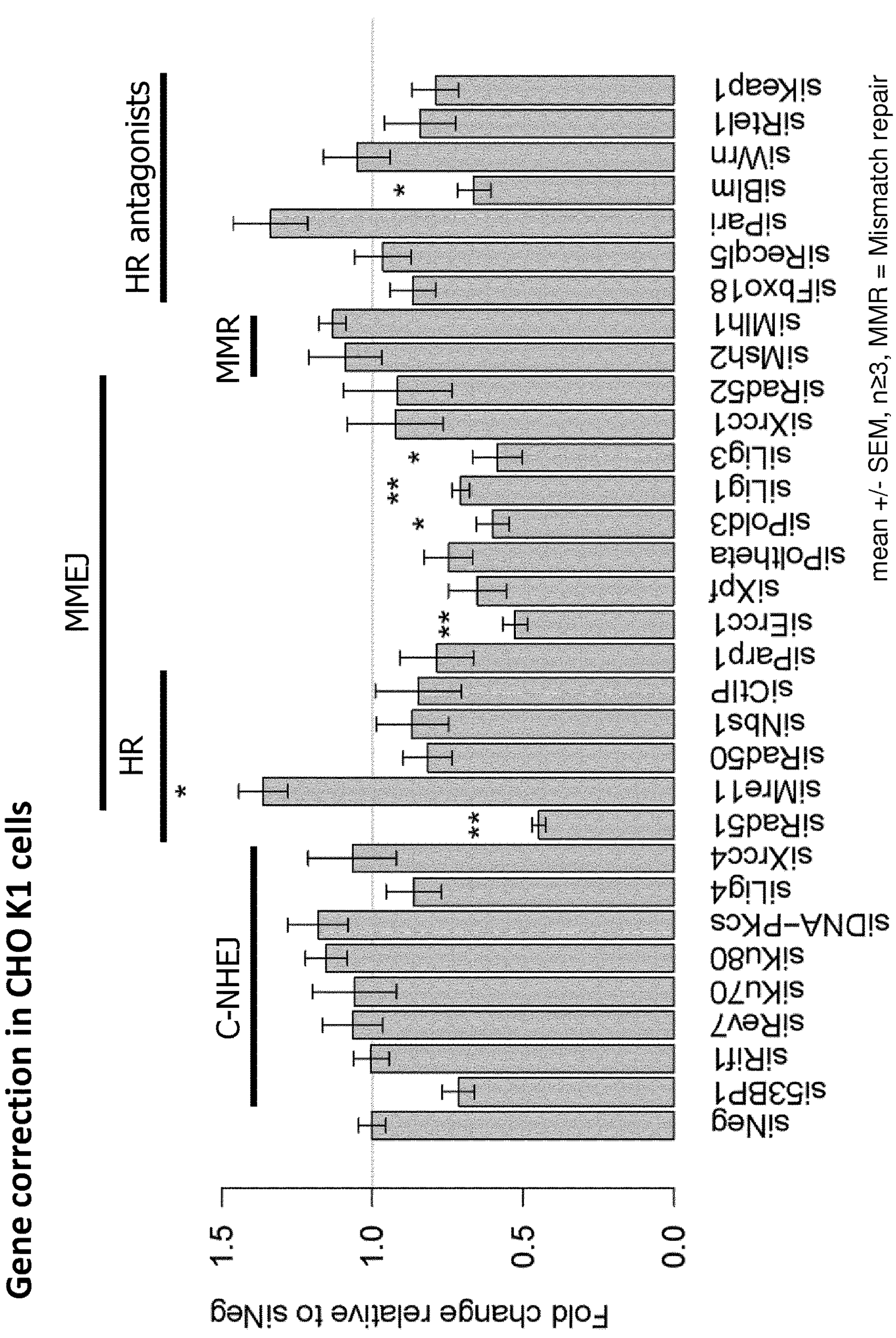
FIG. 12A shows the increase or decrease of gene correction from FIG. 10 (CHO-K1 cells) depending on silencing (via siRNAs) of genes influencing different repair pathways. Silencing of genes in HR (homologous repair) partially reduces the % of correction (Rad 51 silencing/knockdown) and partially increases it (Mre11 silencing/knockdown). (The x axis shows the different silencing RNAs used organized according to repair pathway, * indicate significant differences).

For this purpose, the cell is modified to increase HR/MMEJ expression (see FIGS. 12A and 12B), by providing/expressing in said cell at least transiently sequences, such as in form of a transiently expressed vector encoding HR and/or MMEJ proteins such as Pad51, Lig3, Ercc1, Pold3; and/or sequences, such as siRNA sequences, such as siMRe11 or vectors encoding the same.

The ERV element(s) such as a gag gene or an ERV element being from the gag gene, may comprise a PPYP motif and (i) sequences encoding the PPYP motif and/or sequences of up to 20 or 30 nucleic acids flanking the sequences in (i) may comprise the alternation.

The engineered cell may be a CHO cell and may have one or more deletions, additions, and/or substitutions in one or more SEQ IDs 1, 2, 3, 4 or sequences having more than 90% or 95% sequence identity therewith, preferably within the ERV elements of said sequences.

The engineered cell may be a CHO cell and may have one or more deletions, additions, and/or substitutions in ERV group 1 consensus sequence, such as SEQ ID NO. 30 or in sequences having more than 90% sequence identify therewith and wherein the sequences with the deletions, additions, and/or substitution no longer encode a functional Gag protein.

The present invention is also directed to a method for improved genome editing comprising:

(i) providing or introducing a non-naturally occurring/heterologous system for creating single or double stranded brakes in a target nucleic acid sequence of a cell, preferably a cell of interest, such as a consensus sequence of a ERV element, preferably a ERV element that is or is from a gag gene, and further (ii) providing or introducing into the cell (a) heterologous nucleic acid sequences encoding or activating one or more proteins of one or more of the recombination pathways, and/or (b) heterologous sequences encoding one or more sequences, such as siRNAs or proteins, suppressing/decreasing the expression of the one or more proteins of one or more of the recombination pathways, wherein said heterologous system of (i) and/or sequences of (ii) (a) and/or (ii) (b) are preferably transiently expressed in the cell of interest.

The heterologous sequences may encode, activate or inactivate one or more proteins of a recombination pathway, in particular one or more proteins of Homologous Recombination (HR), pathway, in particular Rad51, Nbs1, Mre11, Ligase 1 and/or Ligase 3.

A marker gene, such as GFP, may be inserted into the target nucleic acid sequence via homologous recombination. Cells comprising the marker gene may be preferably selected.

The heterologous sequences of (a) above, may encode, activate or inactivate proteins of the MNR complex, such as Nbs1 and/or Mre 11, and/or said heterologous sequences of (b) may encode sequences or proteins suppressing expression of one or more proteins of Homologous Recombination (HR) pathway such as Rad51, Nbs1, Mre11, Ligase 1 and/or Ligase 3.

A deletion or insertion may be introduced into the one or more ERV elements via non-homologous end-joining (NHEJ) or microhomology mediated end joining (MMEJ).

The heterologous sequences may be part of- or expressed from integrating or preferably non-integrating vectors.

The non-naturally occurring/heterologous system for introducing single or double stranded brakes into a target nucleic acid sequence may be a CRISPR/Cas9 system or may be based thereon.

One or more myristoylated amino acids within a myristoylation motif in one or more of the ERV elements may be substituted with a non-myristoylated amino acid.

Sequences encoding a PPYP motif and/or sequences of up to 10, 20 or 30 nucleic acids flanking the motif may comprise an alteration.

Sequences suppressing expression of, e.g., HR proteins such as Rad51 may be only transiently expressed in the cells.

The invention is also directed an engineered cell preferably a mammalian cell such as an engineered CHO cell, including a CHO-K1 cell, which preferably does not release viral particles/releases substantially no viral particles, especially under standard and/or stressing culturing condition, and wherein a genome of the cell of comprises one or more alterations comprising:

(a) deletions, (b) additions/integrations, and/or (c) substitutions, of one or more nucleic acids in one or more, generally, more than 10, 20, 30, 40, 50, 60, 80, 90 or 100 endogenous retrovirus (ERV) elements, and is preferably produced by any one of the methods of set forth herein.

The present invention is also directed to a kit comprising:

(i) in one container at least one non-integrating vector encoding at least a nuclease, such as CRISPR, (ii) in the same or a further container one or more guide RNAs or sequences encoding the one or more guide RNAs targeting a motif in a ERV element (iii) in same or a further container one or more siRNAs or sequences encoding one or more siRNAs, and in a further container instruction of how to provide (i), (ii) and (iii) within a cell.

The sequences encoding the one or more guide RNAs targeting the motif in the ERV element and/or the sequences encoding one or more siRNAs may be part of a vector. Any of the vectors described herein may be only transiently expressed and/or may be a non-integrating vector of (i). The ERV element may encode a Gag protein. The motif may be a myristoylation motif or a PPXY motif, in particular a PPYP motif. The siRNA(s) may be directed against a gene of the HR pathway.

DESCRIPTION OF VARIOUS AND PREFERRED EMBODIMENTS OF THE INVENTION

A cell, preferably a mammalian cell/eukaryotic cell, that according to the present invention is engineered to produce an engineered cell is capable of being maintained under cell culture conditions. Standard cell culture conditions are from 30 to 40° C., preferably at or at about 37° C., for instance in fully synthetic culture medium as used in the production of recombinant proteins. Non-limiting examples of this type of cell are non-primate eukaryotic cells such as Chinese hamster ovary (CHOs) cells including the CHO-K1 (ATCC CCL 61) cells and SURE CHO-M cells (derivative of CHO-K1), and baby hamster kidney cells (BHK, ATCC CCL 10). Primate eukaryotic host cells include, e.g., human cervical carcinoma cells (HELA, ATCC CCL 2) and 293 [ATCC CRL 1573] as well as 3T3 [ATCC CCL 163] and monkey kidney CV1 line [ATCC CCL 70], also transformed with SV40 (COS-7, ATCC CRL-1587). The term engineered signifies a cell that has been altered, e.g., by transfection with, e.g., a transgenic sequence and/or by mutation. As the person skilled in the art will readily understand these cells are, even prior to engineering as described herein, non-naturally occurring cells. The above-mentioned cells, in particular, the various CHO cells, are commonly used in biotechnological applications, such as for the production of therapeutic proteins, and are herein referred to as cells of interest. As the person skilled in the art will readily understand, other cells than the ones mentioned above might be cells of interest as long as they are used in biotechnological applications, in particular for the expression of, e.g., therapeutic proteins.

The three major proteins encoded within the retroviral genome are Gag, Pol, and Env. Gag (Group Antigens) encoded by the gag gene is a polyprotein, which is processed to matrix and other core proteins, including the nucleoprotein core particle, that determine the retroviral core. Pol is the reverse transcriptase, encoded by the pol gene and has RNase H and integrase function. Its activity results in the double-stranded DNA pre-integrated form of the virus and, via the integrase function, for the integration into the host genome, and also via the RNase function, the reverse transcription after integration into the genome of the host. Env is the envelope protein, encoded by the env gene, and resides in the lipid layer of the virus determining the viral tropism.

Endogenous retroviruses (ERVs), such as viruses from the genus of gamaretroviruses, including Koala epidemic virus (KoRV), Mouse Mammary Tumor Virus (MMTV), Mouse Leukemia Virus (MLV) are adventitious agents that occur in any animal genome including, e.g., in hamster genomes and genomes of related species. ERVs are maintained in the genomes and may have certain advantages for the cells into whose genome they are integrated, including providing a source of genetic diversity and protection against other viral pathogens. However, they can become infectious. Cancer and/or epigenetic modifications can increase ERV awakening. Lewis et al. identified 403 possible retrovirus proteins in CHO cells based on a comparison of homologies to a database of 115 viruses. Lewis et al. reported that 40% of their mRNAs were expressed, thereby suggesting that many of these may be still be synthesizing retroviral components (Lewis et al., 2013, Supplement). In the present context, murine retrovirus type C sequences were used as a comparison tool (data obtained from a 1994 publication). There are four species in this group as noted in the Viralzone website (December 2015) hosted by SIB (Swiss Institute of Bioinformatics). They also occur frequently in mouse genome and are known to cause cancer in mice. However, as the person skilled in the art will appreciate, the sequences of many other retroviruses can be used to search for ERVs in cells of interest.

The engineered cell according to the present invention, may comprise a genome that, in most parts, is identical to the genome of the cell it is derived from such as a CHO-K1 cell. However, at least one or more, often many ERV elements which are part of these genomes will contain alterations as described herein.

Figure 2A:
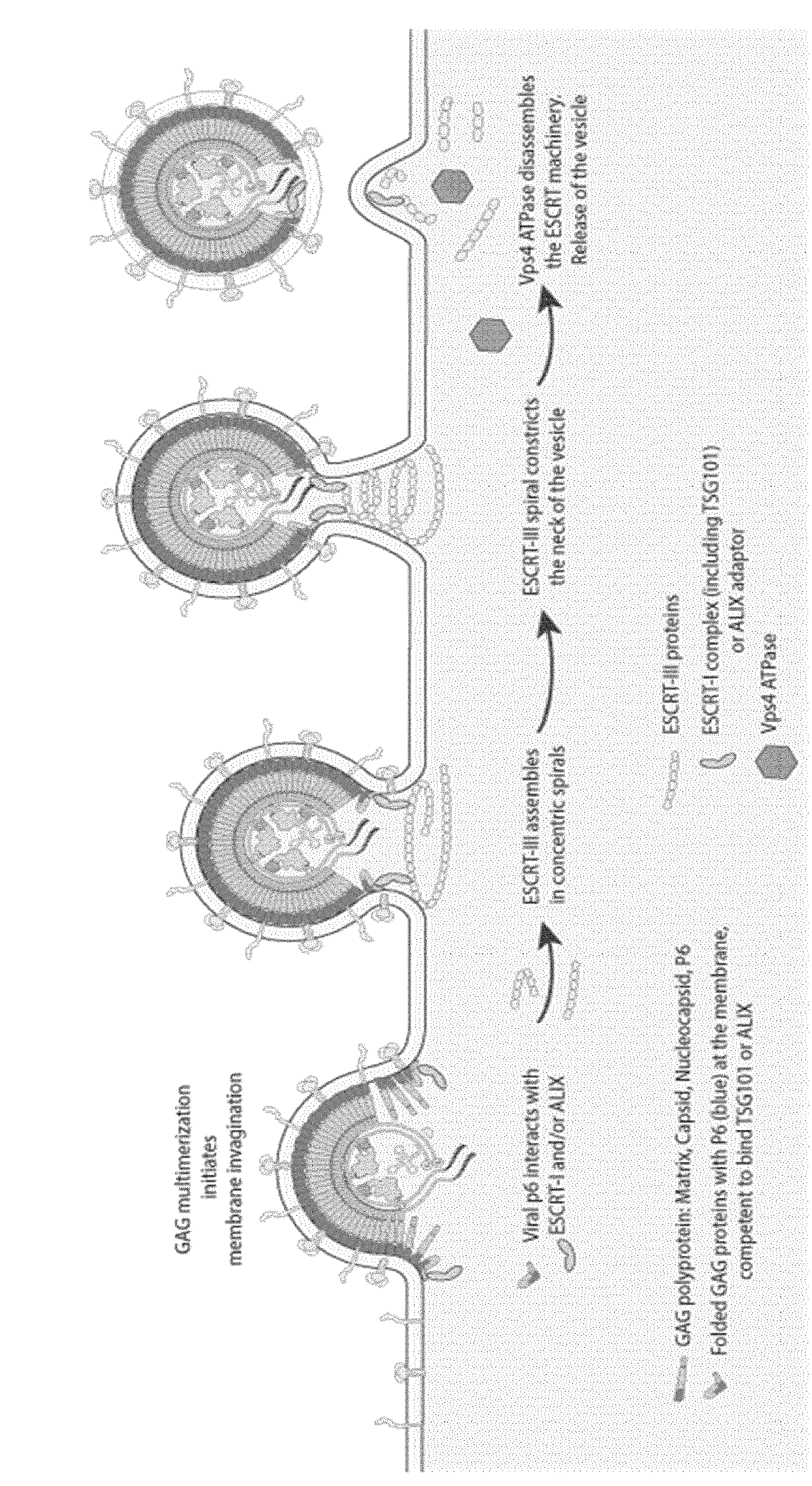
FIG. 2A shows the components of the ESCRT (endosomal sorting complexes required for transport) complex (comprising cytosolic protein complexes, known as ESCRT-0, ESCRT-I, ESCRT-II, and ESCRT-III and a number of accessory proteins including ALIX) and the interaction of the viral p6 protein therewith resulting in the release of viral vesicles.
Figure 2B:
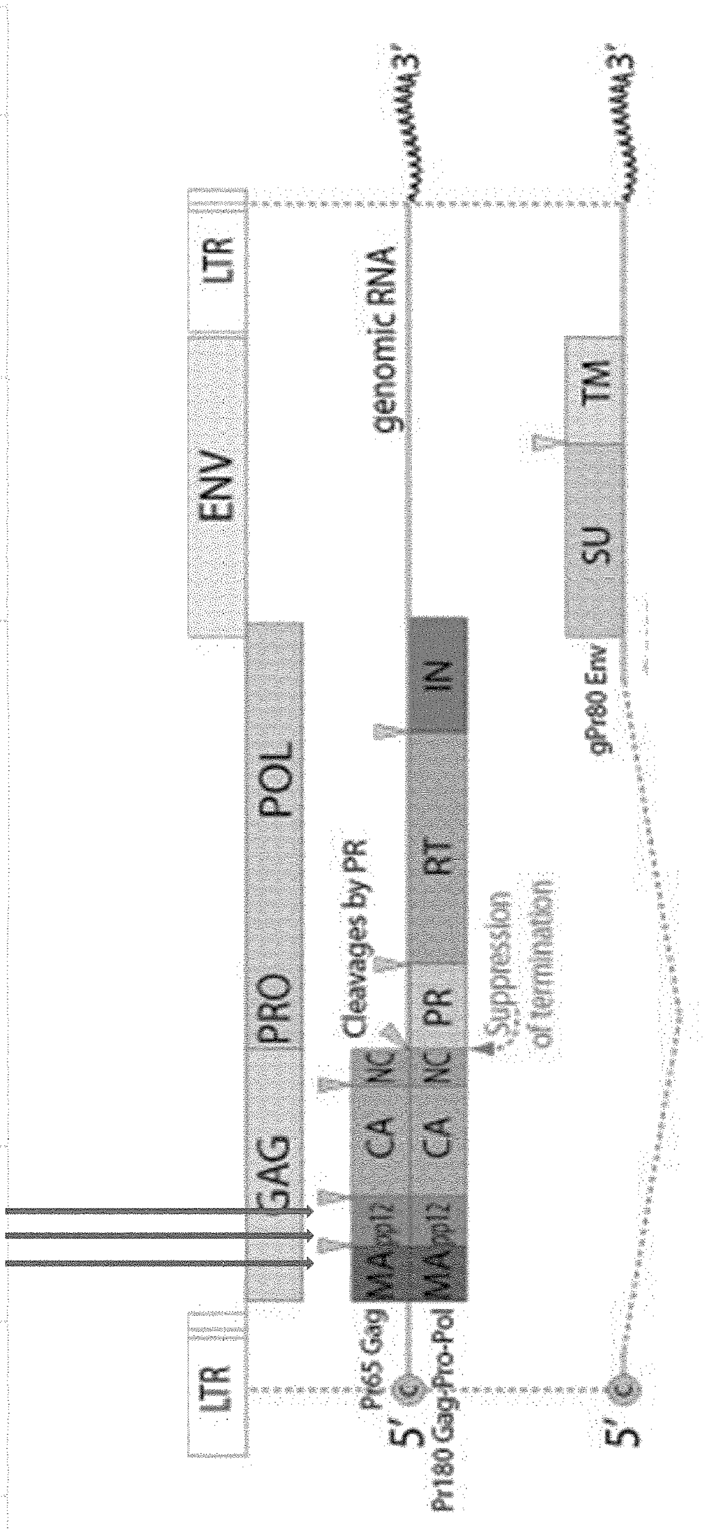
FIG. 2B shows different amino acid motives of ERVs allowing budding ("budding motives) that were determined via hidden Markov modeling (HMM) from the translated gag (group specific antigen) open reading frame (ORF).
Figure 3:
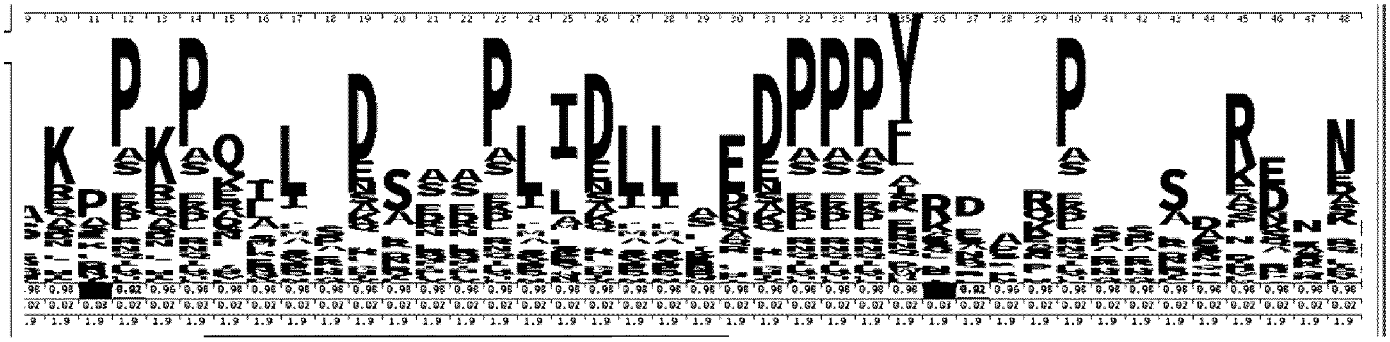
FIG. 3 shows ways of determining budding motives (see FIG. 1C) via HMM (Hidden Markov model) in pp12 encoded by the gag region. Based on the PPXY motif known to be common to gammaretroviruses, the overlapping PPYP motif from Group 1 and Group 2 CHO cell ERVs was determined and served as a target for mutagenesis. Also shown are the number of the first base pair of the compared sequences as listed.

An ERV element according to the present invention describes primarily a section of the ERV nucleic acid sequence that provides in the corresponding non-integrated virus a functional entity. As the person skilled in the art will appreciate, often parts of these sections are disrupted or deleted in the integrated virus DNA. Thus, included in this definition are all genes (gag, pol, env) and, secondarily, parts thereof set forth below and shown in FIG. 2B but also truncated and/or modified versions thereof that are present in the genome of a cell. ERV elements are referred to as being, e.g., from gag, if the gag gene is their source, but they do not necessarily encode a full functional Gag protein. ERV elements that are said to encode the Gag protein, encode a functional Gag protein.

The gag gene gives rise to a Gag precursor protein, which is expressed from the unspliced viral mRNA. The Gag precursor protein is cleaved by the virally encoded protease (a product of the pol gene) during the process of viral maturation into generally four smaller proteins designated MA (matrix), CA (capsid), NC (nucleocapsid), and a further protein domain (e.g. pp12 in murine leukemia virus or p6 in HIV).

The MA polypeptide is derived from the N-terminal, myristoylated end of the precursor protein. Most MA molecules remain attached to the inner surface of the virion lipid bilayer, stabilizing the particle.

The CA protein forms the conical core of viral particles.

The NC region of Gag is responsible for specifically recognizing the so-called packaging signal of the retrovirus. The packaging signal comprises four stem loop structures located near the 5' end of the viral RNA, and is sufficient to mediate the incorporation of a heterologous RNA into virions. NC binds to the packaging signal through interactions mediated by two zinc-finger motifs.

Another protein domain mediates interactions between precursor protein Gag and the accessory protein Vpr, leads to the incorporation of Vpr into assembling virions. The p6 region in HIV also contains a so-called late domain which is required for the efficient release of budding virions from an infected cell. (Hope & Trono, 2000).

The viral protease (Pro), integrase (IN), RNase H, and reverse transcriptase (RT) are expressed within the context of a Gag-Pol fusion protein. The Gag-Pol precursor is generally generated by a ribosomal frame shifting event, which is triggered by a specific cis-acting RNA motif (a heptanucleotide sequence followed by a short stem loop in the distal region of the Gag RNA). When ribosomes encounter this motif, they shift approximately 5% of the time to the pol reading frame without interrupting translation. The frequency of ribosomal frameshifting explains why the Gag and the Gag-Pol precursor are produced at a ratio of approximately 20:1.

During viral maturation, the virally encoded protease cleaves the Pol polypeptide away from Gag and further digests it to separate the protease, RT, RNase H, and integrase activities. These cleavages do not all occur efficiently, for example, roughly 50% of the RT protein remains linked to RNase H as a single polypeptide (p65) (Hope & Trono, 2000).

The pol gene encodes the reverse transcriptase. During the process of reverse transcription, the polymerase makes a double-stranded DNA copy of the dimer of single-stranded genomic RNA present in the virion. RNase H removes the original RNA template from the first DNA strand, allowing synthesis of the complementary strand of DNA. The predominant functional species of the polymerase is a heterodimer. All of the pol gene products can be found within the capsid of released virions.

The IN protein mediates the insertion of the proviral DNA into the genomic DNA of an infected cell. This process is mediated by three distinct functions of IN.

The Env protein is expressed from singly spliced mRNA. First synthesized in the endoplasmic reticulum, Env migrates through the Golgi complex where it undergoes glycosylation. Env glycosylation is generally required for infectivity. A cellular protease cleaves the protein into a transmembrane domain and a surface domain. (Hope & Trono, 2000).

Some ERVs of a genome are released from the cells in the form of virus-like particles and others are not. However, generally the ones that are released have a higher potential to become infectious. Thus, it is generally advantageous to have cells engineered, as described herein, that can express and release no or substantially no ERVs, preferably under standard or stressful culturing conditions. Substantially no ERVs are released if a cell culture comprising the so engineered cell releases less than 50%, less than 40%, less than 30%, less than 20%, less than 10%, preferably 5% of ERVs than their counterpart that has not been subjected to the ERV release reducing procedures described herein. Such a counterpart would, e.g., be a commercially available CHO-K1 cell. No or substantially no expression means that less than 50%, less than 40%, less than 30%, less than 20%, less than 10%, preferably 5%, unmutated Gag mRNA sequence can be detected by PCR and sequencing analysis. No release means that no or substantially no detectable viral sequence release occurs as assessed via a cDNA PCR assay, as shown e.g. in FIG. 21 or as obtained from QIAGEN, QuantiTect Rev. Transcription Kit®. As the person skilled in the art will also appreciate, cells that have been engineered to comprise nucleic acid sequence alterations that inactive protein/peptide production in one, two, three, four, 5, 6, 7, 8, 9, 10 ERV elements can also be advantageous and are part of the present invention. In fact, in certain embodiments it is advantageous to alter one or more ERV elements which is part of the genome of a cell of interest only by one or more mutations to maintain, where appropriate, positive roles that the ERVs might play within the cell. However, as discussed below, certain embodiments of the present invention are particularly suitable for high copy number ERVs (more than 30, 40 or 50 ERVs/per cell) and are able to accomplish that the modified cell does not show any expression of the respective ERV component.

A heterologous nucleic acid sequence is a nucleic acid sequence that does not occur in the cells prior to engineering according to the present invention, while related types of nucleic acid sequences may very well exist in the cell. A transgene as used in the context of the present invention is such a heterologous nucleic acid sequence, in particular a deoxyribonucleotide (DNA) sequence coding for a given mature protein (also referred to herein as a DNA encoding a protein), for a precursor protein or for a functional RNA that does not encode a protein (non-coding RNA). A transgene is isolated and introduced into a cell to produce the transgene product. Some preferred transgenes according to the present invention encode marker proteins such as GFP (green fluorescent protein). Those can be used to detect successful integration into, ergo alternation/inactivation of, ERV elements. Other transgenes are those that encode, e.g., proteins that shall ultimately be produced by the cell in question such as immunoglobulins (Igs) and Fc-fusion proteins and other proteins, in particular proteins with therapeutical activity ("biotherapeutics"). According to the present invention, additions include integrations such as targeted integrations. However, the person skilled in the art will appreciate that during the integration process certain nucleotides might be lost in the recipient genome. Those integrations are part of the present invention and are considered additions.

As used herein, the term transgene shall, in the context of a DNA encoding a protein, not include untranscribed flanking regions such as RNA transcription initiation signals, promoters or enhancers. Other preferred transgenes include DNA sequences encoding functional RNAs. Thus, the term transgene is used in the present context when referring to a DNA sequence that is introduced into a cell such as a eukaryotic host cell via transfection (which includes in the context of the present invention also transduction, i.e., the introduction via viral vectors) and which encodes a product of interest ("transgene expression product", e.g., "heterologous protein"). The transgene might be functionally attached to a signal peptide coding sequence, which encodes a signal peptide which in turn mediates and/or facilitates translocation and/or secretion across the endoplasmic reticulum and/or cytoplasmic membrane and is removed prior or during secretion.

A promoter sequence or just promoter is a nucleic acid sequence which is recognized by a host cell for expression of one or more nucleic acid sequences. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell. Promoters according to the present invention include inducible and non-inducible promoters. A nucleic acid sequence is under control of a promoter is the promoter exercises its function on said nucleic acid. The cells/vectors of the present inventions often contain such promoters.

Nucleic acid sequence alterations are alterations, such as additions/insertions, deletions and/or substitutions that do not occur in the cells prior to engineering according to the present invention.

As used herein, "genome editing" refers to the modification ("editing") of genomic sequences and may comprise a deletion of at least one nucleotide, an addition/insertion of at least one nucleotide, or a substitution of at least one nucleotide. The genomic sequence edited is referred to herein as target nucleic acid sequence. Targeted insertions are insertions that occur at a specific predetermined target site. Genome editing tools introduce double or single stranded breaks into the genome, e.g., via nucleases or nickases, and rely at least in part on the cellular recombination mechanisms (see discussion below) to repair these breaks. These tools also contain generally sequence specific DNA binding modules. ZFNs (Zinc-Finger Nucleases) and TALENs (transcription activator-like effector nucleases) enable a broad range of genetic modifications by inducing DNA double-strand breaks that stimulate error-prone non-homologous end joining (NHEJ) or homology-directed repair (HDR) at specific genomic locations.

The sequence specificity of CRISPR (clustered, regularly interspaced, short palindromic repeats) systems is determined by small RNAs. CRISPR loci are composed of a series of repeats separated by 'spacer' sequences that match the genomes of bacteriophages and other mobile genetic elements. The repeat-spacer array is transcribed as a long precursor and processed within repeat sequences to generate small crRNA that specify the target sequences (also known as protospacers) cleaved by CRISPR systems. For cleavage, the presence of a sequence motif immediately downstream of the target region is often required, known as the protospacer-adjacent motif (PAM). CRISPR-associated (cas) genes usually flank the repeat-spacer array and encode the enzymatic machinery responsible for crRNA (CRISPR RNA) biogenesis and targeting. Cas9 is a dsDNA endonuclease that uses a crRNA guide to specify the site of cleavage. Loading of the crRNA guide onto Cas9 occurs during the processing of the crRNA precursor and requires a small RNA antisense to the precursor, the tracrRNA, and RNAse III. In contrast to genome editing with ZFNs or TALENs, changing Cas9 target specificity does not require protein engineering but only the design of the short crRNA guide, also termed sgRNA.

Figure 7:
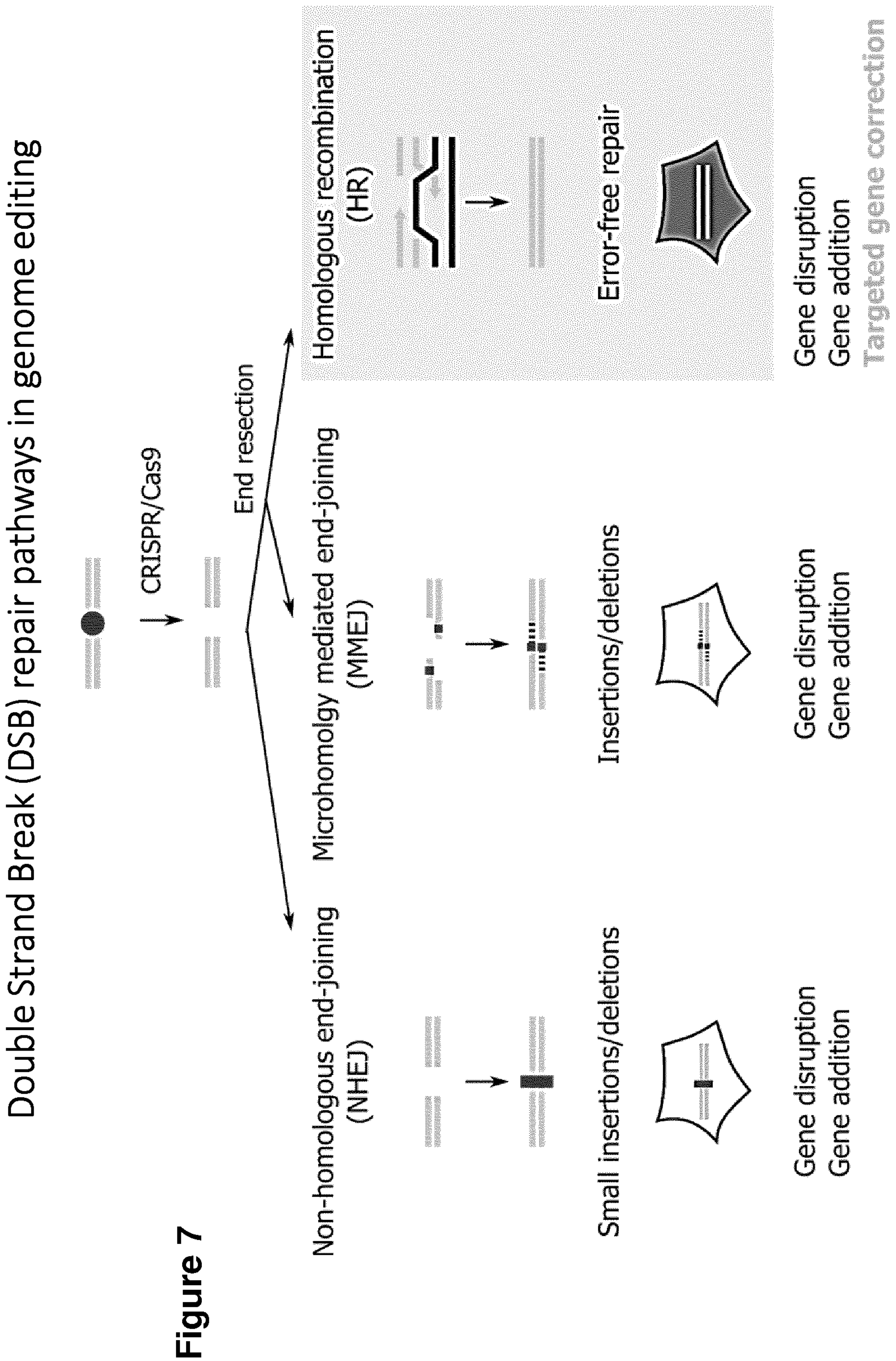
FIG. 7 shows the three main repair pathways competing for the repair of DSBs, namely, non-homologous end joining (NHEJ), Microhomology mediated end joining (MMEJ) and homologous recombination (HR). The pathway of repair affects the genome editing outcome, which may lead to deletions, gene conversion or to the effective restoration of the original sequence.
Figure 8:
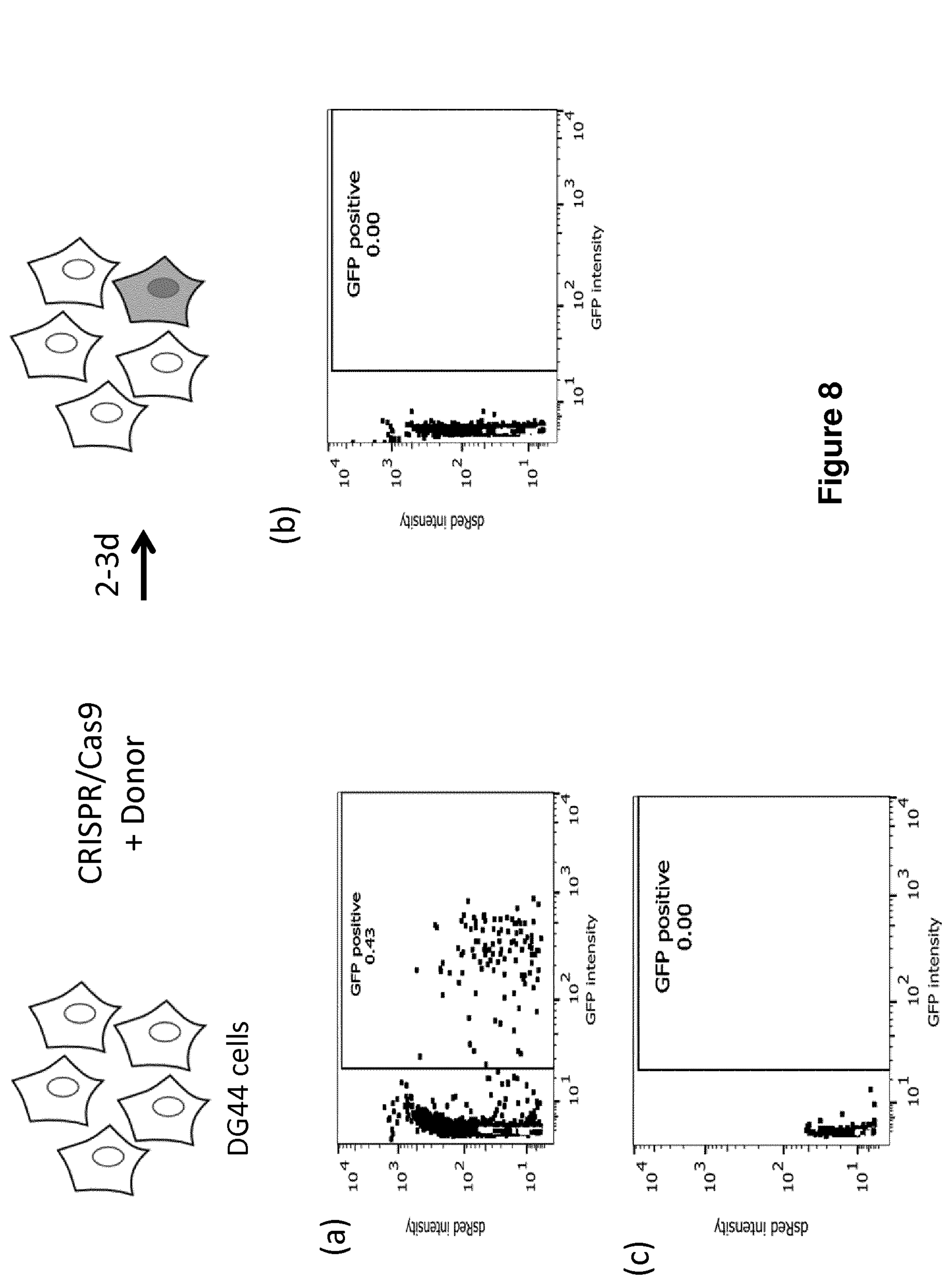
FIG. 8 shows the restoration of a functional GFP-coding sequence from a donor plasmid encoding part of GFP in the genome of DG44 CHO cells using the CRISPR/Cas 9 system. Results are shown for CRISPR/Cas 9+donor (a), CRISPR/Cas 9 only (b), and donor only (c). It can be seen that GFP reconstitution requires CRISPR/Cas9 as well as a donor plasmid (about 0.4% of GFP is repaired in the transfected cells in (a)). In the DG44 system, there is no GFP measurable with the CRISPR/Cas9 only or the donor plasmid only.
Figure 9:
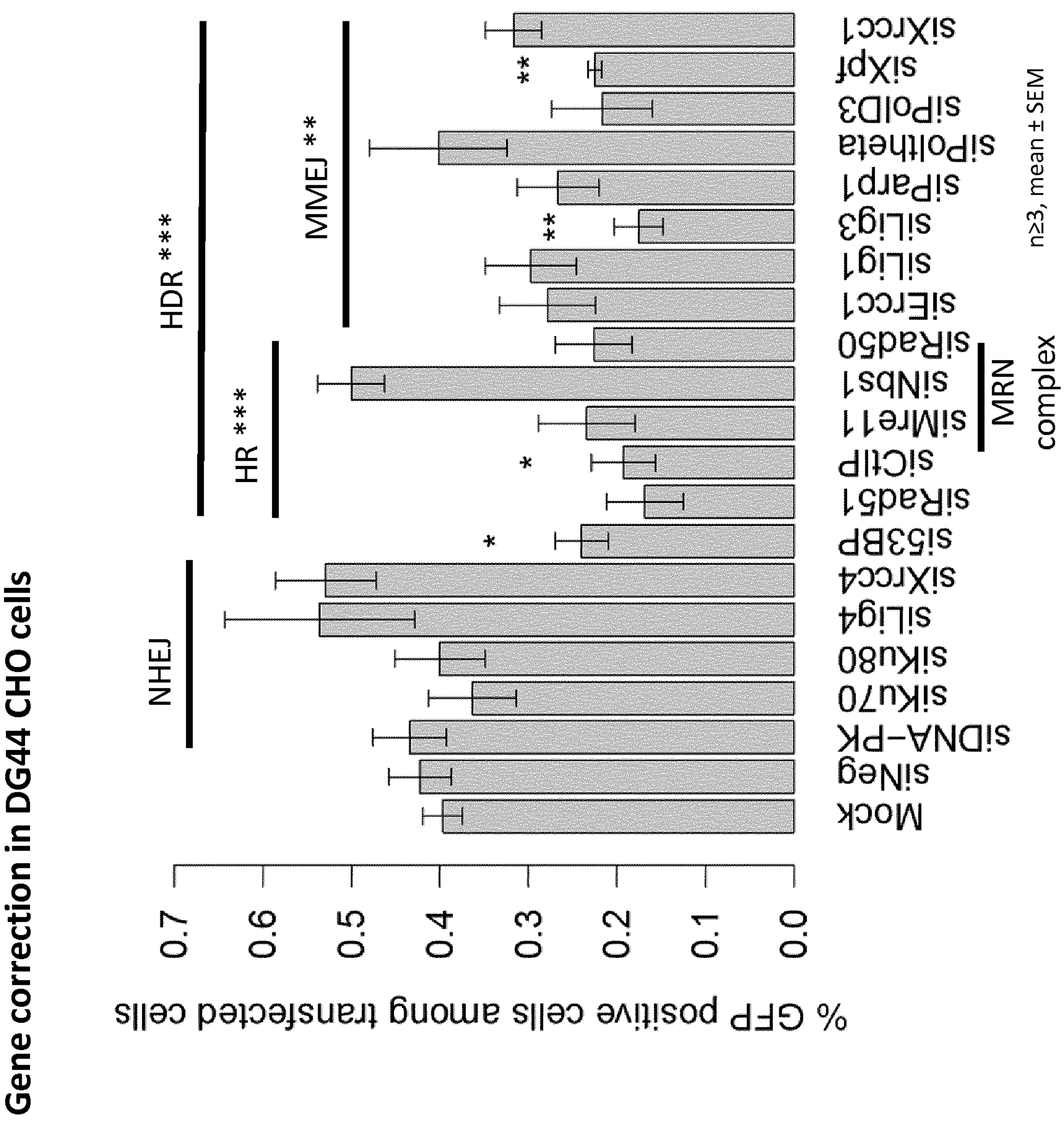
FIG. 9 shows the % of gene correction via the donor plasmid of FIG. 8 (DG44 CHO cells) depending on silencing/knockdown (via siRNAs) of genes influencing different repair pathways. Silencing of genes in the NHEJ pathway increases the % of correction (20% increase upon silencing/knockdown of Ligase 4 and XRCC4). Silencing/knockdown of genes in HDR (homologous directed repair pathways, HR and MMEJ) mostly reduces the % of correction. Silencing of certain genes in HDR increases the % of correction (Nbs4, part of the MRN complex). (The x axis shows the different silencing RNAs used organized according to repair pathway, * indicates significant differences).
Figure 10:
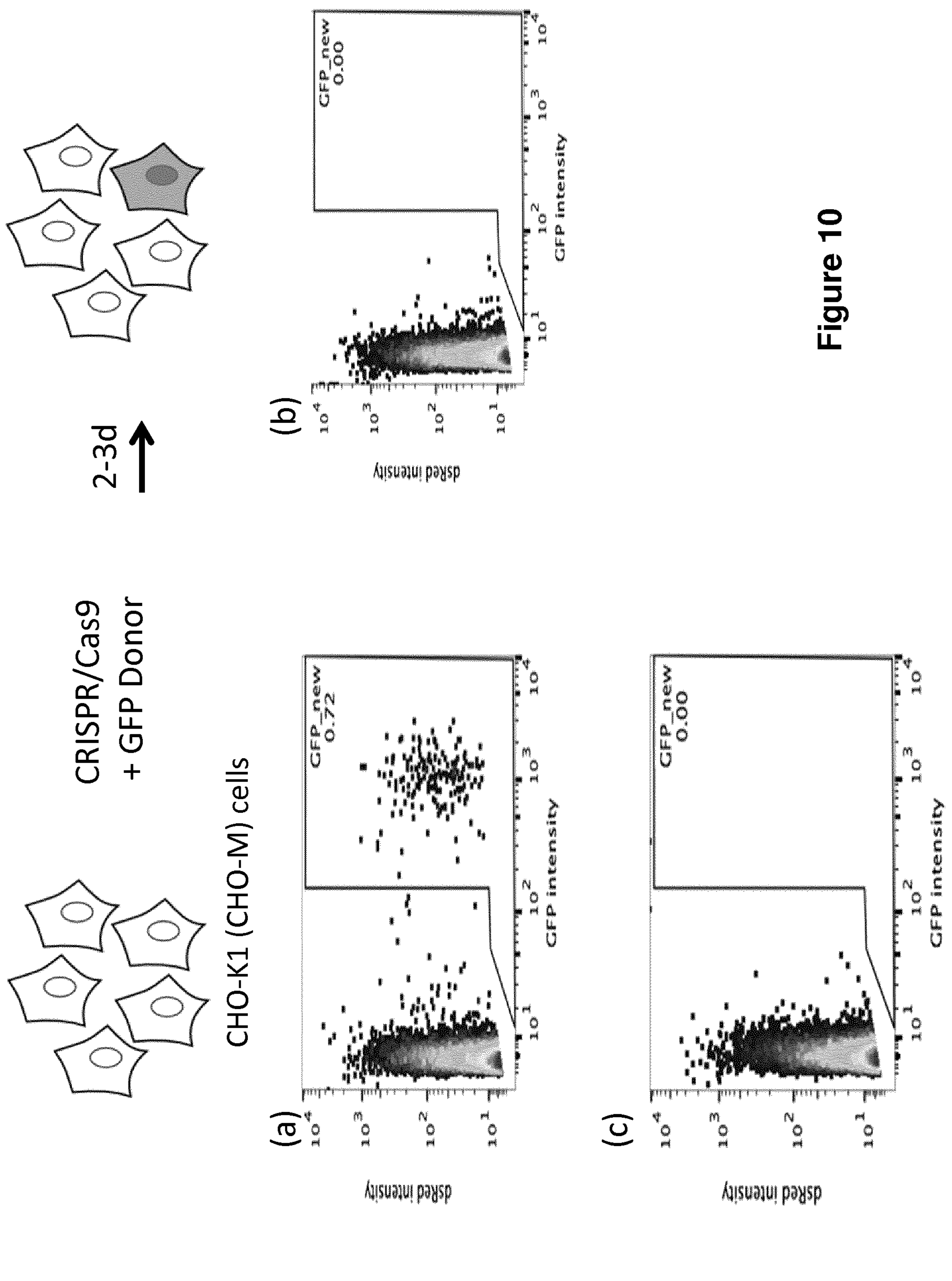
FIG. 10 shows the restoration of a functional GFP-coding sequence from a donor plasmid encoding part of GFP in the genome of CHO-M (CHO-K1 variant) cells using the CRISPR/Cas9 system. Transfection with the CRISPR/Cas9 as well as a donor plasmid leads to the 0.7% repaired GFP. The CHO-M cells are thus less recalcitrant to repair than the DG44 cells.
Figure 11:
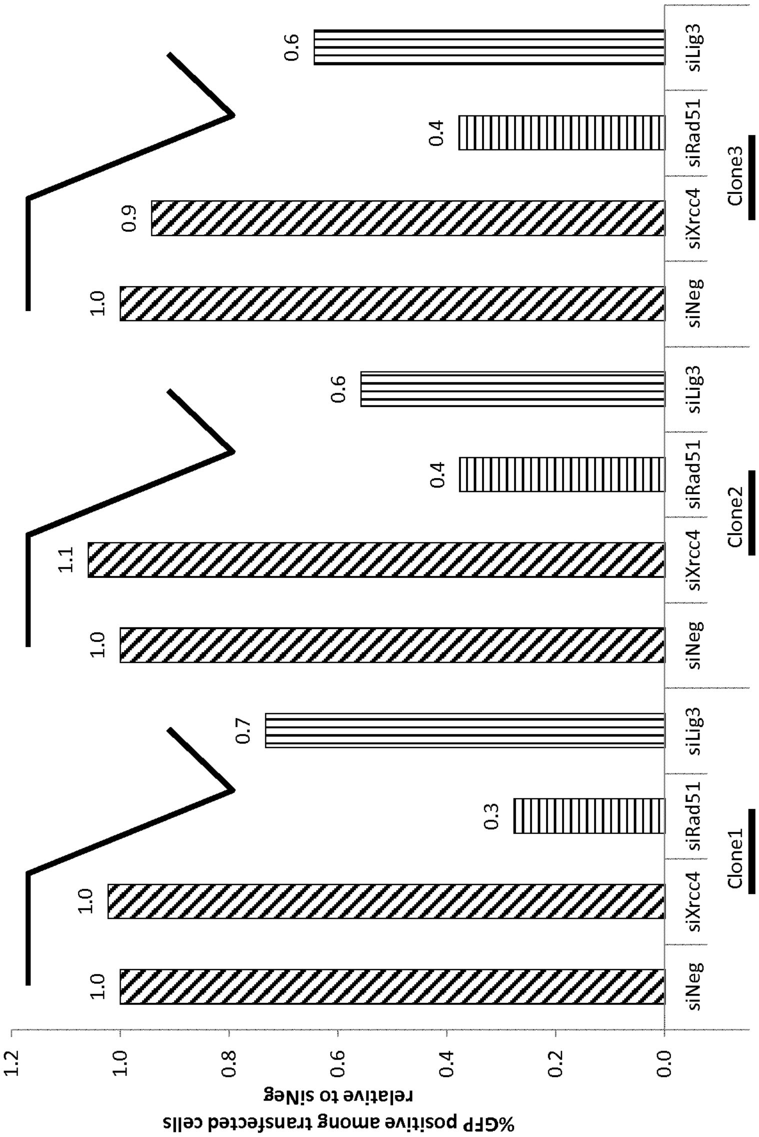
FIG. 11 shows the % of donor plasmid integration of FIG. 10 (CHO-K1 cells) depending on silencing/knockdown (via siRNAs) of genes influencing different repair pathways. Silencing of genes in HDR (homologous directed repair pathways, HR and MMEJ) reduced the % of gene correction. The Figure also shows a high degree of reproducibly of the results from the 3 clones tested. Silencing of Rad51 (via siRad51) and thus the slowdown/shut down of HR as repair pathway lead in all three clones to a significant reduction of GFP positive cells, while slowdown/shut down of the NHEJ via siXrcc4 had essentially no effect on the percentile of GFP positive cells.

To date, three different variants of the Cas9 nuclease have been adopted in genome-editing protocols. The first is wild-type Cas9, which can site-specifically cleave double-stranded DNA, resulting in the activation of the doublestrand break (DSB) repair machinery. DSBs can be repaired by the cellular Non-Homologous End Joining (NHEJ) pathway, resulting in insertions and/or deletions (indels) which disrupt the targeted locus. Alternatively, if a donor template (see FIG. 7) with homology to the targeted locus is supplied, the DSB may be repaired by the homology-directed repair (HDR) pathway allowing for precise replacement mutations to be made.

The Cas9 system was further engineered towards increased precision by developing a mutant form, known as Cas9D10A, with only nickase activity. This means it cleaves only one DNA strand, and does not activate NHEJ. Instead, when provided with a homologous repair template, DNA repairs are conducted via the high-fidelity HDR pathway only, resulting in reduced indel mutations. Cas9D10A is therefore in many applications more appealing in terms of target specificity when loci are targeted by paired Cas9 complexes designed to generate adjacent DNA nicks.

In the context of the present invention, a specific sequence or a consensus sequence of ERV elements are determined to specify the site of cleavage via, e.g., one of the systems above. Such a specific or consensus sequence is preferably between 5 and 50 base pairs long, preferably between 10 and 50 or between 15 and 25 or between 25 and 50 or 30 and 50. The consensus sequences may contain, e.g., 1, 2, 3, 4 or 5 mismatches (have more than 60%, 70%, 80%, 90% or 95% complementarity relative to each other), as long as cleave can still be performed. See, e.g, FIG. 21. The above systems are called non-naturally occurring systems or heterologous systems, which means that they are introduced to the cell rather than being a part of the cell prior to engineering according to the present invention.

A vector according to the present invention is a nucleic acid molecule capable of transporting another nucleic acid, such as a transgene that is to be expressed by this vector, to which it has been linked, generally into which it has been integrated. For example, a plasmid is a type of vector, a retrovirus or lentivirus is another type of vector. In a preferred embodiment of the invention, the vector is linearized prior to transfection. An expression vector comprises heterologous regulatory elements or is under the control of such regulatory elements that are designed to further the transcription and/or expression of a nucleic acid sequence, such as a transgene, carried by the expression vector. Regulatory elements comprise enhancers and/or promoters, but also a variety of other elements described herein. Among non-viral vectors, transposons are particularly attractive because of their ability to integrate single copies of DNA sequences with high frequency at multiple loci within the host genome (integrating vector). Unlike viral vectors, some transposons were reported not to integrate preferentially close to cellular genes, and they are thus less likely to introduce deleterious mutations. Moreover, transposons are readily produced and handled, comprising generally of a transposon donor vector containing the cargo DNA flanked by inverted repeat sequences and of a transposase-expressing helper plasmid or mRNA. Several transposon systems were developed to mobilize DNA in a variety of cell lines without interfering with endogenous transposon copies. For instance, the PiggyBac (PB) transposon originally isolated from the cabbage looper moth efficiently transposes cargo DNA into a variety of mammalian cells.

In the context of the present invention, vectors, in particular non-integrating vectors, may also be used for transient expression of a gene or a functional RNA. Transient expression is an expression for a limited amount of time and the time period of expression depends on the vector design and culturing conditions. However, transient expression means expression over a period of at least 24 hours but generally not more than 7 days.

Epigenetic regulatory elements can be used to protect the cargo DNA from unwanted epigenetic effects when placed near the transgene on plasmid vectors. For example, elements called matrix attachment region (MARs) were proposed to increase cargo DNA genomic integration and transcription while preventing heterochromatin silencing, as exemplified by the potent human MAR 1-68. They can also act as insulators and thereby prevent the activation of neighboring cellular genes. MAR elements have thus been used to mediate high and sustained expression in the context of plasmid or viral vectors. For transient gene expression, non-integrating vectors (sometimes referred to as episomal vectors) such as plasmids or non-integrating lentiviral (NIL) vectors may be used. They may be stably or transiently maintained and replicated within the host cell.

The vector sequence of a vector is the DNA or RNA sequence of the vector excluding any "other" nucleic acids such as transgenes as well as genetic elements such as MAR elements.

The term sequence identity refers to a measure of the identity of nucleotide sequences or amino acid sequences. In general, the sequences are aligned so that the highest order match is obtained. "Identity", per se, has a recognized meaning in the art and can be calculated using published techniques. (See, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity between two polynucleotide or polypeptide sequences, the term "identity" is well known to skilled artisans as defining identical nucleotides or amino acids at a given position in the sequence (Carillo, H. & Lipton, D., SIAM J Applied Math 48:1073 (1988)).

Whether any particular nucleic acid molecule is at least 50%, 60%, 70%, 75%, 80%, 85%, 90%, 95%, 96%, 97%, 98% or 99% identical to, for instance, the gammaretrovirus-like sequences of SEQ ID NOs. 1, 2, 3 or 4, or a part thereof (see, e.g., sequences disclosed in FIG. 18), can be determined conventionally using known computer programs such as DNAsis software (Hitachi Software, San Bruno, Calif.) for initial sequence alignment followed by ESEE version 3.0 DNA/protein sequence software (cabot@trog.mbb.sfu.ca) for multiple sequence alignments.

Whether the amino acid sequence is at least 50%, 60%, 70%, 75%, 80%, 85%, 90%, 95%, 96%, 97%, 98% or 99% identical to, for instance a protein expressed by SEQ ID NOs:1, 2, 3 or 4, or a part thereof, can be determined conventionally using known computer programs such the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences.

When using DNAsis, ESEE, BESTFIT or any other sequence alignment program to determine whether a particular sequence is, for instance, 95% identical to a reference sequence according to the present invention, the parameters are set such that the percentage of identity is calculated over the full length of the reference nucleic acid or amino acid sequence and that gaps in homology of up to 5% of the total number of nucleotides in the reference sequence are allowed.

Another preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

For example, a polynucleotide having 95% "identity" to a reference nucleotide sequence of the present invention, is identical to the reference sequence except that the polynucleotide sequence may include on average up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

The NCBI Basic Local Alignment Search Tool (BLAST) (Altschul et al. J. Mol. Biol. 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website, together with a description of how to determine sequence identity and sequence similarities using this program.

The present invention includes nucleic acid and/or amino acid molecules having 80%, 85%, 90% or more, 95% or more, 98% sequence identity or complete sequence identity with the sequences disclosed herein and any fragment thereof, in particular fragments spanning up to 40 bps, 30 bps or 20 bps left and right of a PPYP motif.

The Recombination Pathways

The recombination pathways, also known as DNA recombination pathways, are cellular pathways that lead to DNA damage repair, such as the joining of DNA molecule extremities after chromosomal double-strand breaks (DSBs), and to the exchange or fusion of DNA sequences between chromosomal and non-chromosomal DNA molecules, such as e.g. the crossing-over of chromosomes at meiosis or the rearrangement of immunoglobulin genes in lymphocytic cells. The main recombination pathways are the homologous recombination pathway (HR), the non-homologous end-joining pathway (NHEJ) and the microhomology-mediated end-joining (MMEJ) and alternative end-joining (Alt-EJ) pathways.

In the context of the present invention, knock-outs of certain members of one or more of the pathways are often generated via complimentary nucleic acid sequences. A nucleic acid sequence, such as a DNA or RNA, is complimentary to another DNA or RNA, if the nucleotides of, e.g., two single stranded DNA stands or two single stranded RNA strands can form stable hydrogen bonds, such as a hydrogen bond between guanine (G) and cytosine (C). In the cell, complementary base pairing allows, e.g., cells to copy information from one generation to another. In RNA interference (RNAi) complementary base pairing allows, the silencing or complete knock-out of certain target genes. Essentially, siRNA, shRNA or miRNA sequence specifically reduce or knock-out expression of a target gene by having a single RNA strand (e.g. the anti-sense strand in siRNA) align with RNA, in particularly the mRNA of the host cell. The degree of complementarity between two nucleic acid strands may vary, from complete complementarity (each nucleotide is across from its opposite) to partial complementary (50%, 60%, 70%, 80%, 90% or 95%). The degree of complementarity determines the stability of the complex and thus how successfully a gene can be, e.g., knocked-out. Thus, complete or at least 95% complementarity is preferred.

The Mechanisms of Homologous Recombination (hr), Nhej and Mmej

Transgenes use the Recombination Machineries to Integrate at a Double Strand Break Into the Host Genome.

Double-strand breaks (DSBs) are the biologically most deleterious type of genomic damage potentially leading to cell death or a wide variety of genetic rearrangements. Accurate repair is essential for the successful maintenance and propagation of the genetic information. There are two major DSB repair mechanisms: NHEJ and HR. A third mechanism, called MMEJ often takes effect when the two major DSB repair mechanisms fail. Homologous recombination is a process for genetic exchange between DNA sequences that share homology and is operative predominantly during the S/G2 phases of the cell cycle, while NHEJ simply pieces together two broken DNA ends, usually with no sequence homology, and it functions in all phases of the cell cycle but is of particular importance during G0-G1 and early S-phase of mitotic cells. In vertebrates, HR, NHEJ and MMEJ differentially contribute to DSB repair, depending on the nature of the DSB and the phase of the cell cycle.

NHEJ: Basic Mechanisms

Conceptually, the molecular mechanism of the NHEJ process seems to be simple: 1) a set of enzymes capture the broken DNA molecule, 2) a molecular bridge that brings the two DNA ends together is formed and 3) the broken molecules are re-ligated. To perform such reactions, the NHEJ machinery in mammalian cells involves two protein complexes, the heterodimer Ku80/Ku70 associated with DNA-PKcs (catalytic subunit of DNA-dependent protein kinase) and DNA ligase IV with its co-factor XRCC4 (X-ray-complementing Chinese hamster gene 4) and many protein factors, such as Artemis and XLF (XRCC4-like factor; or Cernunnos). NHEJ is frequently considered as the error-prone DSB repair because it simply pieces together two broken DNA ends, usually with no sequence homology and it generates small insertions and/or deletions. NHEJ provides a mechanism for the repair of DSBs throughout the cell cycle, but is of particular importance during G0-G1 and early S-phase of mitotic cells. The repair of DSBs by NHEJ is observed in organisms ranging from bacteria to mammals, indicating that it has been conserved during evolution.

After DSB formation the key step in NHEJ repair pathway is the physical juxtaposition of the broken DNA ends. NHEJ is initiated by the association of the Ku70/80 heterodimer protein complex to both ends of the broken DNA molecule to capture, tether the ends together and create a scaffold for the assembly of the other NHEJ key factors. The DNA-bound Ku heterodimer complex recruits DNA-PKcs to the DSB, a 460 kDa protein belonging to the PIKK (phosphoinositide 3-kinase-like family of protein kinases) and activates its serine/threonine kinase function. Two DNA-PKcs molecules interact together across the DSB, thus forming a molecular bridge between both broken DNA ends and inhibit their degradation. Then, DNA ends can be directly ligated, although the majority of termini generated from DSB have to be properly processed prior to ligation. Depending of the nature of the break, the action of different combinations of processing enzymes may be required to generate compatible overhangs, by filling gaps, removing damaged DNA or secondary structures surrounding the break. This step in the NHEJ process is considered to be responsible for the occasional loss of nucleotides associated with NHEJ repair. One key end-processing enzyme in mammalian NHEJ is Artemis, a member of the metallo-β-lactamase superfamily of enzymes, which was discovered as the mutated gene in the majority of radiosensitive severe combined immunodeficiency (SCID) patients. Artemis has both a 5→3' exonuclease activity and a DNA-PKcs-dependent endonuclease activity towards DNA-containing ds-ss transitions and DNA hairpins (Ma et al., 2002). Its activity is also regulated by ATM. Thus, Artemis seems likely to be involved in multiple DNA-damage responses. However, only a subset of DNA lesions seem to be repaired by Artemis, as no major defect in DSB repair were observed in Artemis-lacking cells.

DNA gaps must be filled in to enable the repair. Addition of nucleotides to a DSB is restricted to polymerases μ and λ. By interaction with XRCC4, polynucleotide kinase (PNK) is also recruited to DNA ends to permit both DNA polymerization and ligation. Finally, NHEJ is completed by ligation of the DNA ends, a step carried out by a complex containing XRCC4, DNA ligase IV and XLF. Other ligases can partially substitute DNA ligase IV, because NHEJ can occur in the absence of XRCC4 and Ligase IV. Furthermore, studies showed that XRCC4 and Ligase IV do not have roles outside of NHEJ, whereas in contrast, KU acts in other processes such as transcription, apoptosis, and responses to microenvironment.

The NHEJ may be decreased or shut down in different ways, many of which directly affect the above referenced proteins (e.g., the heterodimer Ku80/Ku70, DNA-PKcs, but in particular DNA ligase IV, XRCC4, Artemis and XLF (XRCC4-like factor; or Cernunnos), PIKK (phosphoinositide 3-kinase-like family of protein kinases). However, while NHEJ is, in many application, undesirable the inaccurate repair of the double strand break general destroys the functionality of the gene in which the double strand break occurs, which is often all that is required in the context of the present invention. Accordingly, the present invention also includes embodiments, in which increase of the NHEJ is desirable.

HR: Basic Mechanisms

Homologous recombination (HR) is a very accurate repair mechanism. A homologous chromatid serves as a template for the repair of the broken strand. HR takes place during the S and G2 phases of the cell cycle, when the sister chromatids are available. Classical HR is mainly characterized by three steps: 1) resection of the 5' of the broken ends, 2) strand invasion and exchange with a homologous DNA duplex, and 3) resolution of recombination intermediates. Different pathways can complete DSB repair, depending on the ability to perform strand invasion, and include the synthesis-dependent strand-annealing (SDSA) pathway, the classical double-strand break repair (DSBR), the break-induced replication (BIR), and, alternatively, the single-strand annealing (SSA) pathway. All HR mechanisms are interconnected and share many enzymatic steps.

The first step of all HR reactions corresponds to the resection of the 5'-ended broken DNA strand by nucleases with the help of the MRN complex (MRE11, RAD50, NBN (previously NBS1, for Nijmegen breakage syndrome 1)) and CtIP (CtBP-interacting protein). The resulting generation of a 3' single-stranded DSB is able to search for a homologous sequence. The invasion of the homologous duplex is performed by a nucleofilament composed of the 3'ss-DNA coated with the RAD51 recombinase protein. The requirement of the replication protein A (RPA), an heterotrimeric ssDNA-binding protein, involved in DNA metabolic processes linked to ssDNA in eukaryotes, is necessary for the assembly of the RAD51-filament. Then RAD51 interacts with RAD52, which has a ring-like structure to displace RPA molecules and facilitate RAD51 loading. Rad52 is important for recombination processes in yeast. However, in vertebrates, BRCA2 (breast cancer type 2 susceptibility protein) rather than RAD52 seems to play an important role in strand invasion and exchange. RAD51/RAD52 interaction is stabilized by the binding of RAD54. RAD54 plays also a role in the maturation of recombination intermediates after D-loop formation. In the other hand, BRCA1 (breast cancer 1) interacts with BARD1 (BRCA1 associated RING domain 1) and BACH1 (BTB and CNC homology 1) to perform ligase and helicase DSB repair activity, respectively. BRCA1 also interacts with CtIP in a CDK-dependent manner and undergoes ubiquitination in response to DNA damage. As a consequence, BRCA1, CtIP and the MRN complex play a role in the activation of HR-mediated repair of DNA in the S and G2 phases of the cell cycle.

The invasion of the nucleofilament results in the formation of a heteroduplex called displacement-loop (D-loop) and involves the displacement of one strand of the duplex by the invasive strand and the pairing with the other. Then, several HR pathways can complete the repair, using the homologous sequence as template to replace the sequence surrounding the DSB. Depending of the mechanism used, reciprocal exchanges (crossovers) between the homologous template and the broken DNA molecule may be or may not be associated to HR repair. Crossovers may have important genetic consequences, such as genome rearrangements or loss of heterozygosity.

The five Rad51 paralogs are also involved in homologous recombination: Xrcc2, Xrcc3, Rad51B, Rad51C, Rad51D. Rad51 paralogs form two types of complexes: one termed BCDX2 comprises Rad51B, Rad51C, Rad51 D and Xrcc2; the other contains Rad51C and Xrcc3 (CX3). The first complex has been proposed to participate in the formation and/or stabilization of the Rad51-DNA complex. The role of the second complex seems to be branch migration and resolution of the Holliday junction.

As previously reported, increasing the HR relative to the NHEJ (see US patent pub. 20120231449, which is incorporated herein by reference in its entirety) can be used to enhance and/or facilitate transgene expression.

Advantages of decreasing or shutting down HR have also been described (WO 2014/118619, US Patent Publication 20150361451, which is incorporated herein by reference in its entirety). HR may be decreased or shut down in different ways, many of which directly affect the above referenced proteins (see also Table C; however it is noted that there is no clear differentiation between HDR different pathways). RNAs, such as siRNAs or shRNAs are generally used to accomplish the decrease or shutdown.

Microhomology-Mediated End Joining (MMEJ)

When the other recombination pathways fail or are not active, DSBs can be repaired by another, error-prone repair mechanism, namely MMEJ. This pathway still needs to be fully characterized and is sometimes also referred to as alternative end-joining (alt-EJ), although it is unclear whether these two processes are based on the same mechanism. The most characteristic feature of this pathway, which distinguishes it from NHEJ, is the use of 5-25 bp microhomologies during the alignment of broken DNA strands and results, in contrast to the NHEJ pathway, to the deletion of larger stretches of nucleic acids in the target genome, e.g. more than 20, 40, 60, 80, 100, 150, 200 bps, which is advantageous in many embodiments of the present invention.

MMEJ can occur at any time of the cell cycle and is independent of core NHEJ and HR factors, i.e. Ku70, Ligase IV and Rad52 genes. Instead MMEJ initiation relies on its own set of proteins, the most important ones being the components of the MRN complex (MRX in yeast) comprising Mre11, Rad50 and Nbs1 (Xrs2 in yeast), also implicated in the first steps of HR (Ma et al., 2003). Apart from the MRN complex many other factors have been proposed to participate in MMEJ, and in the related DNA synthesis-dependent SD-MMEJ mechanism, e.g. CTBP-interacting protein, poly (ADP-ribose) polymerase 1 (PARP1), the ligase III/Xrcc1 complex, ligase I, DNA polymerase θ (Yu and McVey, 2010), and the ERCC1/XPF complex. However, many more proteins may also take part in this process.

It has been suggested that in the absence of other DNA-end binding proteins (like Ku or Rad51) the DSBs are recognized by PARP1 which then initiates their repair through MMEJ. The repair process, similarly to HR, starts with 5' to 3' end resection, which exposes short regions of homology on each side of the break. This processing step is conducted by the MRN complex and regulated by CtIP. The complementary regions (present in the 3' ssDNA fragments) pair together and the non-complementary segments (flaps) are removed, probably by the ERCC1/XPF complex. Gaps (if any) are then filled in by a polymerase (e.g. DNA polymerase θ or δ and breaks joined by the ligase I or ligase III/Xrcc1 complex.

In the absence of immediate microhomology regions at the DNA ends, which is most often the case, a more distant fragment of the repaired molecule can be copied using an accurate DNA polymerase (e.g. polymerase θ). This duplicated region then participates in the alignment of DNA ends, which results in an insertion in the created junction. This more complex variant of microhomology-mediated repair has been termed synthesis-dependent MMEJ (SD-MMEJ).

Although MMEJ was thought to act as an alternative recombination repair pathway, it has been shown to be very efficient in the process of IgH class switch recombination in B lymphocytes, suggesting that it might be more than a backup mechanism. It is also possible that some DSBs, e.g. incompatible overhangs or blunt ends (which are poor NHEJ and/or HR targets) might be more efficiently repaired by MMEJ.

Figure 12B:
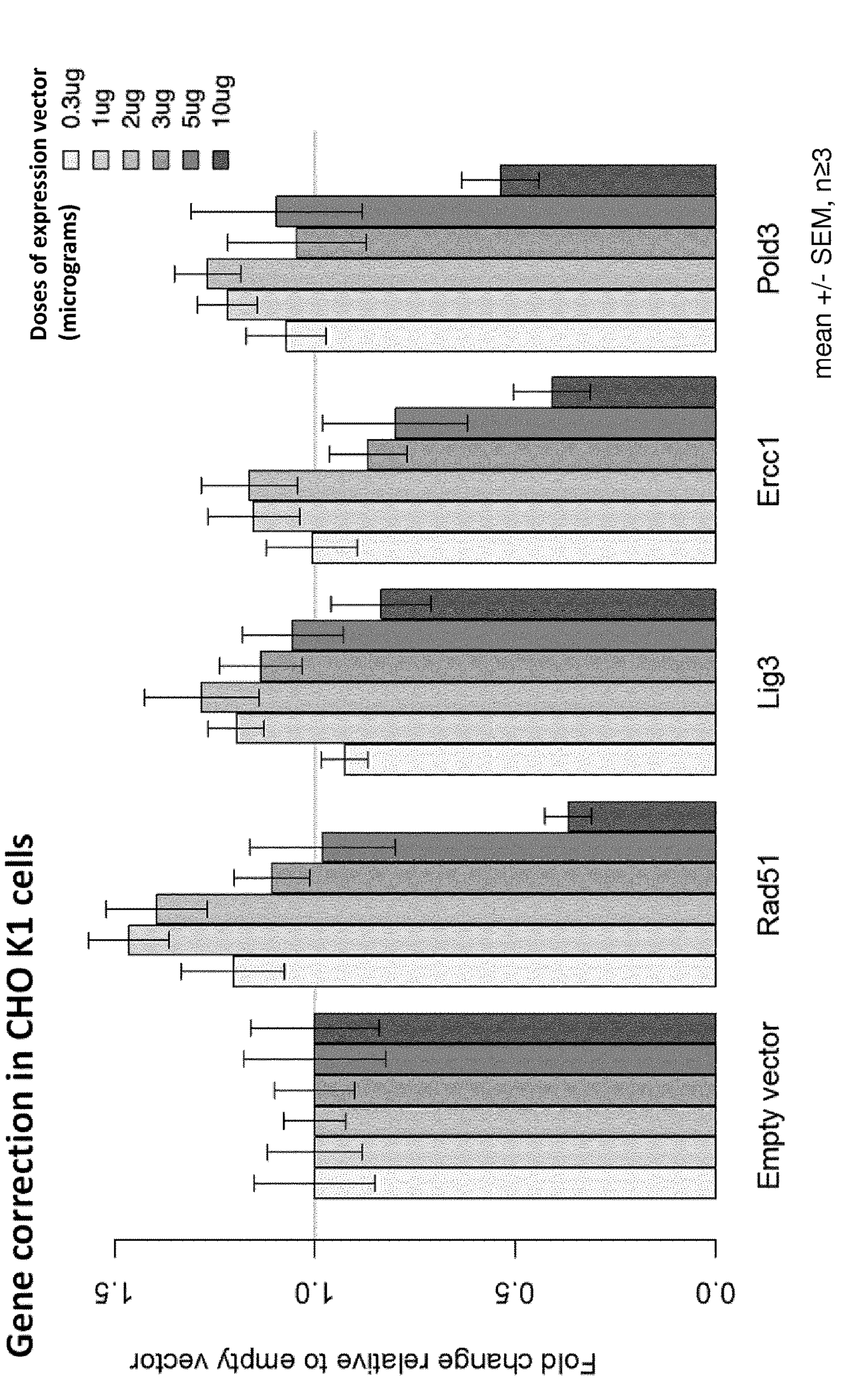
FIG. 12B shows the increase of expression of rate limiting HR and/or MMEJ proteins stimulates gene correction in a dose dependent manner. As can be seen an empty vector provides a base level of 1, wherein certain doses of expression vectors providing the rate liming proteins shown increase (upregulate the respective gene) gene correction, by more than 0.05 fold, more than 0.1 fold, 0.2 fold, 0.3 fold, 0.4 fold or 0.5 fold.

FIG. 12B shows the increase of expression of rate limiting HR and/or MMEJ proteins stimulates gene correction in a dose dependent manner. As can be seen an empty vector provides a base level of 1, wherein certain doses of expression vectors providing the rate liming proteins shown increase, ergo upregulate gene correction, by more than 0.05 fold, more than 0.1 fold, 0.2 fold, 0.3 fold, 0.4 fold or 0.5 fold. However, as the person skilled in the art will appreciate any of the proteins shown, e.g., Table C can be upregulated accordingly.

Detection of Possible Unexpected Adventitious Agents Such as Viruses

The characterization of all viral-like elements in the genome of a cell of interest such as a CHO genome allows for the characterization of potential new adventitious agents from master cell banked lines. This approach may replace many of the numerous assays that are currently being applied to characterize a producer cell clone, as needed for the regulatory approval of any biotherapeutic produced by cell lines. The characterization can also be used in the context of the analysis of production lots on a routine basis. Efficient CHO genome editing by targeted gene editing via, e.g. homologous recombination, may be used to remove expressed retroviral elements that are present in the genomes of cultured cells of interest, including CHO cells, such as CHO-K1 cells resulting in a reduced viral genomic load.

There are currently several available commercial services for gene editing or transgene-targeted integration that rely on homologous recombination mechanisms. These include the Zn-finger, Talen and CRISPR/Cas9 nucleases and Adenoviral vectors of e.g. SAFC-SANGAMO in the US, CELLECTIS in France, and HORIZON in the UK. However, two of these tools, Zn-finger and Talen, remain difficult to access and to use, as a specific nuclease and/or vector has to be engineered for each genomic sequence that is edited, whereas the availability of the third (CRISPR) remains highly uncertain. Furthermore, homologous recombination remains quite an inefficient process in the cell, requiring the screening of many candidate cell lines. Deleting the two alleles of a given gene thus often requires multiple rounds of mutagenesis and cell clone isolation and characterization. Thus, these current technologies are often too slow and too costly to allow for the systematic engineering of cellular genomes, as required for instance to remove multiple expressed viral gene remnants dispersed in the CHO genome. The engineering of metabolic pathways and recombination mechanisms in the CHO cell pave the way towards more efficient genome editing approaches by one of the recombination pathways, wherein, in most instances, homologous recombination is preferred.

To identify expressed ERV elements, the genome sequence of a CHO cell line (for instance SELEXIS'S CHO-K1-derived CHO-M cells) was determined with an approximately 120-fold coverage using the PACBIO (Pacific Bioscience Inc.) technology. The genome sequencing can be, e.g., performed in the PacBio RS II™ long-read sequencer.

The CHO genome was assembled in approximately 7200 contigs displaying an N50 size of 6.1 Mb.

Identification and Characterization of Expressed Erv Elements in the Cho Genome

CHO genome sequences displaying sequence similarities to known murine retroviral sequences were identified using the BLAST algorithm, searching for the viral GAG, POL and ENV element coding sequences, with a sequence conservation of at least 80%, as well as the presence of the viral long terminal repeats (LTR).

Figure 13:
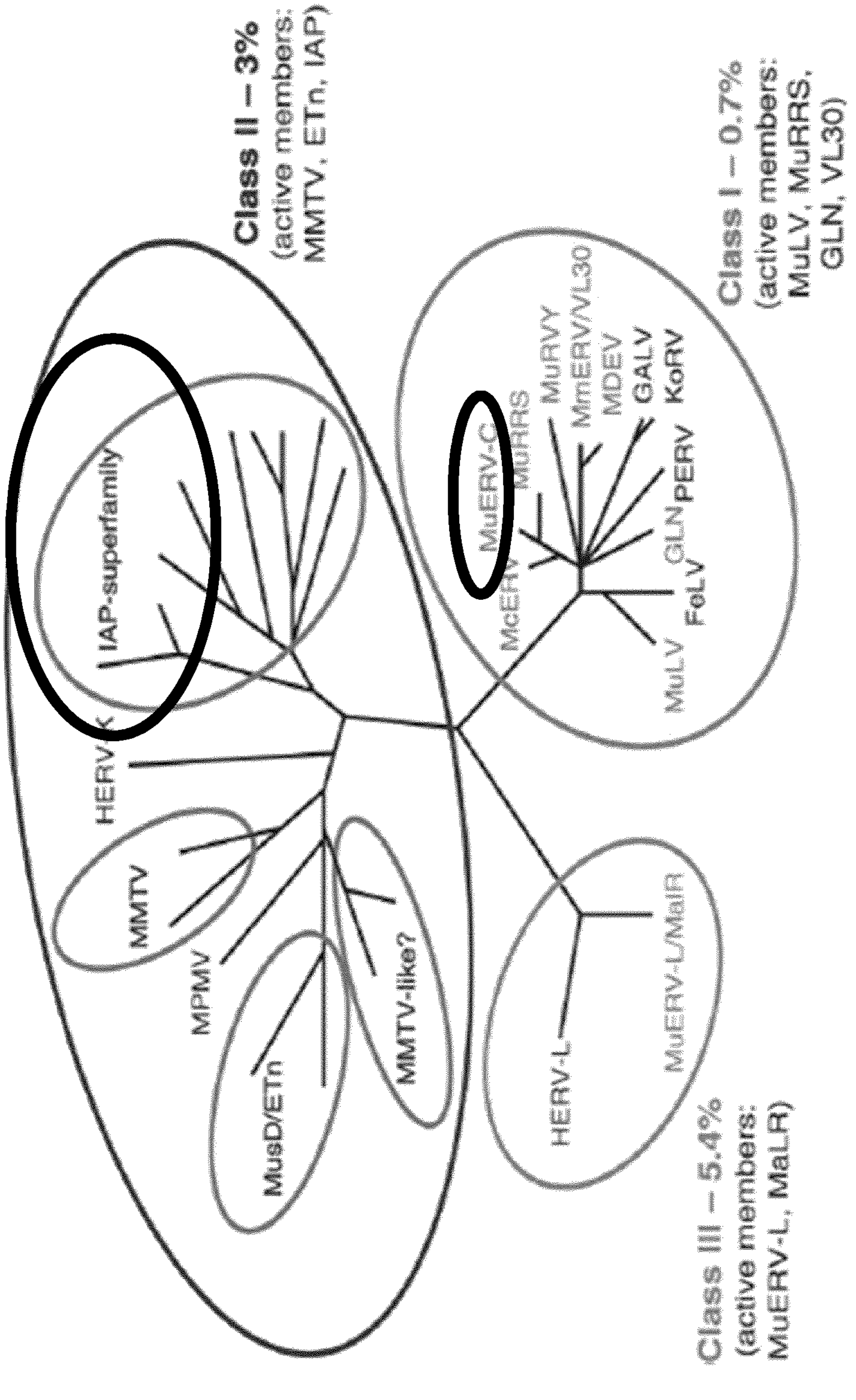
FIG. 13 shows the three classes of gammaretroviruses that might be integrated into the genome of the cells to form gammaretrovirus—related ERVs. The figure indicates viruses within each class (I-III) that were found to be present and active when analyzing a CHO genome obtained via PACBIO sequencing, searching for GAL, POL, ENV, LTR sequences (80% coverage, 80% sequence identity): 159 IAP (Intracisternal A-type particles) sequences and 144 type C murine ERV-like sequences were found (boldly circled), as well as 6 sequences related to GALV (Gibbon Ape Leukemia Virus).

As depicted in FIG. 13, three classes of gammaretroviruses have been identified, all of which may contribute to ERVs or ERV elements found in cells of interest. ERV elements that are expressed to produce a functional protein are of particular interest in the present context. A database of viral, in particular retroviral and/or microbial-like sequences within cells of interest, serves as a starting point. A corresponding database of the respective RNA sequences of those cells provides information as to which of the DNA elements are actually expressed and may encode a functional protein.

Construction of a Database of Relevant DNA Elements

Dispersed repeated sequences from past viral and retroviral integrations and retro-transposition events in the genome of cells of interest, e.g. cells used in the production of biotherapeutics, in particular those elements that remain expressed, are identified.

As a first step in identifying expressed ERV elements, the genome sequence of a CHO cell line (SELEXIS'S CHO-K1-derived CHO-M) was determined with a coverage of approximately 120-fold. For this, the PACBIO (Pacific Bioscience Inc.) technology was used. Such extensive sequencing can be, e.g., performed in the PacBio RS II™, original long-read sequencer. However, as the person skilled in the art will appreciate, other single molecule DNA sequencing technologies and apparatuses can equally well be used. Specific PCR amplifications and targeted DNA sequencing of relevant loci to obtain, e.g., a CHO-M genome sequence version 3.0 was performed.

The CHO-M genome was assembled in approximately 7200 contigs displaying an N50 size of 6.1 Mb.

To construct a database of DNA or cDNA indicator sequences for potential adventitious microbial contaminants, as based on list of adventitious agents whose screening is currently requested by agencies such as the FDA, genome sequences displaying sequence similarities to known murine retroviral sequences were identified.

To map their positions within the CHO-M genome scaffolds, CHO-M genome sequences displaying sequence similarities to known murine retroviral sequences (for instance the ML2G sequences, Lie et al, 2014) were identified using the BLAST algorithm, searching for the viral GAG, POL and ENV coding sequences, with a sequence conservation of at least 80%. The Blast alignment was run separately for each of these coding sequences. In addition, the presence of the viral long terminal repeats (LTR) was investigated, also via Blast with a threshold of 80%. The average sequence identify between the ML2G sequences and viral GAG, POL and ENV were determined to be 92%. The average sequence identify between GAG, POL and ENV and Mouse Leukemia Virus is 66%. In some instances, the ERVs were not complete, and only certain ERV elements were found.

Figure 4A:
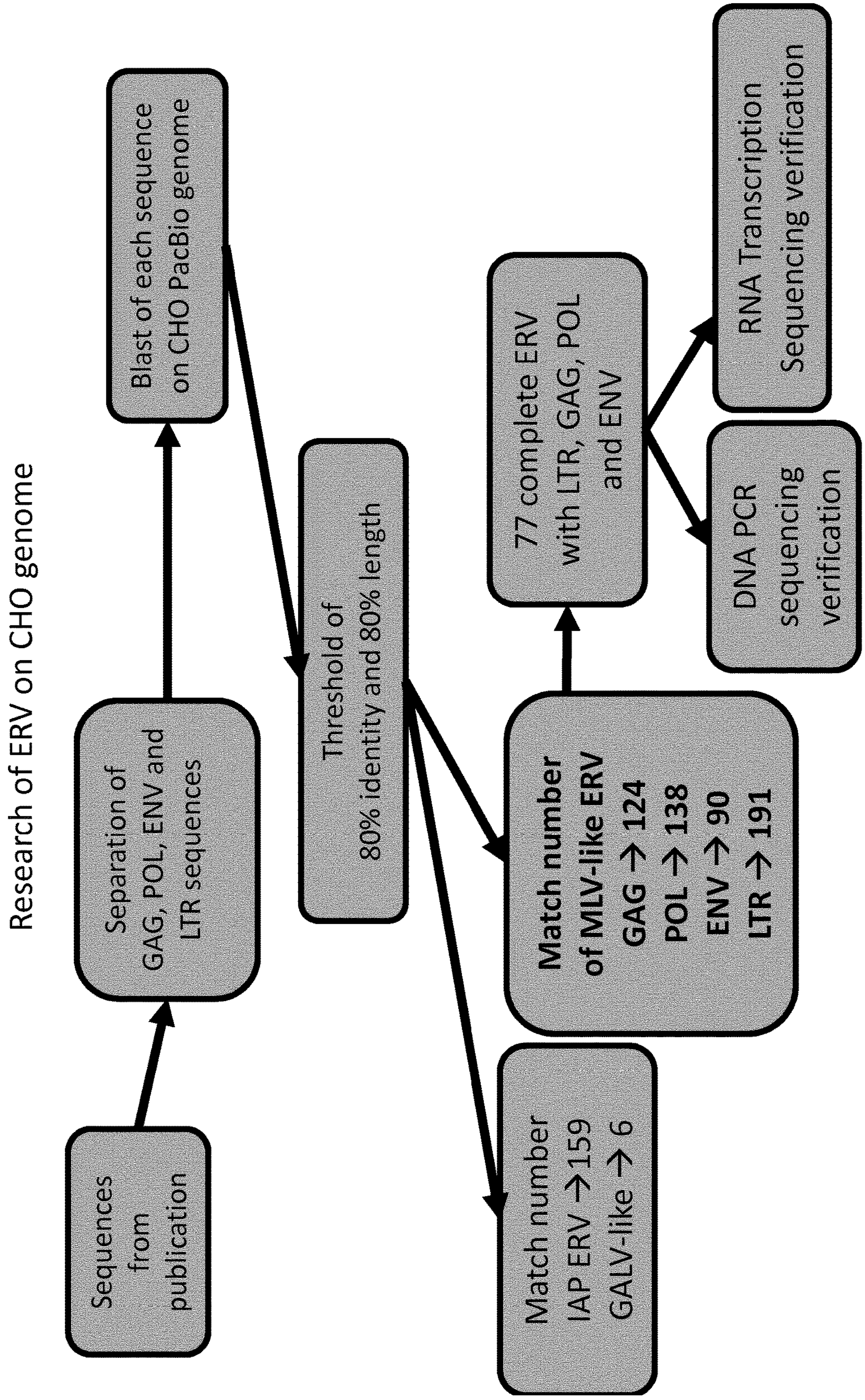
FIG. 4A shows schematically how ERV elements can be found in the genome of a cell based on a comparison of sequence of the cellular genome of the CHO-K1 cell-derived cell line termed CHO-M (from the PacBio® sequencing and genome assembly work) with sequences from typical retroviral elements (gag, pol, env, LTRs (long terminal repeats)). 77 hits were obtained from our PacBio® CHO-M cell genome. The hits were selected for further investigation and determination of consensus sequences.
Figure 4B:
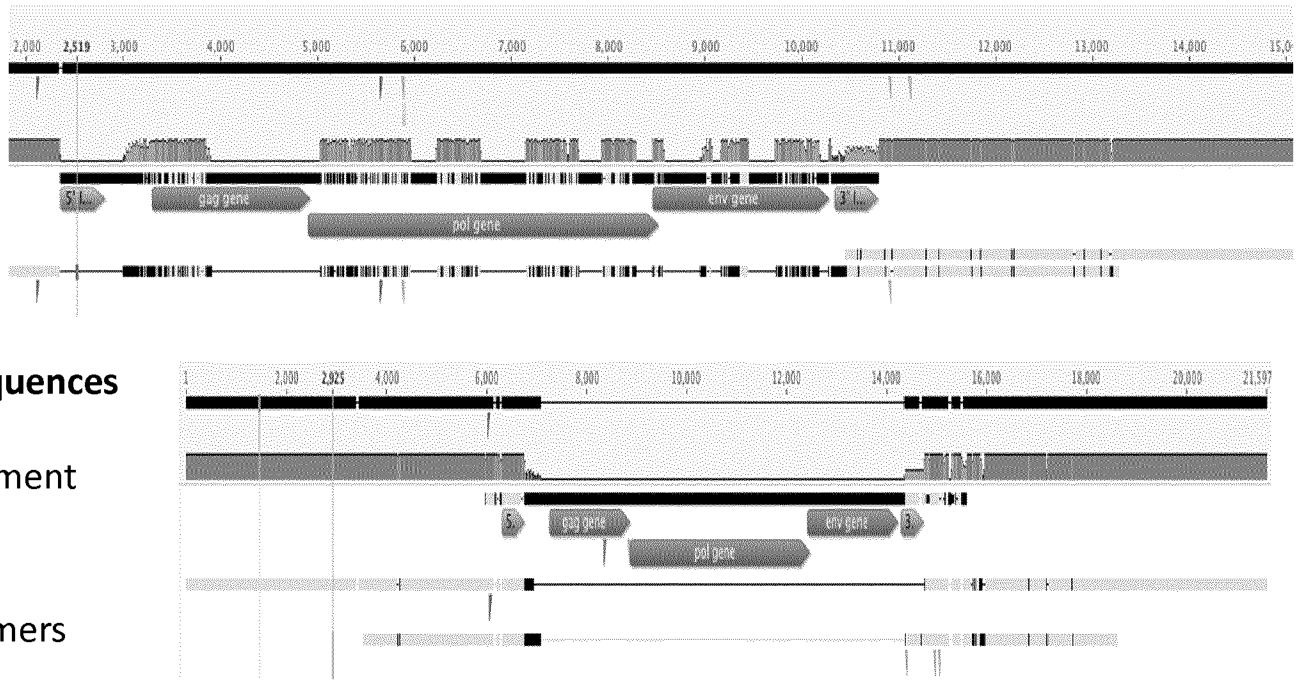
FIG. 4B shows different steps in further defining and analyzing the consensus sequences and comparisons to the published Chinese hamster genome.
Figure 4C:
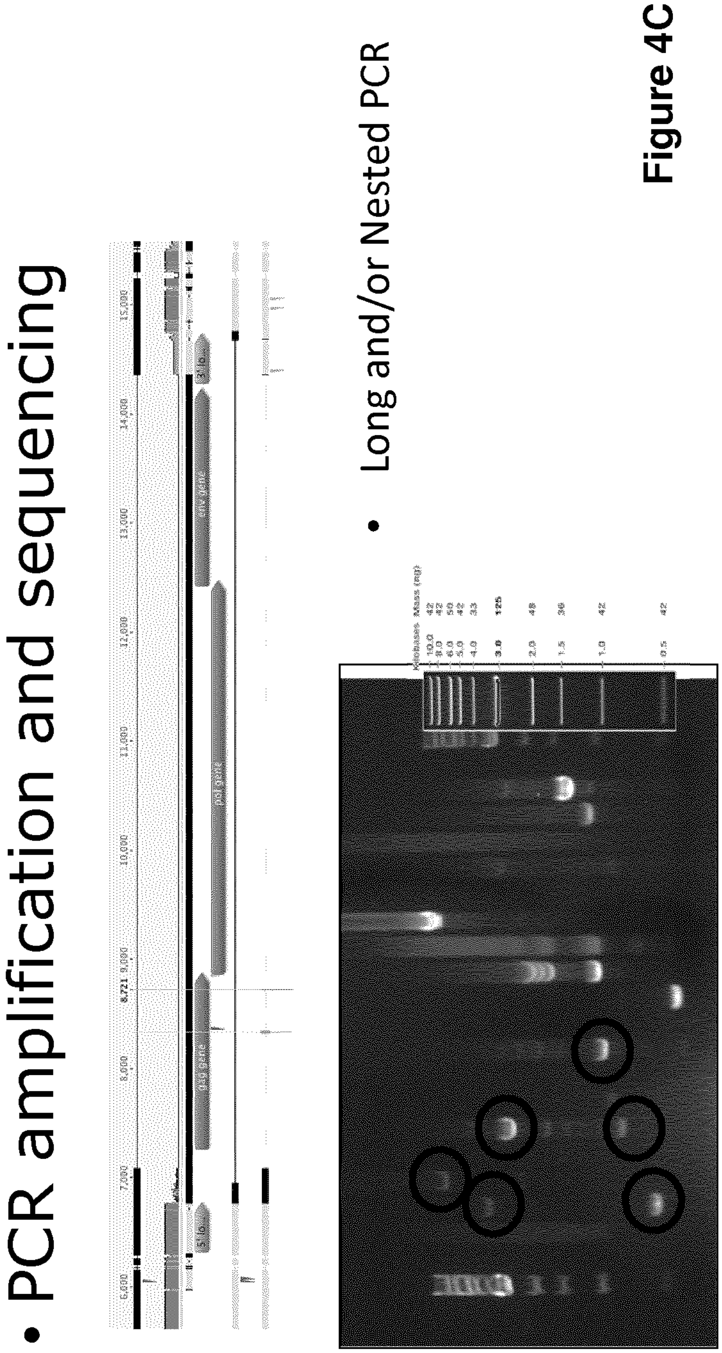
FIG. 4C shows the experimental validation of specific of gammaretrovirus ERV-like sequences identified in the CHO-M cells' genome. The validation of ERVs was performed using PCR primers hybridizing to the CHO genome sequence on either side of the predicted integrated viral genome (validation of gammaretrovirus type C sequences found using bioinformatics analyses). On a gel, the larger sequences (upper three circles) are alleles with integrated genome, while the alleles without viral integration move faster on the gel (lower three circles).
Figure 5:
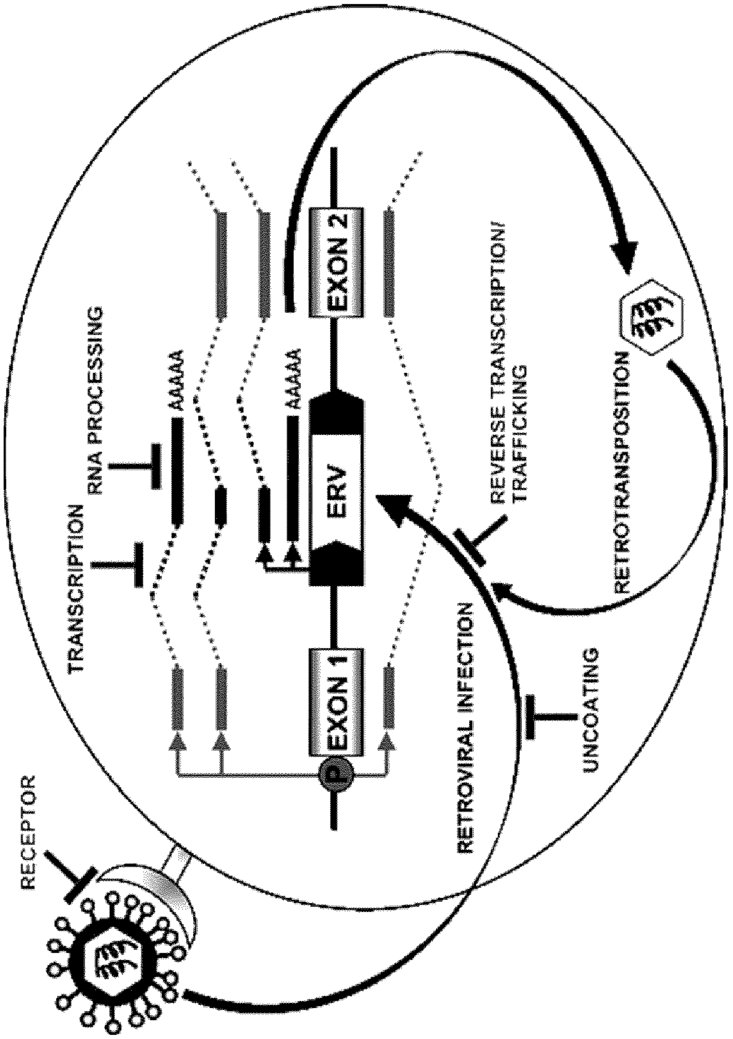
FIG. 5 shows how potentially dangerous ERVs, ergo ERVs that might be awoken, e.g. by cellular/genomic stress, can be determined. The stress can be applied at different times, in different types of cultures and/or after multiple transfections. Epigenetic data provides indications whether or not an ERV element is transcribed (epigenetic data including iRNA assessment and methylation status). During these stress periods infectious ERVs are more likely to be awoken and can be detected.

The identified sequences of ERVs included 159 members of the Intracisternal type A Particles (IAP) class II retroviruses, 144 Type C gammaretroviruses (class I ERVs), as well as 8 other gammaretroviruses, in particular GALV (see FIG. 13 for the main classes and phylogenetic relationship of these viral sequences). A typical search for a murine retrovirus type C sequence in a CHO cell is outlined in FIG. 4A.

The type C gammaretroviruses ERV sequences were further investigated and the number of ERV elements found are shown in Table A:

TABLE A

| Genes | GAG gene | Pol gene | Enveloppe | LTR |
|---|---|---|---|---|
| Extracted sequences | 124 | 138 | 98 | 191 |

After the sequences were found via alignment, primers were designed and, using these primers, the corresponding sequences were searched for experimental validation using PCR and DNA sequencing. Bordering sequences were searched for genes, specific integration marks, DNA methylation and expression, etc.

Figure 14:
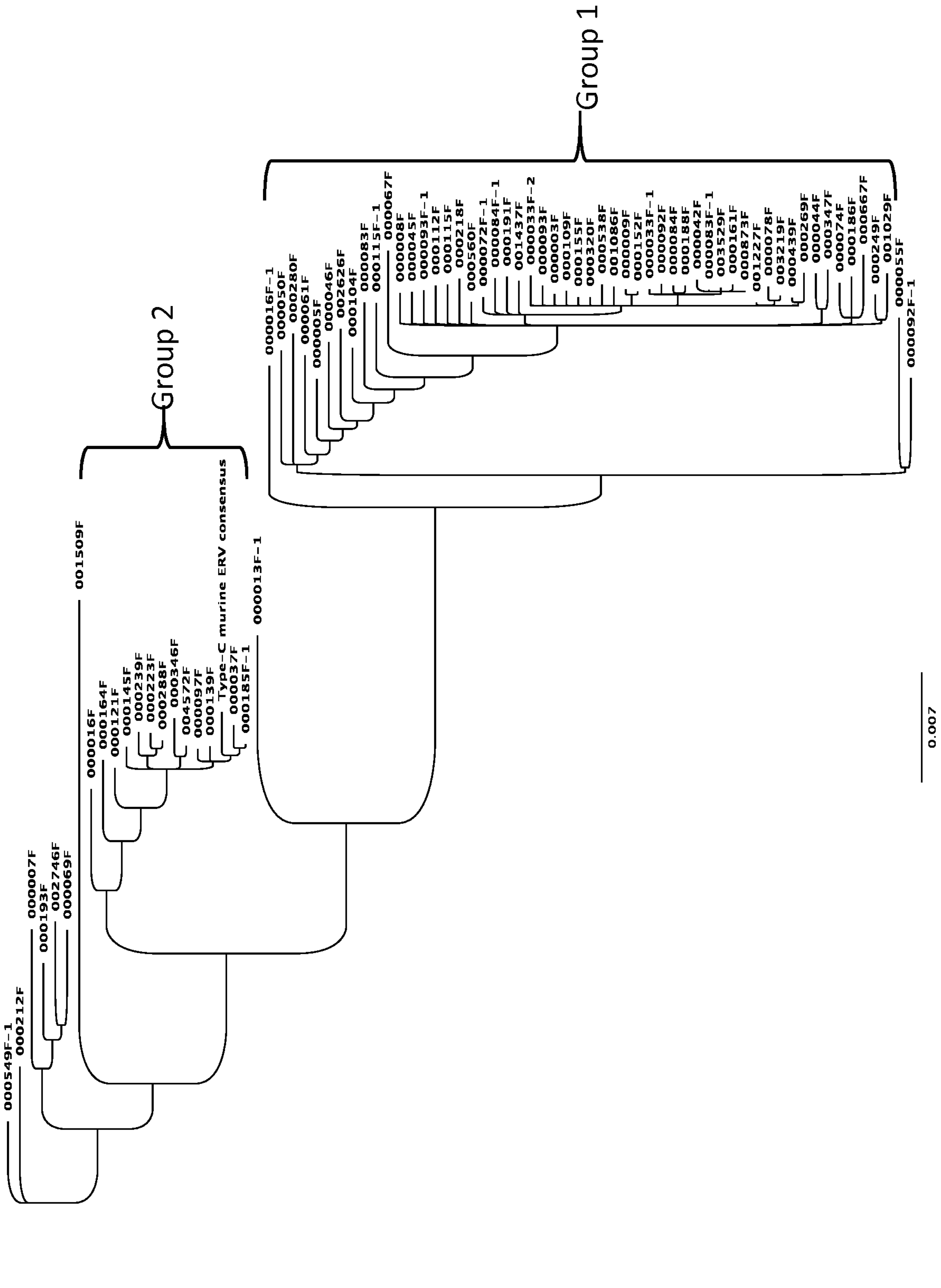
FIG. 14 shows a neighbor-joining consensus tree based on 77 GAG/POL/ENV concatenated sequences of gammaretrovisus-like ERVs from the CHO genome. Group 1 and 2 are distinguished as described elsewhere herein.
Figure 15A:
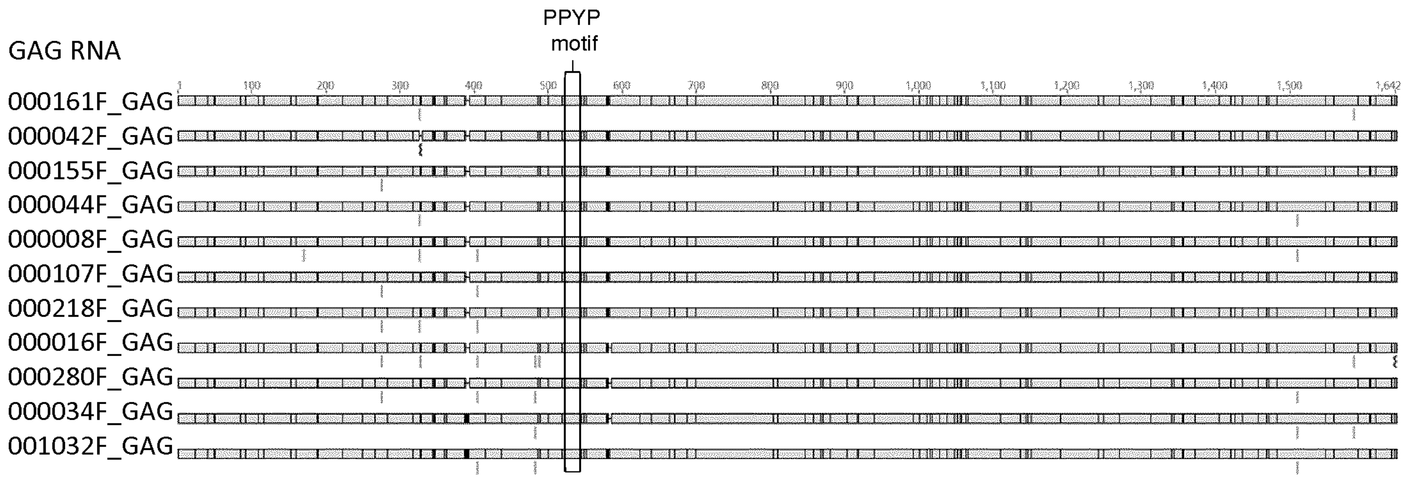
FIG. 15A shows an alignment of GAG RNAs from a selection of CHO gammaretrovirus-like ERVs transcripts characterized from CHO-M cells. The marks underneath the aligned sequences represent mutations in the GAG open reading frame. Both groups are well conserved and constitute recent integrations in Chinese hamster evolution.

Only 77 of the ERV sequences analyzed had all the elements (gag, pol, env genes) to produce an ERV. Those were further analyzed and the results are shown in FIG. 14. These 77 ERV sequences were also phylogenetically analyzed and could be divided into two groups, namely into group 1 (52) and group 2 (14) ERVs. Within these groups there was 97-99% sequence identity and between the groups there was 84-97% sequence identity. The two groups differed in their LTRs. The GAG coding sequence was well conserved. Sequence comparisons indicated that two burst of retroviral infections may have occurred relatively recently during the Chinese hamster evolution, giving rise to these well preserved and possibly functional ERVs (FIG. 15).

Furthermore, it was found that the DNA sequence encoding a PPXY-related PPYP motif important for GAG function was also present. The group 1 ERVs displayed one to twelve differences or 30 bp integrations in the genome, group 2 ERVs displayed none to 6 differences in the gag gene relative to related functional gag genes.

Investigation of Potential Expression of Identified DNA Elements

Figure 16:
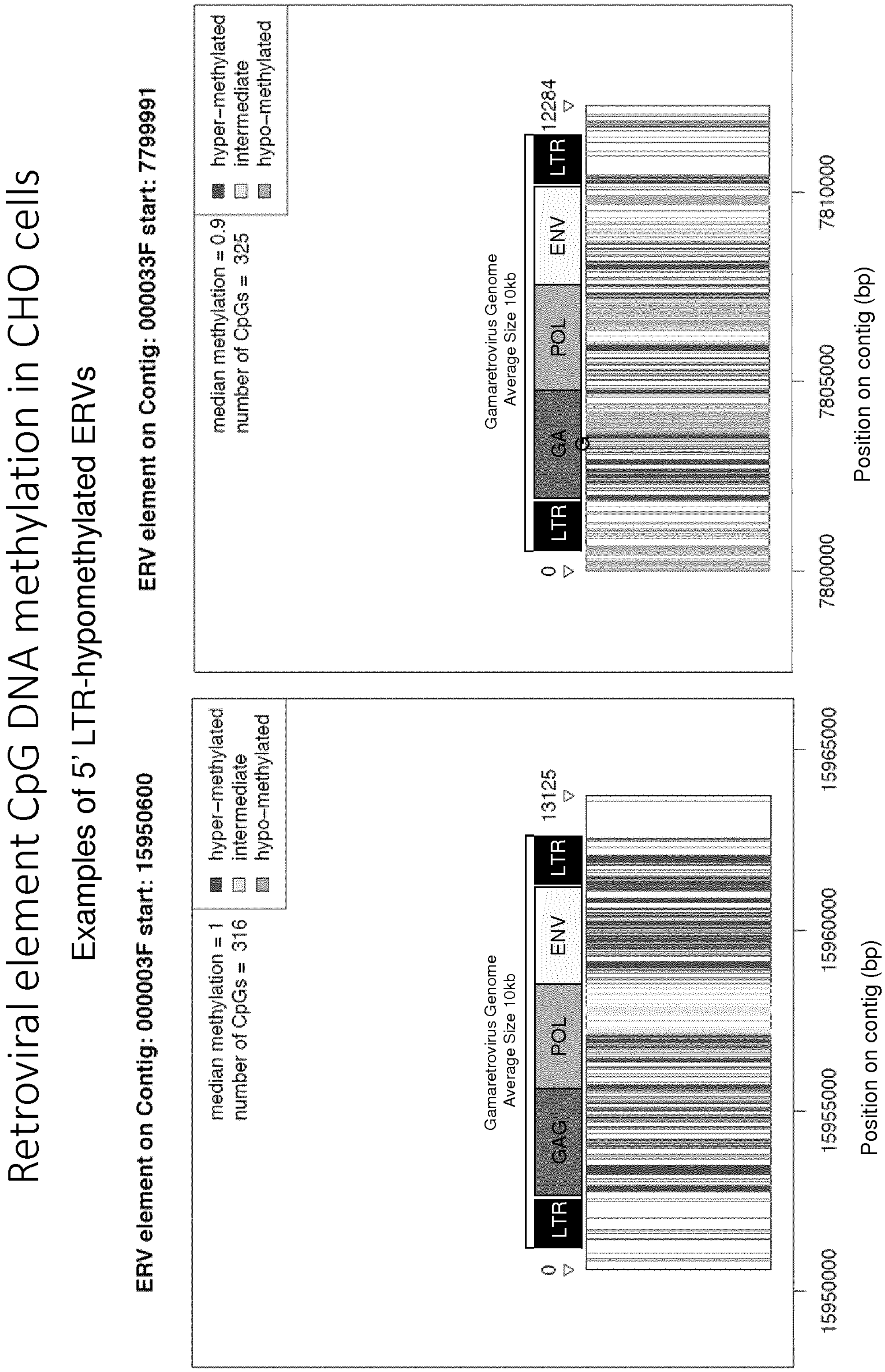
FIG. 16 shows the CpG DNA methylation status of specific ERV elements identified in the CHO-M cells. The 5'LTR ERVs are hypo-methylated in these specific examples, suggesting that they correspond to transcribed ERVs.

To assess which ERV element(s) may be transcribed, their CpG DNA methylation status was analyzed using the PACBIO sequences data (Suzuki et al., (2016)). This allowed the identification of several ERVs whose LTR sequences were hypomethylated, as expected for an expression permissive chromatin structure and transcriptionally active LTR promoter sequences, as exemplified in FIG. 16.

Construction of a RNA Database

Further sequencing and analysis of several independent mRNA preparations of the banked cell, such as a CHO-M master cells may be carried out to construct a database of RNA (i.e. cDNA) sequences that map to the genome and/or to the indicator adventitious sequence database. The product is a collection of expressed retroviral/viral, retro-transposon and bacterial marker genes and families, providing a table of the relative expression levels for each type of element.

Abundant RNA sequences that cannot be attributed to the genomic or mitochondrial genomic DNA are validated experimentally by RT-qPCR. Experimentally validated sequences are searched for possible trans-splicing events. Remaining unexplained sequences are screened for homologies to available genomes of viral, prokaryotic and eukaryotic sequences, to possibly attribute them to identified microbial species. Relevant hits are added to the database of expressed sequences.

Figure 17:
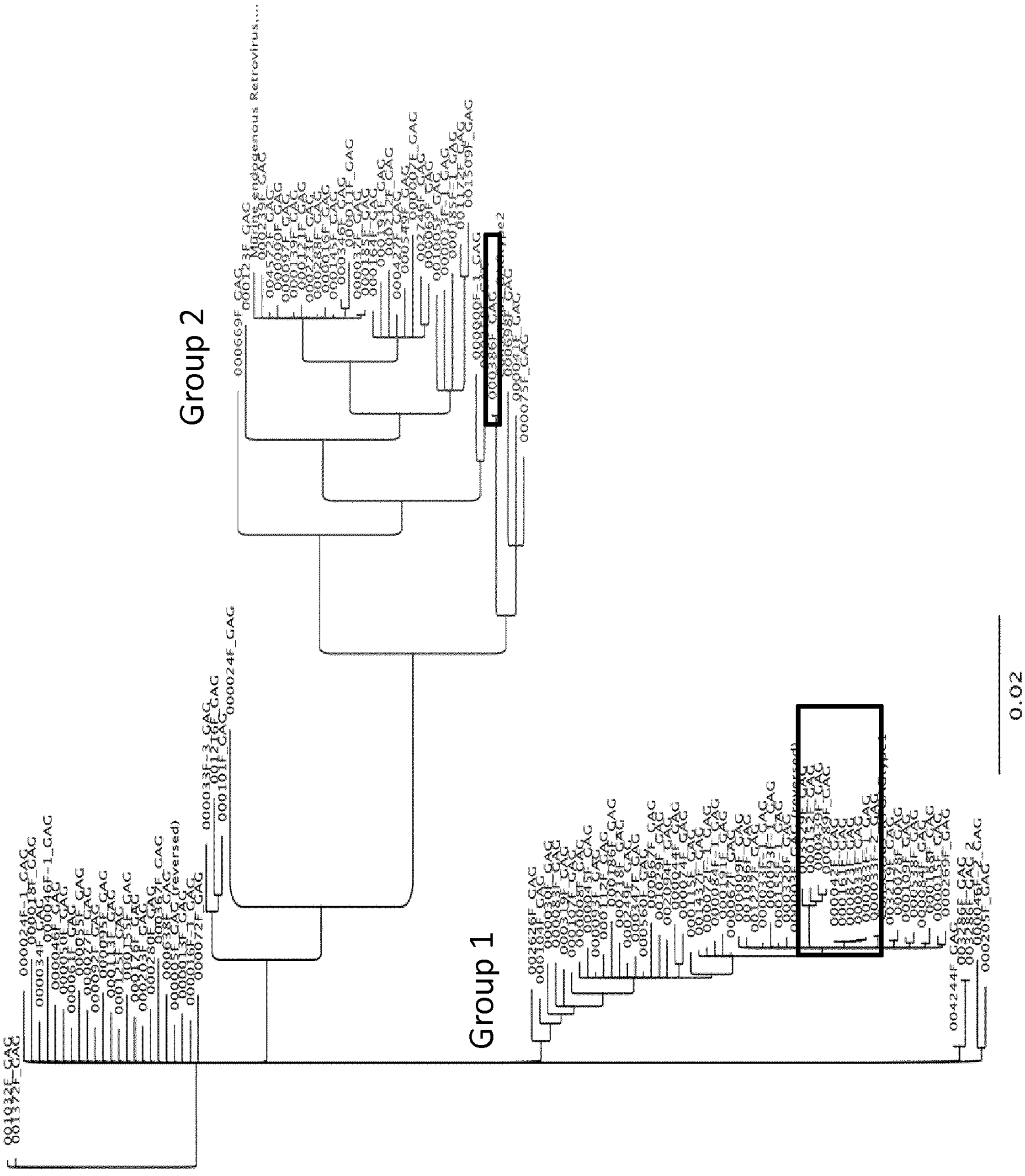
FIG. 17 shows a neighbor-joining consensus tree based on 121 GAG sequences of the gammaretrovirus-like ERV from a CHO genome. Both group 1 and 2 contain transcriptionally active ERVs. The circled sequence in group 2 was found to be active, but contained stop codons, the multiple circled sequences in group 1 were found to be active and not to contain a stop codon in the coding sequence. A Gag and Pol cDNA analysis was consistent with the existence of functional ERVs. Potentially expressed ERV are framed with a black rectangle. Based on those sequences, a consensus sequence of group 1 viruses was determined for CRISPR/Cas9 processing.

Examples of a Specific Construction of a Rna Database of Rna Expressed by Identified Dna Elements Here, the transcription of specific ERV elements was further assessed by their direct comparison with the sequence of GAG cDNAs generated using reverse transcription of the total CHO, here CHO-M cDNA, cell RNA and PCR amplification. This indicated that both group1 and 2 ERV elements were transcriptionally active. Comparisons of the genomic and cDNA sequences further indicated that one Group 2 ERV was transcribed, which however could not express a functional GAG protein due to STOP codons (FIG. 17). However, several of the identified Group 1 ERV sequences were expressed, their RNA sequence did not have premature STOP codons, and they thus appeared to mediate the expression of a functional GAG protein. Analysis of the adjacent POL coding sequences revealed that they were also functional, leading to the identification of several expressed and conserved ERVs as very strong candidates for the expression and release of retroviral particles from CHO cells. The complete consensus DNA sequence of these functional Group 1 ERVs is shown in SEQ ID NO. 1, whereas the consensus sequences of the group 2 ERVs, IAP elements and other gammaretroviral sequences identified here are provided in SEQ ID NOs, 2, 3 and 4.

Characterization of Adventitious Elements from Whole Genome/Episome Sequencing

A bioinformatics package is provided for quick identification of (i) novel mobile genetic and adventitious elements from whole genome and episome sequencing, and (ii) significant changes in the levels of expression of known microbial-like genes, as these may be indicative of the contamination of a cell culture by adventitious agents. The contaminations need to be distinguished from chromosomal rearrangements.

Here, genome comparison programs are used to devise automated processes to distinguish small genomic changes (such as transposition or viral genome integration) from large chromosomal rearrangements (such as large chromosomal translocation or duplication events) or from contamination by other cultured cells.

The parameters of the above discrimination process are determined using genomic and RNA sequences obtained from the banked cells such as CHO-M cells and from cell clones derived thereof, using clones that were previously validated for the absence of adventitious agents via conventional means.

The above process is used in conjunction with the databases obtained above, to identify potential genomic changes elicited during novel CHO cell clone isolation. Relevant hits are validated experimentally by PCR and by small scale DNA sequencing.

A similar analysis is performed using the transcriptome of, e.g., CHO-M cell clones. New RNA sequences, or RNA sequences whose expression level is significantly changed, are identified using bioinformatics analysis. The hits are validated experimentally by RT-qPCR.

The detection process is validated first in terms of sensitivity by bioinformatics modeling, followed by experimentally spiking-in CHO-M nucleic acid preparations with a known amount of a retroviral-like or bacterial (e.g. mycoplasma) sequences and with reference materials. This provides a sensitivity threshold in terms of the number of viral genome per cell genome equivalent that can be revealed following a given depth (or genome coverage) of “next-generation sequencing”.

Process for More Efficient Editing of the CHO Cell Genome and/or Transcriptome

A quantitative assay for HR and HDR targeted transgene integration and removal from the CHO cell genome via the knock-down or overexpression of proteins involved in recombinant activities is provided.

Here, several independent indicator CHO cell lines are constructed that contain a single genome-integrated GFP transgene (e.g., via transposable vectors), and transgene integration is validated by quantitative PCR and integration site mapping. An indicator plasmid is constructed by bracketing a dsRed expression cassette by sequences corresponding to the extremities of the GFP coding sequence. The frequencies of spontaneous mutation of the GFP sequence and of non-targeted integration of the dsRed expression cassette is documented relative to proper targeted integration using fluorometric and qPCR assays. Alternatively, one or several deleted GFP coding sequence is/are integrated into the cell genome, and they are repaired using HR or HDR-related mechanisms, to restore a functional GFP coding sequence and fluorescent cells The above assay is used following the transient siRNA-mediated knock-down of MMEJ and NHEJ proteins, so as to identify limiting activities that may oppose efficient HR mechanisms. A similar assay is performed in the presence of an expression vector for Cas9 and a GFP-targeted CRISPR guide RNA, to assess for HDR. In parallel, the cDNAs encoding CHO HR and HDR proteins are cloned and integrated into expression vectors. These cDNAs are co-transfected with the dsRed indicator plasmid to identify activities that limit HR or HDR efficiency in CHO-M cells.

Combinations of the above knock-down or overexpression are performed to improve the frequency of HR-like events (see FIGS. 9 to 12). The most efficient combinations are assessed and selected based on i) the results of the above assays of single activities, ii) the mRNA levels of particular recombination genes in CHO-M cells, and iii) the relative positions in the recombination pathway and multimeric structures formed by the proteins. These combinations are assayed to remove the dsRed sequence integrated into GFP, to restore a functional GFP, in order to identify a process that efficiently deletes expressed sequences from the CHO genome.

CHO-M Genetic or Epigenetic Editing to Remove Infectious Agent DNA or RNA Remnants Here, expressed viral genome remnants from CHO cell lines are removed or silenced. Viral- and retroviral-like elements expressed by CHO-M cells as determined above are targeted by HR or HDR using the optimized approach above so as to disrupt functional viral sequences, preferably gag sequences that mediate viral particle release.

Alternatively, or concomitantly, the mechanisms mediating HR or HDR are inhibited, so as to promote the repair of DSB in viral sequences by repair mechanisms that promote deletions at the DNA cleavage site, such as NHEJ and MMEJ-related mechanisms, so as to delete gag sequences that are required for the release of viral particles.

Multiple rounds of genome editing are performed, and the reduction in genomic viral and of RNA sequences will be followed by quantitative PCR. The cell division timing will be characterized after each round to ensure that additional genomic changes do not impair the metabolic properties of the cells.

Suitably engineered cells such as CHO-M cell populations are tested for their stability and ability to express marker (e.g. GFP) or therapeutic (e.g. immunoglobulins) proteins. Subclones are generated and similarly assayed. Suitable subclones are documented for the lack of possible additional adventitious agents using the detection methods described herein.

The genome sequence of the most efficient cells such as CHO-M subclones is d etermined and assembled, to document the genomic changes as well as the reduction in adventitious viral-like sequences.

Figure 6:
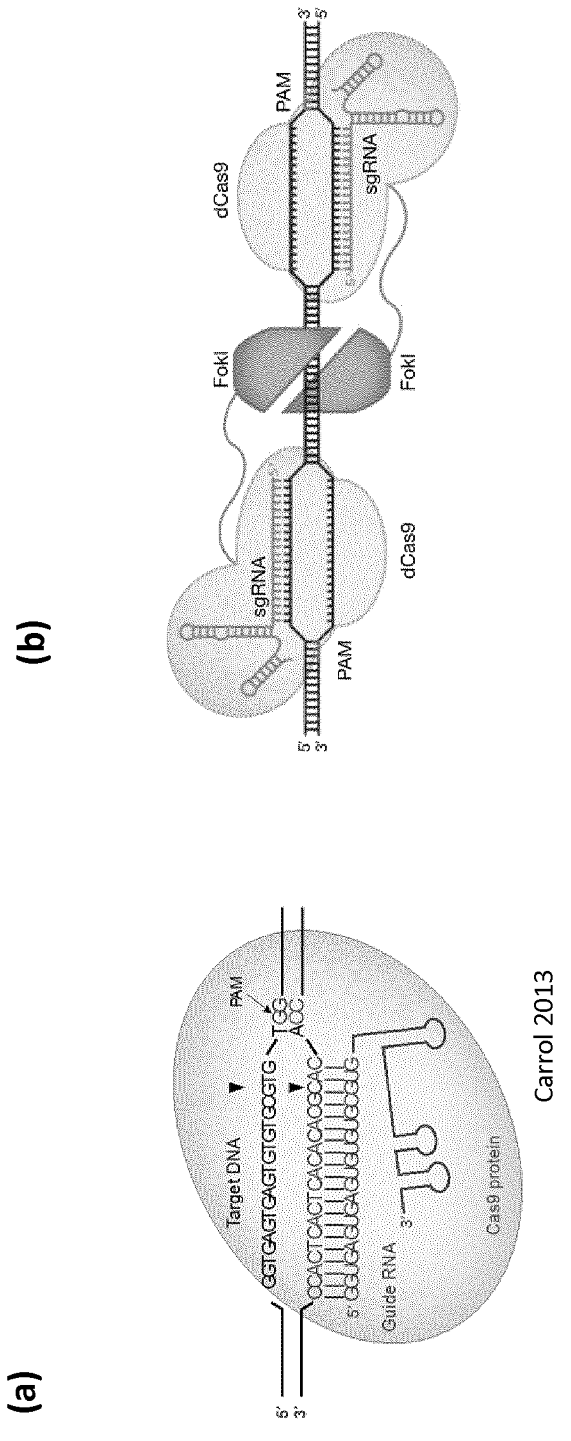
FIG. 6 shows CRISPR/Cas9 systems: using a guide RNA (also called a single guide RNA, or sgRNA), (a) system by Carrol et al. 2013 and (b) system by Guilinger et al. 2014, in which gene targeting (GT) is triggered by double stranded brakes (DSBs), illustrating that nucleases facilitate GT. Site-directed DSBs increase GT up to 10000 fold, but may also trigger unwanted off-target mutations. The nuclease activity is variable between 10-80%.
Figure 18:
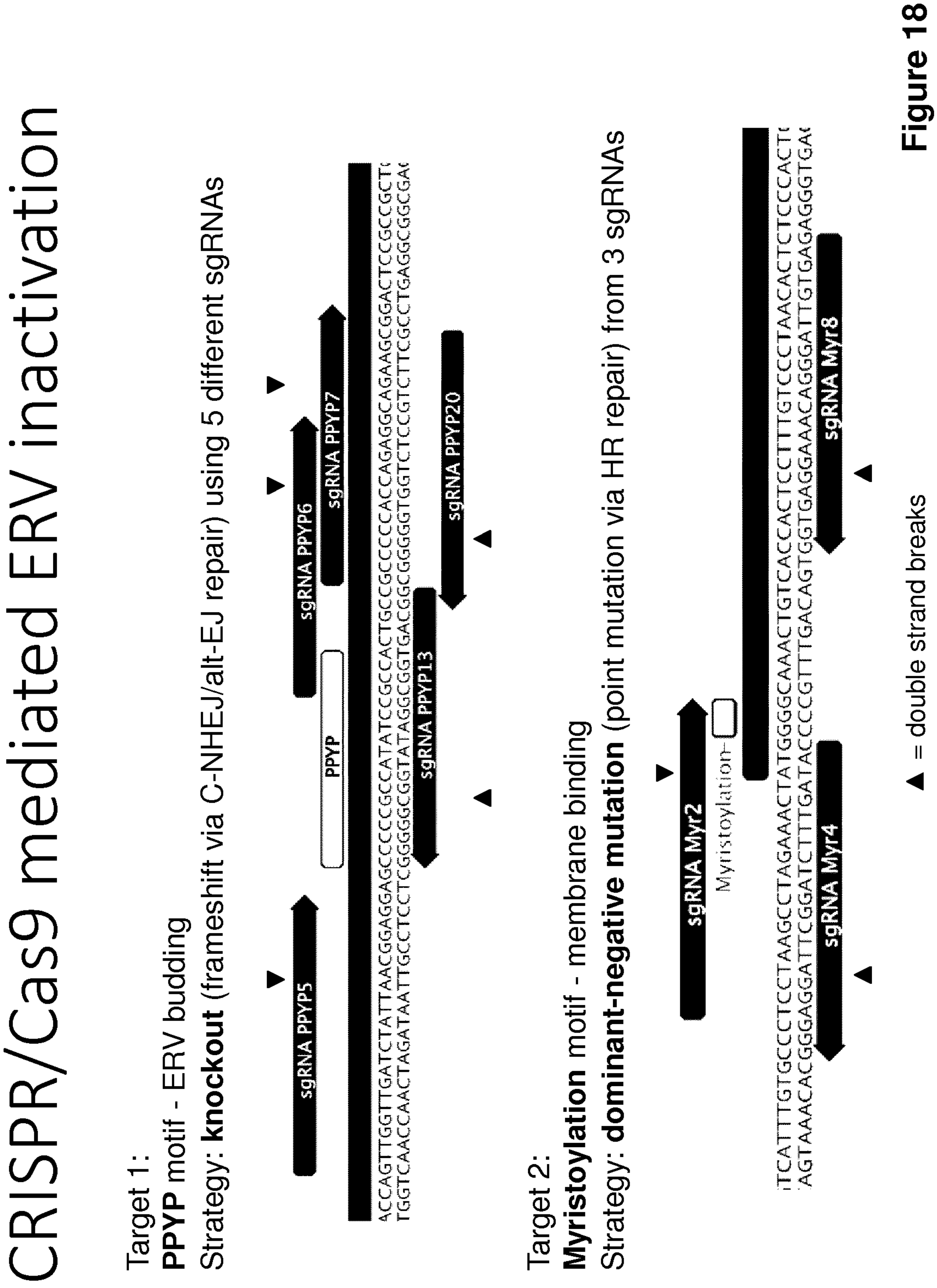
FIG. 18 shows the strategy used for CRISPR/Cas9 mediated ERV inactivation of the sequences from FIG. 17, with either the PPYP motif and the myristoylation motif as a target (both interfering with ERV budding). The arrows show where double stranded breaks were made. For sgRNA design, see Material and Methods.

In order to specifically cleave and mutate the expressed Group 1 ERVs using CRISPR/Cas9 genome edition approach, guide RNAs were designed to recognize preferentially sequences around the PPYP motif or the myristoylation sequence of the GAG sequence (FIG. 18 and SEQ ID Nos 5 to 12). The PPYP motif was chosen for a knock-out approach whereby non-HR DNA repair mechanisms may lead to deletions in the GAG coding sequence that may impair the expression of a functional version of this protein which mediates viral particle budding. The myristoylation motif was targeted to substitute the myristoylated amino acid by a non-modifiable counterpart by homology-directed HR DNA repair, so as to generate a dominant-negative version of GAG that may be both non-functional and that may inhibit the function of possibly remaining unmutated GAG proteins, as based on the known requirement for HIV1 GAG protein myristoylation for HIV budding (Abdusetir Cerfoglio et al. (2014)). The single guide RNAs (sgRNA) were designed to fit the monomeric version of CRIPR/Cas9, as illustrated in FIG. 6 (Carrol 2013).

Figure 19:
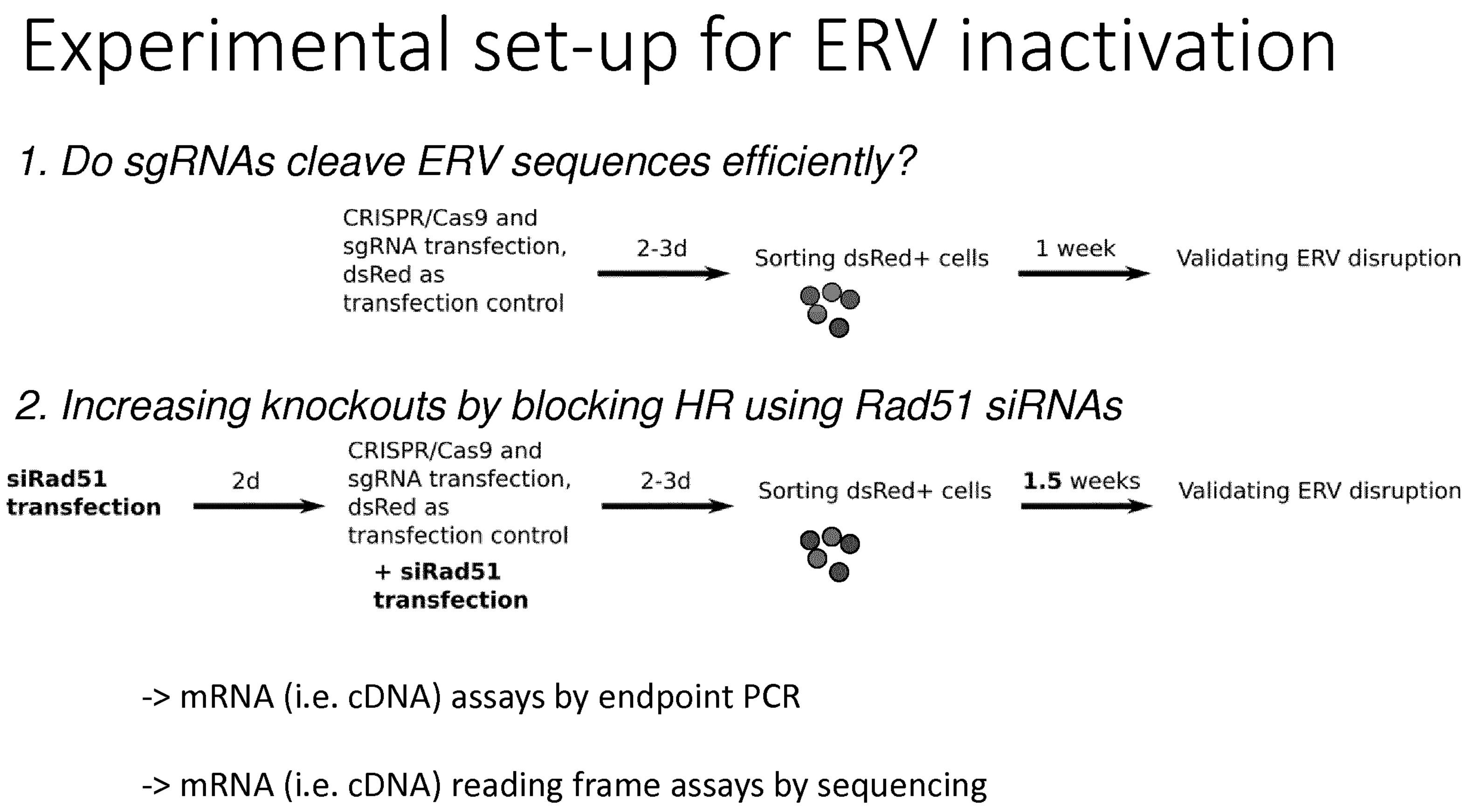
FIG. 19 shows two experimental set-ups for ERV inactivation, one without and one with inhibition of HDR repair pathways, here via Rad51 siRNA. ERV disruption is validated via mRNA (i.e. cDNA), as assayed by endpoint PCR, or by sequencing to determine the reading frame.
Figure 20:
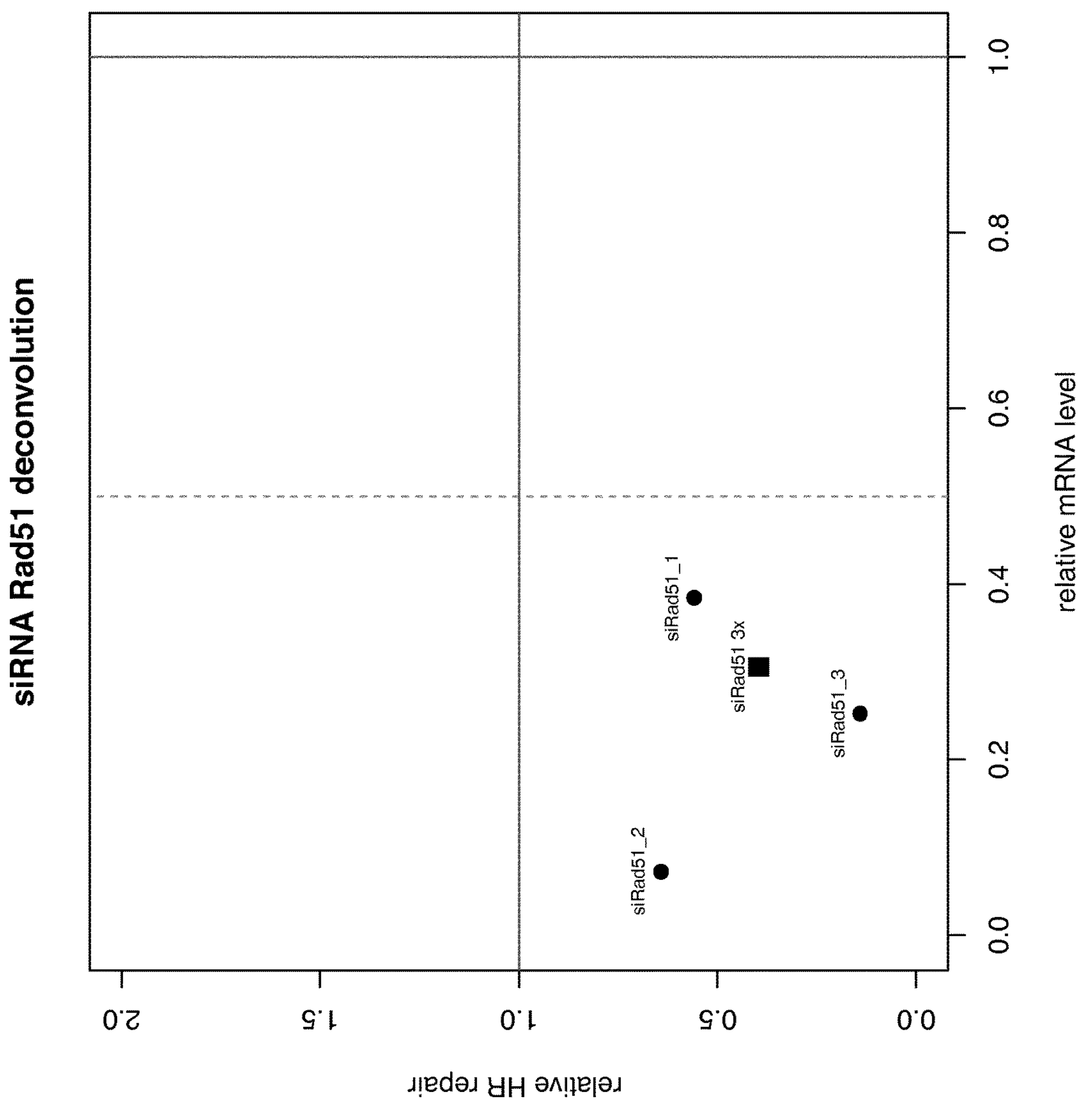
FIG. 20 shows the effect of the transfection of three individual Rad51-targeting siRNAs on the Rad51 mRNA level and on the homologous recombination repair activity relative to the levels of cells treated with non-specific negative-control siRNAs. Square: Effect of the transfection of the mix (siRad51 3x) of the three Rad51-targeting siRNAs on the Rad51 mRNA level (x-axis) and on the homologous recombination repair activity (y-axis), relative to the levels of cells treated with non-specific negative-control siRNAs which was set to a value of 1. Closed circles: similar assays performed with each of the three siRNA used individually (siRad51_1, siRad51_2, siRad51_3), to demonstrate similar effects on Rad51 and HR inhibition as the mix of the three siRNAs. As can be seen, Rad51 siRNAs are efficient and specific.

The Cas9 and sgRNAs expression vectors were co-transfected with a dsRed expression vector into CHO cells, and dsRed-expressing cells were sorted in order to enrich for the efficiently transfected and transgene-expressing cells (FIG. 19). Alternatively, the cells were transfected with a mix of three Rad51-targeting siRNAs, in order to decrease Rad51 expression and to reduce DNA repair by homologous recombination mechanisms. The efficiency of the Rad51 knock-down was assessed both at the Rad51 mRNA levels and by the inhibition of the restoration of the function of a mutated GFP transgene by homologous recombination repair, indicating that all designed siRNAs specifically inhibited Rad51 expression and HR (FIG. 20).

To directly assess whether the CRISPR/Cas9 treatment had properly targeted the expressed ERVs, the GAG RNA was reverse transcribed and PCR amplified. While GAG RNA was readily detectable from control cells, as expected, the cells treated with the PPYP5 sgRNA Cas9 consistently yielded low or undetectable levels in independent transfection experiments ($1^{st}$ and $2^{nd}$ CRISPR experiments of FIG. 21). As treatments with the PPYP6 and PPYP13-programed Cas9 did not significantly alter the GAG RNA levels when used alone, it was assessed whether the siRNA-mediated knock-down of Rad51 activity may increase the effect of these CRISPR/Cas9 treatment, as may be expected if this would prevent efficient repair of the cleaved gag genes by the HR mechanisms and thus may lead to deletion prone alternative DNA repair pathway. This was observed to be the case, as a prior knock-down of Rad51 yielded the disappearance of the GAG mRNA signal upon PPYP6 or PPYP13 and Cas9 treatment ($3^{rd}$ CRISPR experiments of FIG. 21).

Previous attempts to mutate genes using the CRISPR/Cas or other nuclease-based mutagenic systems have not led to the disappearance of the encoded mRNA even for low copy genes. In the case of high copy number ERVs, which include ERVs present in the cell in copy numbers of more than 30, 40, or even 50, as found in mammalian genomes, it was expected to be even more difficult. Thus, it was quite surprising to observe that the retroviral RNAs were undetectable in cells treated with the PPYP5 sgRNA Cas9 nuclease ($1^{st}$ CRISPR experiments of FIG. 21). A previous attempt to delete or mutate the POL gene of 62 related endogenous retroviral elements could not achieve their removal from pig cells using transient transfections, leading to the stable expression of CRISPR/CAS9 elements using transposable or viral vectors (Yang L. et al., 2015). Even so, the continuous activity of CRISPR/Cas for 17 days only led to a maximum targeting frequency of 37% of the cells, possibly because prolonged activity of CRISPR/CAS led to toxic off-target cleavage effects.

The experiments performed show that the knock-down of HR proteins such as Rad51 can be used to increase the frequency of GAG gene inactivation by deleterious deletions at a frequency not seen without transfecting the siRNA.

While the knock-down of Rad51 is provided as an example, someone skilled in the art will understand that the knock-down of other HR proteins will have comparable results.

Accordingly, CHO cells having other HR proteins knocked-down are within the scope of the present invention. But also cells having 53BP1, CtIP, Mre11, Rad50, Ligase III, Pold3 (DNA polymerase delta subunit 3), Xpf and Blm (Bloom syndrome RecQ like helicase) knocked-down (see FIG. 9) are specifically included in the present invention. Table C provides examples of HR proteins that may be knocked-down as well as proteins of other recombinant pathways that might be knocked-down or overexpressed. However, as the person skilled in the art will appreciate Table C is a simplification: Some of the proteins mentioned in Table C have dual function (e.g., Ligase III) and could be listed in different categories.

Without being limited to any particular theory, Cas9-cleaved ERVs may be repaired by homologous recombination taking one of the many other ERVs as a homologous template, which may be inhibited by the inactivation of homology-based pathway proteins such as Rad51. In contrast, some previous attempts to knock-down Rad51 expression prior to the expression of the CRISPR/Cas9 components has led to the increase of homology-directed DNA repair pathways, which must rather be avoided when deletions leading to gene inactivation are to be favored (Davis, L., and Maizels, N. 2014 and 2016). Other studies have found that Rad51 overexpression can increase homology-directed DNA repair in targeted gene integration (i.e. knock-in) studies following CRISPR/Cas9- or TALEN-mediated DNA cleavage (Song J et al (2016)). Here, it was shown that RAD51 favors HDR gene correction in various types of CHO cells (FIGS. 9 and 12), and that the inhibition of homologous recombination activities can greatly increase the mutation of ERV, when used in conjunction with an ERV-specific DNA nuclease. Thus, when multiple alleles are to be inactivated, ergo in case of high copy number ERVs, an embodiment is often preferred that combines siRNA knock-down, in particular of the HR pathway, in conjunction with, in particular CRISPR/Cas9 approach over the use of CRISPR/Cas9 alone, which is another embodiment of the present invention.

Overall, the very high mutagenic activity of CRISPR/Cas9 components is surprisingly elevated when compared to the state of the art. Without being limited to any particular theory, the reason may be that Cas9 nuclease specifically targets expressed ERV rather than inactive ones. However, this is unlikely to explain the reduction of the viral RNAs to undetectable levels in the most efficient settings. Thus, it may also be that specific DNA cleavage events can lead to the transcriptional silencing of expressed ERVs.

Figure 21:
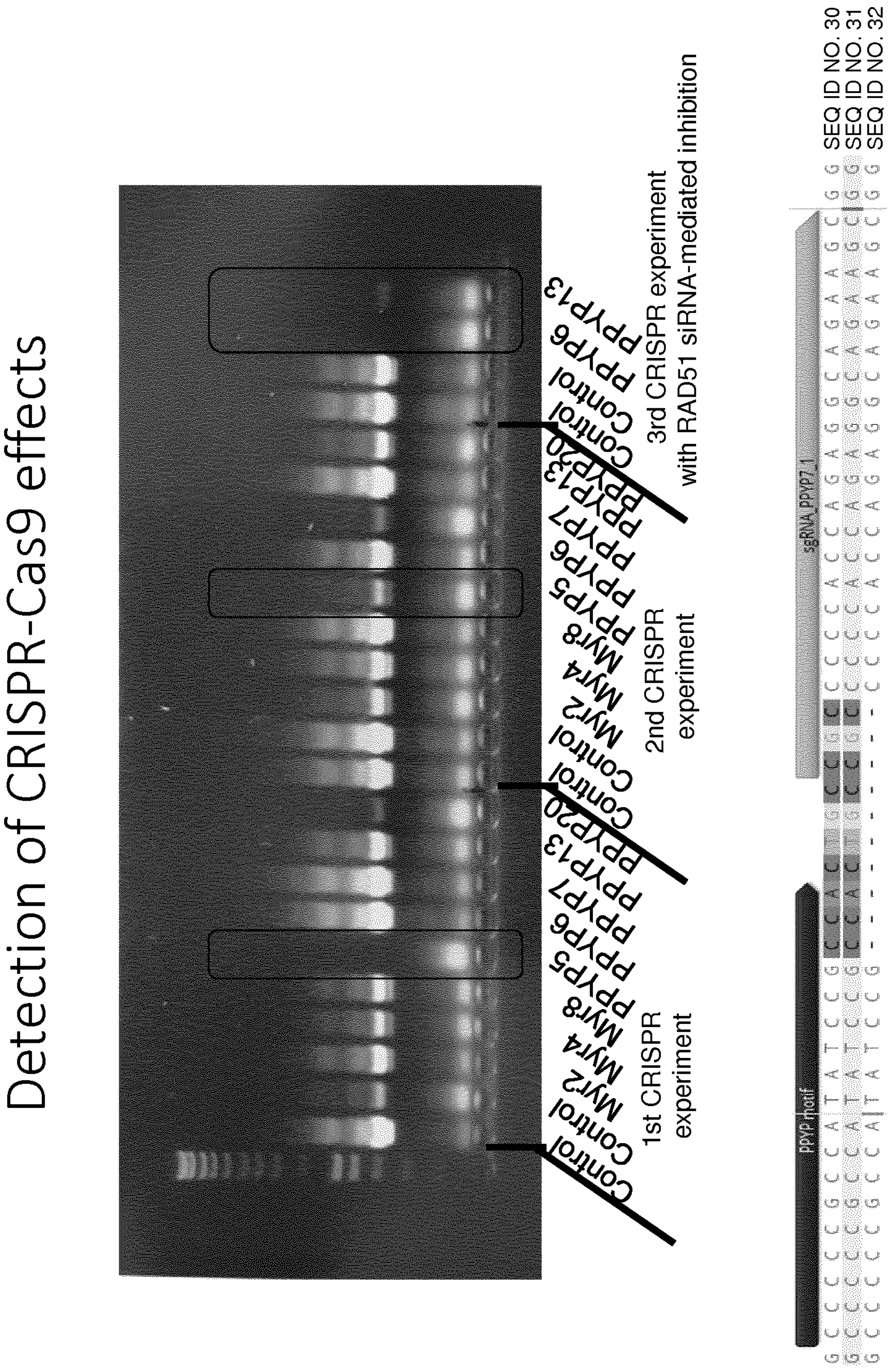
FIG. 21 shows effects of CRISPR-Cas9 when used in conjunction to specific sgRNAs in a cDNA PCR assay, which shows reduced ERV expression with ERV-specific primers: The first and second CRISPR experiments show reproducibility and the third one shows the effect of an additional RAD51 siRNA mediated inhibition prior to the CRISPR-Cas9 treatment. Strong ERV mRNA signal losses with PPYP5 sgRNA as well as with RAD51 knockdowns were observed (gel on the top). In the graph at the bottom, the ERV group 1 consensus sequence is shown at the top (SEQ ID NO. 30), a control (untreated cells) Group 1 PPYP motif sequence is shown in the middle (SEQ ID NO. 31) and an example of an out-of-frame deletion obtained from PPYP7 sgRNA treated cells is shown at the bottom (SEQ ID NO. 32).

Finally, non-coding mutated RNAs bearing premature stop codons are often degraded intracellularly by the non-sense-mediated RNA decay (NMD) mechanism (Baker and Parker (2004). Thus, it was next assessed whether the PPYP sgRNA may mediate out of frame mutations that could lead to the NMD-mediated degradation of the GAG RNA. Such a frame shift mutation, generated by the deletion of 11 nucleotides from the PPYP motif of a group 1 ERV, is shown in FIG. 21 as an example.

Figure 22:
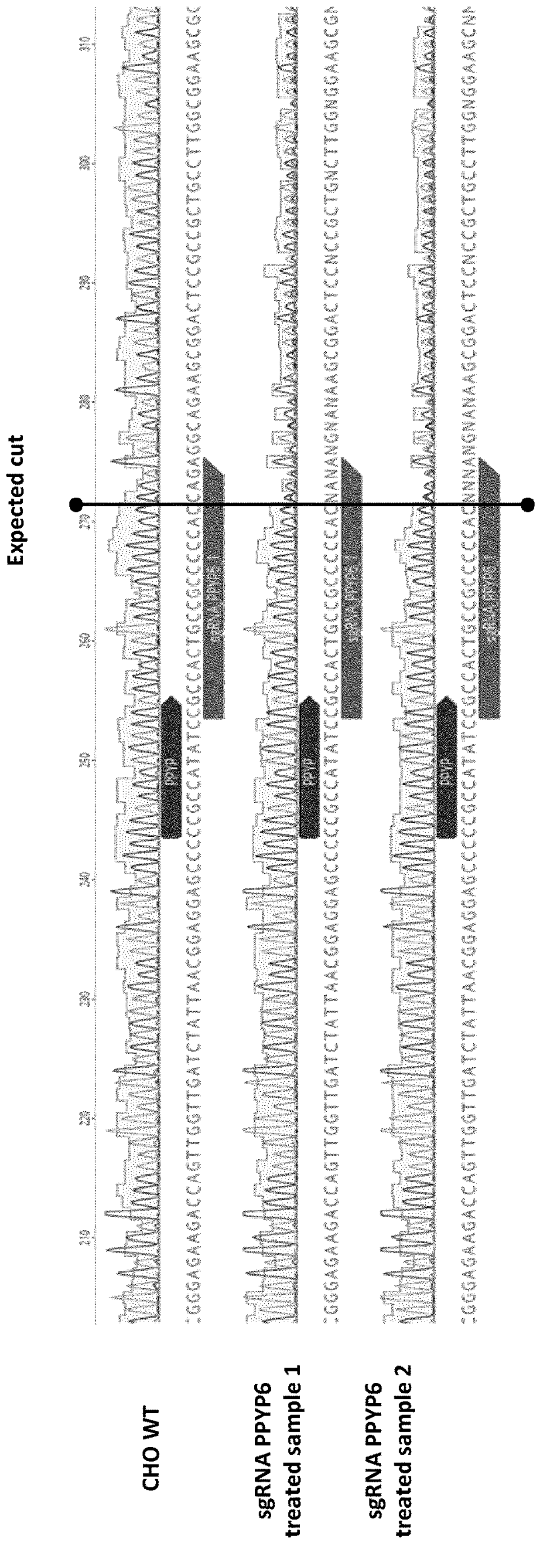
FIG. 22 shows the sequencing electropherograms of amplified GAG ERV sequences, from untreated CHO cells (CHO WT), or from CHO cells treated with the PPYP6 sgRNA-programed Cas9 nuclease, as obtained from the first CRISPR experiment (sample 1) and the second (sample 2) CRISPR experiment, as depicted in FIG. 21. The Cas9 cleavage site is indicated by the vertical line, after which a mixture of sequences is observed for the treated cells, showing that 50% or more of the GAG sequences were mutated.

FIG. 22 shows the result of the PCR amplification and sequencing of the GAG genes contained in the polyclonal population of CRISPR/Cas-treated CHO cells. The results clearly indicate that a majority of the GAG coding sequences were mutated following a transient transfection of expression vectors for the CRISPR/Cas9 nuclease components, even when using the moderately active PPYP6 sgRNA and the absence of the siRAD51 treatment.

Overall, it was concluded that the proposed CRISPR/Cas9 approach targeting CHO cell endogenous ERVs can be used to eradicate or decrease the expression of the GAG protein that mediates viral particle release, and this without the need of prolonged CRISPR/Cas expression or the stable integration of their expression vectors into the cell genome, and of their potential negative effects upon cell culture. This approach can thus be used to generate safer CHO cells lines that are not able to express such retroviral proteins.

Material and Methods

Cell Line

The edited cell line was the SURE CHO-M cell line™ (SELEXIS SA, Switzerland), (see: U.S. Pat. Nos. 7,129,062 and 8,252,917, and published application numbers 20110061117, 20120231449 and 20130143264, the disclosures of which are incorporated herein by reference).

CRISPR/Cas9 System

For genome editing we used the mammalian codon-optimized *Streptococcus pyogenes* Cas9 nuclease. Single guide RNA (sgRNA) sequences were cloned into the mammalian gRNA expression vector MLM3636 as previously described (Fu et al, 2013). To achieve high knockout efficiencies, several sgRNA target sites per target site were tested (PPYP: n=5; Myr: n=3). The CRISPRseek R package (Zhu et al., 2014) was used to identify ERV specific sgRNAs with minimal off-target sites using our private CHO-M genome as reference sequence. sgRNA sequences were designed to hybridize to the vicinity of the target sites, more precisely the Myr and PPYP motifs, to maximize the CRISPR/Cas9 mutagenesis potential for these loci. All possible sgRNA sequences were retrieved using the CRISPRseek R package (Zhu et al., 2014) that contain a 5' 20nt NGG 3' sequence structure and that mediate a DSB not more than 25 bp apart from the mutagenesis site. Among all potential sgRNA sequences, the sgRNA efficiencies were predicted using various scoring tools, including CRISPRseek (Zhu et al., 2014), Sequence Scan for CRISPR (SSC; Dana Faber Institute crispr website) and sgRNA scorer 1.0 (Dana Faber Institute crispr website). Furthermore, the CRISPRseek R package (Zhu et al., 2014) was used to identify ERV specific sgRNAs with minimal off-target sites using our private CHO-M genome as reference genome. Several sgRNA sequences per target site were finally selected and tested (Myr: n=3, PPYP: n=5), to identify sgRNAs with maximal mutation potential. Cas9 (#43861) and gRNA expression plasmids (#43860) are available from ADDGENE (Cambridge, Mass., USA).

TABLE B lists a number of example sgRNAs

| sgRNA | Target sequence (5'-3') with PAM underlined; addition of non-targeting G to improve U6 expression (in lowercase) | Orientation |
|---|---|---|
| Myr2 (Seq ID No. 5) | gTCCTAAGCCTAGAAACTATGGGG | Forward strand |
| Myr4 (Seq ID No. 6) | gCATAGTTTCTAGGCTTAGGAGGG | Reverse strand |
| Myr8 (Seq ID No. 7) | GAGTGTTAGGGACAAAGGAGTGG | Reverse strand |
| PPYP5 (Seq ID No. 8) | GTTGGTTGATCTATTAACGGAGG | Forward strand |
| PPYP6 (Seq ID No. 9) | GCCACTGCCGCCCCCACCAGAGG | Forward strand |
| PPYP7 (Seq ID No. 10) | GCCCCCACCAGAGGCAGAAGCGG | Forward strand |
| PPYP13 (Seq ID No. 11) | GGCAGTGGCGGATATGGCGGGGG | Reverse strand |
| PPYP20 (Seq ID No. 12) | GCTTCTGCCTCTGGTGGGGGCGG | Reverse strand |

RNA Interference

Small interfering RNA (siRNA) against the Rad51 CHO homologous were designed and synthesized by MICROSYNTH AG (Balgach, Switzerland). Rad51 mRNA levels were silenced using a mixture of three specific Rad51 siRNA to minimize off-target effects. BLAST analysis excluded homology to other targets. A mixture of three non-targeting siRNAs (siNeg) was used as control.

Modifications of CHO-M Genome

CHO-M cells were transfected using the Neon Transfection System® (INVITROGEN) according to the manufacture's protocol. Briefly, 400,000 cells were transfected with 100 nM siRNA mixture and 48 h later, 700,000 cells were re-transfected with the CRISPR/Cas9 system using a dsRed encoding plasmid as transfection control. To enrich for transfected cells, around 100,000 dsRed positive cells were polyclonaly sorted 48-72h after transfection using flow cytometry.

As the person skilled in the art will appreciate, the above description is not limiting, but provides examples of certain embodiments of the present invention. With the guidance provided above, the person skilled in the art is able to devise a wide variety of alternatives not specifically set forth herein.

TABLE C lists some of the key genes in each of the three pathways, (see also US Patent Publication 20120231449, which is incorporated herein by reference in its entirety). Also included in the table are DNA repair proteins such as MDC1 and MHS2. MDC1 is required to activate the intra-S phase and G2/M phase cell cycle checkpoints in response to DNA damage. However, MDC1 also functions in Rad51-mediated homologous recombination by retaining Rad51 in chromatin. (For sequences see. WO 2014/118619, U.S. Patent Publication 20150361451, which is incorporated herein by reference in its entirety)

SELECTED GENES OF CERTAIN RECOMBINATION PATHWAYS

| Recombination pathway | gene | Full name of gene |
|---|---|---|
| NHEJ | Xrcc4 | X-ray repair complementing defective repair in Chinese hamster cells 4 |
| | Ku70 | X-Ray Repair Complementing Defective Repair In Chinese Hamster Cells 6 |
| | Ku80 | X-ray repair complementing defective repair in Chinese hamster cells 5 (double-strand-break rejoining) |
| | LigIV | Ligase IV, DNA, ATP-Dependent |
| | DNA-PKcs | Protein Kinase, DNA-Activated, Catalytic Polypeptide |
| | 53BP1 | Tumor suppressor p53-binding protein 1 |
| HR | Rad51 | RAD51 recombinase // DNA repair protein RAD51 |
| | Rad51B | RAD51 paralog B // DNA repair protein RAD51 homolog 2 |
| | Rad51C | RAD51 paralog C // DNA repair protein RAD51 homolog 3 |
| | Rad51D | RAD51 paralog D // DNA repair protein RAD51 homolog 4 |
| | Rad52 | RAD52 // DNA repair protein RAD52 |
| | Rad54 | RAD54 // DNA repair and recombination protein RAD54 |
| | Xrcc2 | X-ray repair complementing defective repair in Chinese hamster cells 2 // DNA repair protein XRCC2 |
| | Xrcc3 | X-ray repair complementing defective repair in Chinese hamster cells 3 // DNA repair protein XRCC3 |
| | Brca1 | breast cancer 1, early onset // breast cancer type 1 susceptibility protein |
| | Brca2 | breast cancer 2, early onset // breast cancer type 2 susceptibility protein |
| | Cyclin D1 | Cyclin D1 |
| | Bard1 | BRCA1 associated RING domain 1 // BRCA1 associated RING domain 1 |
| MRN | Mre11 | Mre11 = meiotic recombination 11 // Double-strand break repair protein MRE11 |
| | Rad50 | RAD50 Homolog (*S. Cerevisiae*) |
| | Nbs1 | Nibrin |
| MMEJ | Ercc1 | excision repair cross-complementing rodent repair deficiency, complementation group 1 // DNA excision repair protein ERCC-1 |
| | Xpf | excision repair cross-complementing rodent repair deficiency, complementation group 4 |
| | Pol theta | Polymerase (DNA directed), theta |
| | Ligase I | DNA ligase 1 // DNA ligase 1 |
| | Ligase III | Ligase III, DNA, ATP-Dependent |
| | Xrcc1 | X-ray repair complementing defective repair in Chinese hamster cells 1 |
| | CtIP | mediator of DNA-damage checkpoint 1 // Mediator of DNA damage checkpoint protein 1 |
| | PARP1 | mediator of DNA-damage checkpoint 1 // Mediator of DNA damage checkpoint protein 1 |
| | POLD3 | |
| DNA repair proteins | MDC1 | mediator of DNA-damage checkpoint 1 // Mediator of DNA damage checkpoint protein 1 |
| | MSH2 | mutS homolog 2 |

BIBLIOGRAPHY

Abdusetir Cerfoglio et al., Structural elements in the Gag polyprotein of feline immunodeficiency virus involved in Gag self-association and assembly, *Journal of General Virology* 95, 2050-2059 (2014).

Baker, K. E.; Parker, R., Nonsense-mediated mRNA decay: Terminating erroneous gene expression". *Current Opinion in Cell Biology* 16: 293-299 (2004).

Carrol et al., Staying on target with CRISPR-Cas, *Nature Biotechnology* 31, 807-809 (2013).

Davis, L., and Maizels N., Homology-directed repair of DNA nicks via pathways distinct from canonical double-strand break repair. Proc. Natl. Acad. Sci. USA 111, E924-E932 (2014).

Davis, L., and Maizels, N., Two Distinct Pathways Support Gene Correction by Single-Stranded Donors at DNA Nicks. Cell Reports 17, 1872-1881 (2016).

Food and Drug Administration (FDA), FDA's Guidance for Industry Characterization and Qualification of Cell Substrates and Other Biological Materials Used in the Production of Viral Vaccines for Infectious Disease Indications, February 2010, available at the Fda.gov website.

Fu et al., High-frequency off-target mutagenesis induced by CRISPR-Cas nucleases in human cells. Nat. Biotechnol. 31,822-6 (2013).

Guilinger et al., Fusion of catalytically inactive Cas9 to Fokl nuclease improves the specificity of genome modification, *Nature Biotechnology* 32,577-582 (2014)

Hope & Trono, HIV, Structure, Expression, and Regulation of the HIV Genome, *Site Knowledge Base Chapter November* 2000.

International Patent Publication WO 2014/118619 (2014).

Kostyrko et al., MAR-Mediated transgene integration into permissive chromatin and increased expression by recombination pathway engineering, *Biotechnology & Bioengineering,* 3 Oct. 2016 online edition.

Lewis et al., Genomic landscapes of Chinese hamster ovary cell lines as revealed by the Cricetulus griseus draft genome, Nature Biotechnology 31,759-765 (2013), Supplement)

Lie, Y. S. et al., Chinese hamster ovary cells contain transcriptionally active full-length type C proviruses. *J. Virol.* 68:7840-7849 (1994).

Ma et al., Hairpin opening and overhang processing by an Artemis:DNA-PKcs complex in V(D)J recombination and in nonhomologous end joining. *Cell* 108, 781-794 (2002). *Song J et al., RS*-1 enhances CRISPR/Cas9- and TALEN-mediated knock-in efficiency, Nature Communications 7:10548 (2016).

Suzuki et al., Agln: measuring the landscape of CpG methylation of individual repetitive elements. *Bioinformatics* 32:2911-2919 (2016).

US Patent Publication 20120231449 (2012).

US Patent Publication 20150361451 (2015).

Yang L. et al., Genome-wide inactivation of porcine endogenous retroviruses (PERVs), Science 350:1101-1104 (2015).

Zhu et al., CRISPRseek: A Bioconductor package to identify target-specific guide RNAs for CRISPR-Cas9 genome-editing systems. *PLoS One.* 9 (2014).

What is claimed is:

1. An engineered CHO (Chinese Hamster Ovary) cell comprising:

a genome of the CHO cell, wherein the genome comprises endogenous retrovirus (ERV) elements comprising sequences encoding a Gag protein wherein the sequences encoding the Gag protein comprise:

SEQ ID No: 30, or a sequence having more than 90% sequence identity with SEQ ID No: 30, wherein the SEQ ID No: 30 or the sequence having more than 90% sequence identity with SEQ ID No: 30 is altered to comprise at least one deletion, at least one addition, at least one substitution or combinations thereof resulting in an altered sequence, wherein the ERV elements comprising the altered sequence do not encode a functional Gag protein.

2. The engineered cell of claim 1, wherein the ERV elements are gammaretroviral ERVs, including Chinese hamster gammaretroviral, Koala epidemic viral (KoRV), Mouse Mammary Tumor Viral (MMTV), Mouse Leukemia Viral (MLV) ERVs and wherein said altered sequences are adapted to suppress or eliminate release of more than 60%, more than 70%, more than 80%, more than 90%, more than 95% or of 100% of said ERVs.

3. The engineered cell of claim 1, wherein said deletions, additions or substitutions comprise more than 2, 3, 4, 5, 10, 15, 20, 25, 30, 40, or 45 nucleic acids.

4. The engineered cell of claim 1, wherein the SEQ ID No: 30 or the sequence having more than 90% sequence identity with SEQ ID No: 30 are altered to comprise is an addition in form of a targeted integration.

5. The engineered cell of claim 1, wherein at least 10%, at least 20%, at least 30%, at least 40%, at least 50%, at least 60%, at least 70%, at least 80%, at least 90%, at least 95%, at least 98%, at least 99% or all of said ERV elements present in the genome comprise the altered sequence.

6. The engineered cell of claim 1, wherein said engineered cell releases no ERVs.

7. The engineered cell of claim 1, wherein the genome comprises more than 10, 20, 30, 40, 50, 60, 80, 90 or 100 endogenous retrovirus (ERV) elements comprising the altered sequences.

8. The engineered cell of claim 4, wherein the targeted integration is an integration of a marker protein.

9. The engineered cell of claim 4, wherein the marker protein is GFP (green fluorescent protein).

10. The engineered cell of claim 1, wherein no release of viral sequences from said engineered cell are detectable.

* * * * *

SEQUENCE LISTING

<160> NUMBER OF SEQ ID NOS: 32

<210> SEQ ID NO 1
<211> LENGTH: 8366
<212> TYPE: DNA
<213> ORGANISM: Cricetulus griseus
<220> FEATURE:
<221> NAME/KEY: misc_feature
<222> LOCATION: (1)..(8366)
<223> OTHER INFORMATION: Group 1 type ERV of CHO-K1 cells

<400> SEQUENCE: 1
tgtaccagac accagacctt gagaatatgc tgatctggaa tggctctgtg tctcatttga 60
accatccaat ggaaatgatt ctgtatttcg cctcatttga aagactctgt gtttcacctc 120
atttgaataa ctctgtactt tacctcattt gaataaccct gtatagcgcc tcatatacat 180
tgaccaatgg gaatagctct gtataatgcc tcattagaat tatccaatag aatccttgct 240
cctagcttgc gccttttttc ctatataagg accccttttc ccttggctcg gggcgcttag 300
ccacacagaa gctaagtcgc cccaggtacc tgcgtctcca ataaagcctc ttgtttttac 360
atccagttcg tggcctcgct gattcctggg tgtgtgggtc tccctctacg aaagtgcctc 420
ttcggggtct ttcatttggg ggctcgtccg ggattgagac ccgcccaggg accaccgacc 480
cacgtctggg aggtaagtgt tgtgcggatc cgctgttttg tcttgtctgg tctgagtctg 540
tcttgtgaat tgcgcttgcg tttgtagtat acagctgtgt acatttgtag gcggatccga 600
ggagggactg acgggtccga actcccgacc gcggctccag gagacgtcct ggtagcgttt 660
gaagccctca ggaagaggga tttgtatttt gaacttggga agccctcagg gtgagagatt 720
tgtactttga acttagatct atgactggac attttcccag tctctttgga gaaggccctc 780
ggcttgaggg atttgcaatc tttactgggg acgaggaagg agggccccct tcctcgactc 840
tctctcaatt ccttctgtcg actctctgtc gaaaccgcgc tgcgaaagtc tgttctgtgt 900
tattcggtct ttgtcttgta gctgtcattt gtgccctcct aagcctagaa actatgggca 960
aactgtcacc actcctttgt ccctaacact ctcccactgg aaagatgtac aggaatatgc 1020
tcataaccaa tctgttaatg tgcgtaaacg caaatggatt actctttgtt cttcagaatg 1080
gccgaccttt gatgtaggct ggccgcgaga tggtaccttt aacccccaga ctatattcca 1140
gataaaagag aagattatgg atcctggacc acacgggcat cccgatcaag tggcttatat 1200
cgtcacttgg gaggctttgg ttcaggaccc ccctccctgg gtacgtcctt tcttacatcc 1260
caagggcccc tctctccttc cccctctaac cgctccaacc gacccattcc ttcggcccta 1320
cacctcccac tcctttgatt cctcccaacc cccttcccat tccaaccttt accctaccgt 1380
gatgaaagac actaaggcta aagaaaagaa gacacctaag gtactccctc cgggagaaga 1440

```
ccagttggtt gatctattaa cggaggagcc cccgccatat ccgccactgc cgcccccacc   1500
agaggcagaa gcggactccg ccgctgcctt ggcggaagcg gccctgaccc ttcaccaatg   1560
gcttatcgac taagaggtcg tagggagcag cccgttccag attcaaccac tctgcccctc   1620
cgaactgggc tgaacggcca acctcagtat tggccattct cagcatcgga cctctataac   1680
tggaaaaata ataatccttc tttttctgca gaccccgtga ggctgacatc tctcatagag   1740
tcggtactca cgactcacca acccacctgg gatgattgtc agcagctttt gcaggtcctt   1800
ttaacctcgg aagagaaaca gcgcgtgcta ctagaagcac gaaaaaatgt cccaggagta   1860
aacgggcagc ccacccagct acccaatgaa attgatgcgg cttgccctct tgaaagacct   1920
gaatgggatt ttaccaccga agcaggtagg acccacctgc gtctctatcg ccagttgctg   1980
gtagcgggac tccgggggca ggacgcagac ccactaattt ggcccaggtg aagcagataa   2040
tacagggtgc ggaggaatca cctgccgctt ttctagagag attgaaagaa gcgtacagga   2100
tgtatactcc ctataatccg gaagatccag gtcaggccac caacgtttct atgtccttta   2160
tttggcaatc agccccggac ataagaaaca agcttcaaag gctagaaaat ctacagggat   2220
atacactcca agatttgttg aaggaagcag aacgtatttt taataagagg gaaacacaga   2280
cagaaagaga agaacgttgg agaaggaaac tcaggagaga gaggaaagac taagacagga   2340
agctgaggaa aaagaggttg cgagagaccg taagcggaat aaagaaatga gcaggttatt   2400
ggccacagta gtgacaggcc agagacagaa tagacagagg gatgacagaa gggggcccca   2460
cctggacagg gaccaatgtg cttactgtaa agaaaaagga cattgggcaa gagaatgccc   2520
taagaacccc cggccaagct tccaccgcca agggtttctg acctcctgaa cctagaagat   2580
tagaggagtc ggggccagga gcccccccct gagccaggat aacactgcaa gtcgggggc   2640
atccggtcac cttcctagtc gatacagggg cacaacattc cgttctgaat cggtcacccg   2700
gacccctgag tcacaggact gcatgggtac agggagctac aggcggaaag cagtaccatt   2760
ggactacaaa tcggcagctc cagctcgcga ccggtaaggt tatgcattct ttcctccatg   2820
tgccagactg cccctacccc ttactagacg ggacctattg accaaattaa aagctcaaat   2880
acactttgag aggtcagaag tcaaagtcac agggccagag ggaattcccc ttaccatctt   2940
gacaatgtcc atagaagatg aatatagact ccatgaaaag aggactaatt cgaacaatca   3000
ggaaaccctt gatcactggc ttgcggaatt tccccaagcc tgggctgaaa caggaggaat   3060
gggccttgcc attaaccagg ccccaattat agtaacctta aaagctgcca tccttcctgc   3120
atccgtcaga cagtatccaa tgcctaaaga agcccgcgaa ggaattcggc cacatattaa   3180
aaggttactt gaacaaggga ttctggtgcc ctgtaaatct ccttggaata cacccttgct   3240
acccgttagg aagccgggaa ctaatgacta ccggccagta caggacctga gagaagtcaa   3300
taaaaggata gaggacatac accctactgt ccccaaccct tacaatttgc tgagtggatt   3360
gccacctaac tatacctggt acacagtctt agatcttaaa gacgctttct tctgcctccg   3420
cctgcatccc accagccagc ctatatttgc ctttgaatgg caggacgcgg cccttggaat   3480
ctctgggcag ctgacttgga ctaggctacc tcaagggttt aagaacagcc ctaccctttt   3540
tgatgaagct ttacatcagg acctggcaga attccggtta ggtaccccgc tctaatcctc   3600
ttacaatatg tagatgacat tctcctggca gccaaaacca aagggaaatg caaggaaggc   3660
actcaagccc tcctccagac tcttgggagc ctaggtaccg ggcatccgcc aagaaggccc   3720
agatatgtca gaaacaggtg acctatttag gatacaagat aaaggatgga cgtcgatggc   3780
```

-continued

```
taacggaagc ccgtatgcga gccatcttag acattcccac cccacaaaat ccccgccaac   3840
tgagagaatt cttgggaacg gcaggcttct gccgcctatg gatccctggg tttgccgaaa   3900
tggcggctcc cctctacccc ctcactcggc caggggttgc ttttaaatgg gaagagcccc   3960
aaaagaaagc cttcaccgac atcaaaaagg ctctccttga atcaccagcc ctgggtctac   4020
cggacttagc taagccattt gaacttttta tagatgagaa ggagggctat gctaagggag   4080
tcctcaccca aaatctgggg ccttggagaa ggcccactgc atacctctcc aagaaattgg   4140
atcctgtggc atcgggatgg ccaccctgcc ttcgaatgat tgctgctata gccctgctgg   4200
taaaagattc tcacaagcta accttggggc agcctttgac catacatgcc cctcatgcag   4260
tagaggcagt catcagacag cctccagata gatggcttac taatgcccga atgactcatt   4320
accagactat gctgttagac aaagaccggg tccacttcgg gcctttggtg actctgaacc   4380
cagccaccct gctccccctc cctggggagc ccgaggctca tgattgctta caggtattgg   4440
ccgaggccca tggagcgaga tccgacctga ctgaccagcc tctacctagc ccggaccaca   4500
tctggttcac ggatggaagc agctttttgc atcaaggaga acgaaaggcg ggcgcggcag   4560
tcaccacaga gaatcaggtc gtctgggccc aggcactccc cctggaactt ccgcacagag   4620
ggcagaactc atagcactca cgcaggctct aaaattggca gaaggtaaga ggctcaccgt   4680
gtatacagac agtcgttatg cctttgccac tgcccatata catggagaaa tttacagacg   4740
gagggggctg cttacctccg aagggaaaga cattaaaaat aaggaggaaa tcctcgctct   4800
cttaagggct cttcatctgc ccgctgcctt aagtatcata cattgccctg gacaccaaaa   4860
agggattctt tcgaagcaag ggcaatcgaa gggcagactt ggctgcccga gaggcggccc   4920
tgaccacaga caccactaac ctcctggctc tagagcccac caacgaccat cccttcccct   4980
catgggacta tgaacaaaga gacatccaaa ccctagagaa attgggagcc gcaaaggaac   5040
caaacgggga ttggacttat gaaggaaaga ctgtcatccc ctaccgggta accaagtacc   5100
tagtgacatt tttacataag atgacacatc tgagctccaa gaagatgcgg gagctcctcg   5160
aacgagaaga ggaattcaat ttccttttgg gaaagaacga tattctaaaa caggtaactg   5220
agcaatgtga tgcgtgcgcc cgagtcaacg catccagact gaagcttcct cccgggaacc   5280
gggtcagagg ctaccggccc ggaacacatt gggagataga tttcactgag attaaaccag   5340
gaaaatatgg atacaagtat ctattaattt ttgtagacac cttttcagga tgggttaaag   5400
ccttccctac taaacatgaa acagccaaga tcgttactaa gaaattgctt gaagaaatct   5460
ttccccgtta tgggatgcct caggtattgg gaacagacaa tgggcccgcc ttcgtctccc   5520
aggtaagtca gtcagtggcc accttattgg ggattgattg gaaattacat tgtgcttata   5580
gaccccaaag ttcaggacag gtagaaagga tgaatagaac aatcaaggag actttaacaa   5640
aattgtcgct tgcaactggc actagagact gggtcctcct actcccccta gcactctacc   5700
gcgctcgtaa taccccctgga ccacatgggc tcacaccctt tgagatcctg tatggagtac   5760
ctactcctat cattaacttt cttgatcaag atgtctcaga ttttgctaac tccccttctc   5820
tccaagctca tttacaggcc tccaactagt acaacgggag gtctggaaac cccttgctca   5880
agcttataaa gaccagaggg accatcccac catcccccat tcctaccaga tcgggacact   5940
gtttgggtcc ggcgtcacca ggccaagaac cttgaacccc gctggaaggg accctacatc   6000
gttttgctta ccactcccac cgcactcaag gtagacggca ttgcagcttg gatacatgct   6060
tcacatgtaa agccagccca acccaccgat tcagccactg catcagaatg gaccgcacac   6120
cgcactcaaa atcctttaaa gataagactc tctcgtacac cctcctgttg attggttgtc   6180
```

```
tgtttacccc ccatgtagca actaaccccc acagggttta taatatcacc tggaaaatag   6240
ccaatctagg gaccggggaa atagccaacc tcagcactta tatagggact ctacatgatg   6300
ggttccctcc tctctatgtc gacctatatg acttagtagg gtctgattgg gatccctctg   6360
accaggaacc attcccaggg tacggatgcc accaccctgg ggaaggatag gaacaagaag   6420
caaggatttt tatgtttgcc ccggccataa accaactcat ggctgcgggg gccgcaggaa   6480
gggtactgtg caagatgggg atgtgaaacc acaggggagg cttactggaa accctcttcc   6540
tcttgggatt tcatcactct caaacggagg gagatcccag ggtacgcagg gaaaggacca   6600
tggagatgtg ggcaaagagc ctgcggacct tgttatgata gtgccggagg gggaggtttt   6660
caaggcgcca cccccggagg aaaatgcaac cctctcatcc taaggttcac agatgctgga   6720
aaaagaacta cttgggatag tcctaaggtc tggggactca ggctgcaccg agcagggaaa   6780
gatccggtga ctttattctc cctgtacaga caaattactc ccctaagcca acaatcagtt   6840
gggccaaaca tagtaatagc ggaccagaga tcccaaccca ttttcaagtc cctaaacccc   6900
ctaccgttcc taaagctatc actcctacac caggtgctgt caccttctcc cccaccccag   6960
atgccctaaa catcgagata accagagacc ctccaggtac cagagataga ttattacaat   7020
taatccaagg agtttaccaa gccttaaatt tttcagaccc caacaagact caggaatgct   7080
ggttatgcct agtttcccgg cccccatatt atgaaggcgt ggcaatactg ggcaactact   7140
ccaaccagac ctcagcacct accagttgcg gagctgctat gcagcacaag ctcacaatat   7200
ctgaggtctc aggaaagggg ctatgcatag gcaggattcc ttcctcacat caagaattat   7260
gtaaccaagt agagccatta tctcaggaca gccgatacct tgttgcccct tatggaactt   7320
attgggcttg cagtactggg ttgactccct gtgtctctac cactgttctc aacaccacca   7380
ttgacttttg tatattgata gaactttggc ccaaagtcac ataccaccaa cctgaatatg   7440
tttacagcgt actagagaaa tcaacccgat ataagaggga gccactaaag caaatagatc   7500
cagagtatct agagacctct gaatgaaaga ttccattcag ttacaagaga aatgggggaa   7560
tgaaagaccc ctctccctta gccctttctt tctcaagttt gtctcctctt cctcctgtcg   7620
gcggcttccc cgatccccac ccccggtggc ctttccccgc ccggcccgag aacaagcacc   7680
gggtggggcc ggcccgagaa caagcaccgg gtggggccgg cccgagaatg agcaccaggt   7740
gggccagccc gagaacgagc accgggtggg ctggcacgag ggcgagcacc aggtgggtca   7800
gcacgaggac aaacaccgag tgagccggcc tggagctctg cccctgagcc cccgccccgc   7860
ccgaagagaa acactccgtc ccaaggtctc cgcccccaagg tcagccatca ggaaaagggg  7920
ggaattgagt ctgctgtacc agacaccaga ccttgagaat atgctgatct ggaatggctc   7980
tgtgtctcat ttgaaccatc caatggaaat gattctgtat ttcgcctcat ttgaaagact   8040
ctgtgtttca cctcatttga ataactctgt actttgcctc atttgaataa ccctgtatag   8100
cgcctcatat acattgacca atgggaatag ctctgtataa tgcctcatta gaattatcca   8160
atagaatcct tgctcctagc ttgcgccttt tttcctatat aaggacccct tttcccttgg   8220
ctcgggcgct tagccacaca gaagctaagt cgcccaggta cctgcgtctc caataaagcc   8280
tcttgttttt acatccagtt cgtggcctcg ctgattcctg ggtgtgtggg tctccctcta   8340
cgaaagtgcc tcttcggggt ctttca                                         8366
```

<210> SEQ ID NO 2
<211> LENGTH: 8667
<212> TYPE: DNA

-continued

<213> ORGANISM: Cricetulus griseus
<220> FEATURE:
<221> NAME/KEY: misc_feature
<222> LOCATION: (1)..(8667)
<223> OTHER INFORMATION: Group 2 type ERV of CHO-K1 cells

<400> SEQUENCE: 2

```
ctctctctct ctctcttggg ctagctaaat tacagaccaa gagaccaaga ccacccagaa     60

ccatttctga gaatagaagg tcagggcgtt atgactactt gtttgccaca caggatatct    120

gtggtcagcc atctggacgc ggagggagga actgccgggt ctgttgtaac cactgtgtac    180

ccaagataga gccaagtcag cttcgtctga ttaccagacc ttgagaactt gctaacctga    240

aataactctg tgcctcattt gaattgtcca atagagtccc tgtaactatg cttttcgctt    300

ctgtactatg ctttttgcta tataaggacc cctctccctt ggctcggcgt gcttggcctc    360

acagaagcta agtcgcccca ggtacccgtg tatccaataa agcctcttgc tgtttgcatc    420

caagttcatg gtctcgctga ttcctgggta cgggtctcct tctgtgaaag tacctcttct    480

gggggtcttt catttggggg ctcgtccggg atcgaaaccc cccgcccagg gatcaccgac    540

ccacgtctgg gaggtaagcg ttgtgcggat ccgctgtctt gtctgtcttg tcttgcctgt    600

ctgtctgaat ctgtcttatg aactgcgctt gcgtctgtag tacacagctg cgtacatctg    660

tatctggcgg ctccgaggaa aaactgaaga gttcagactc ccgaccacgg ctccaggaga    720

cgtcctggta gcgtctagag cctcagtggg ctcactcttt tttctgacta gggtagatgc    780

ctaggcatct tcccaatctg tttggggaag cccctcagat tgagggattt gctatcctca    840

tcggggacga ggaagggagg ccccccttctt cggccccatc tgaagtttta ctttcgacct    900

tgtgtcgaaa ccgcgccgca aaagcctgtt ctgtgttgct cggtctttgt cttgtaacca    960

tcatttgtgt cctcctaggt ctagaaacta tggggcaaac tgtcaccact cctttgtccc   1020

taacactctc gcactggaga gatgtgcagg attatgctca taaccagtct gttgatgtgc   1080

ataaacgcaa atggattact ctttgttcct cagaatggcc aacctttgac gtgggctggc   1140

cgcgagatgg tacctttaac ccccaaacta tatttcaggt gaaagagaag actatggatc   1200

ctggaccaca ggggcatccc gaccaggtgg attacatagt cacttgggag gccttggttc   1260

aggaccctcc ccctgggtac gtcctttctt acaccccaag ggcccctcct tcctttcccc   1320

ctctaactgc tccagccgac ccactccctc ggcccctacc cttcccaatc cctcgacacc   1380

cactcctccc taccctcctc cccattccaa cctttaccct acagcggtaa aagacgctaa   1440

agctgaagaa aagaagacac ctgaggtact cccccgggag aagaactgtt ggttgactta   1500

ctgactgagg aacccccgcc atatccagca ccgccaccgc ccccaccaga ggcagaagcg   1560

gcccccgccg cctcggtgga ggtggcccca gctcccccac ctgacccttc cccaatggct   1620

caccgactga gaggtcgcag ggagcagccc gctccagatt caaccactct gcccctcaga   1680

actggaccga acggccattc tcagcctcgg acctctataa ctggaaaaat aacaatcctc   1740

ctttctctgc agaccctgtg aggctgacat ctctcataga atcggtcctc acaactcacc   1800

aacctacctg ggatgattgt gaacagattt tgcaggttct cttaacctcg gaggagaaac   1860

agcgcgttct actagaggca cgaaagaatg tcccaggagc caacgggcag cccacccagc   1920

tgcccaatga aatcgatgcg gcttgccctc ttgaaagacc tgaatgggat tttaccactg   1980

aagcaggtag gacccatcta cgtctctatc gccagttgct cgtagcgggt ctccgggggg   2040

caggacaccc acccaccaat ttggcccagg taaagcaggt aatacagggg gcggaggaat   2100

cgcccgccac ttttctagag agactaaaag aagcgtatag gatgtatact ccctatgatc   2160
```

-continued

```
cggaagatcc agggcaggcc accagcgttt ctatgtcctt tatttggcag tcagccccgg   2220
acataagaaa caagcttcaa aggctagaaa atttgcaggg atatacactc caagatttgt   2280
tgaaggaagc agaacgtatt tttaataaga gagagacaca gacagaaaga gaagaacgct   2340
ggagaaagga aacccaggag agagaggaaa gactgagaaa agaagctgag gaaaaagagg   2400
ctgcaagaga ccgtaagcgg aatagagaga tgagcaggct attggccaca gtagtgacag   2460
gtcagagaca gaataggcag agggatggca gaagggggcc ccacctggac agggatcaat   2520
gtgcttactg caaggaaaaa ggacattggg caagagattg ccctaagaac cccgggccaa   2580
gcctccacgg ccaagaacct ctgaccttct aaacctagaa gattagagaa gtcagggcca   2640
ggagcccccc cccctgagcc caggataaca ctgcaagtcg gggggcatcc ggtcaccttc   2700
ctagtcgata caggggcaca acattccgtt ctgaatcagt cacccggacc cctgagtcac   2760
cggactgcat gggtacaggg ggctacaggc ggaaagcagt accgttggac cacagatcgg   2820
cagctccagc tcgcgaccgg taaggtcatg cactctttcc tccatgtgcc tgattgcccc   2880
taccctttac taggacggga cctattgacc aaactaaaag ctcaaataca ctttgagaaa   2940
tcaaaagtca aagtcacagg gccagaagga attcccctta ccatcttgac aatgtccata   3000
gaagatgaat atagactcca tgaaaaagag actaactcgg gcaaccagga aacccttgac   3060
cactggctcg cggaatttcc ccaaacctgg gctgagacag gcggaatggg ccttgccagc   3120
aaccaggccc caattatagt aaccttaaaa gctgccgccc ttcctgcatc cgtcaagcag   3180
tacccgatgc ctaaagaggc ccgcgaagga aacatattaa aaggttactt gaacaagaga   3240
ttctgacgcc ctgtaaatct ccttggaata cacccttgtt gcccgttagg aagccaggaa   3300
ccaatgacta tagaccagtg caggatctga gagaagtcaa taaaaggata gaggacatac   3360
accctactgt ccctaaccct tacaatttgc tgagcggatt gccacctgac tatacctggt   3420
atacagtctt agatcttaaa gatgccttct tctgcctcca cctgcatccc accagccagc   3480
ctatatttgc ctttgaatgg caggacgctg accttggaat ctctgggcag ctaacttgga   3540
ctaggttacc tcaagggttt aagaacagcc ctacccttt tgatgaagct ttacatcagg   3600
acctggcagg attccaggtt cggtacccgg ctctaatcct cttacaatat gtagatgaca   3660
tcctcctggc agccaaaacc caggggaatg taaggagggc actcaagccc tcctccagac   3720
tcttgggagc ctagggtacc gagcatccgc caagaagtcc cagatatgtc agaagcaggt   3780
gacctattta ggatacaaga taaaggacgg actgcgatgg ctaacggaag cccgtatgtg   3840
agccatctta gaccttccca ccccgcaaaa tccccaccaa ctaagagagt tcttgggaac   3900
ggcaggtttc tgccgcctat ggatccccgg gtttgctgaa atggcggctc ccctctaccc   3960
cctcactcgt ccagggattg cttttaaatg ggaagagccc caaaagaaag ccttcaccaa   4020
catcaaaaag gctctccttg aatcaccagc cctgggacta ccggacttgg ctaagccatt   4080
tgagttcttt gtagatgaga aagagggcta tgccaaggga gtcctcaccc aaaaactggg   4140
gccttggaga aggcccactg catacctctc caagaaattg gatcctgtgg catcgggatg   4200
gccaccctgc ctccaaatga ttgccgccat agccttgtta gtaaaagact ctcacaaact   4260
aaccttgggg cagcctttga ccatacatgc ccctcatgcg gttgaggcag tcatcagaca   4320
gcctccagac agatggctca ctaatgcccg aatgactcat taccagacta tgctgttgga   4380
caaagaccgg gtccactttg gccctttggt gactctgaac ccagccacct tgccccccctc   4440
cctggggagc ccgaggctca tgattgcttg caggtactgg ctgaggccca tgggacaaga   4500
```

-continued

```
cccgacctaa ctgaccagcc tctacccagc ccggaccaca tctggttcac ggatggaagc   4560
agctttttgc atcaaggaga acggagggct ggtgcagcgg tcacctcaga ggatcaggtc   4620
gtctgggccc aggcactccc tcccggaacc tccgcgcaga gggcggagct cattgcactc   4680
acgcaagctc taaagttggc agaaggtaag aggctcaccg tgtacacaga cagtcgttat   4740
gccttcgcca ctgcccacat acatggagaa atttacagac ggaggggggta gcttacctca   4800
gaagggaagg acattaagaa taaggaggaa atcctcgctc tcctaagagc tcttcatctg   4860
ccctccgcct taagtatcat acattgcccc ggacatcaaa aaggggattc tcttgaagcg   4920
aggggcaatc gaagggcaga tttggccgcc caagaggcgg ccctggccac agaaaccact   4980
aacctcctgg ctctagaacc caccaacgac cgtccctccc cctcatggga ctatgaacaa   5040
agagacatcc agaccctaga gaaattggga gccaccaagg aatcaaacgg ggattggact   5100
tatgaaggaa agactatcat cccctaacgg gtaaccaagt acctagtgac atttttacat   5160
aagatgacac atctgagctc caagaagatg cgagaactcc tcgagcgaga agacgaattc   5220
aatttccttt tggggaagaa taacattcta aaacaggtaa ctgaacaatg tgatgcgtgc   5280
gcccgagtca acgcatccag actgaagctt cctcccggga accgggtcag aggctaccgg   5340
cccggaacac attgggagat agatttcact gagattaaac caggtaaata tggatacaag   5400
tatctattag tttttataga caccttttca ggatgggttg aagccttccc tactaaacat   5460
gaaacagcca agatcgttac taagaaattg cttgaagaaa tctttccccg ttatgggatg   5520
cctcaggtac tggggacaga caatgggccc gccttcgtct cccaggtaag tcagtcagtg   5580
gccaccttgt tggggattga ttggaaatta cattgtgctt atagacccca aagttcagga   5640
caggtagaaa ggatgaatag aacaattaag gagactttaa caaaattgtc gcttgcaact   5700
ggcactagag actgggtcct cctactcccc ctagcactct accgcgctcg caataccccct   5760
gggccacatg ggctcacacc ttttgagatc ctgcatggag tatctacccc tatcattaac   5820
ttccttgatc aagatgtctc agattttgct aactcccctt ctctccaagc tcatttacag   5880
gccctccaac ttgtacaacg ggaggtctgg aaaccccttg ctcaagctta taaagaccag   5940
agggaccatc ctaccattcc ccattcctac cagatcgggg acaccgtctg ggtccggcgt   6000
caccagtcca agaacctcga accccgctgg aagggaccct acatcgtttt gcttaccacc   6060
cccaccgcac tcaaagtaga cagcattgca gcttggatac atgcttctca tgtaaagcca   6120
gcccgaccca ccgattcagc cactgcatcg gaatggactg cgcactgcac tcaaaatcct   6180
ttaaagataa gactctctcg tacaccctcc tattgattgt ttgtctgttt atcccccatg   6240
tagcaaccag cccctatacc attcatgcgt taacctggca ggtactttcc cagtcagggg   6300
aggtcattta tgagaccacc aaaaaccatg cccttggtgt atggtggcct acattgacac   6360
ccgatttctg tgacttggtc gctggtctag acacctggga catctcacac tgttacccta   6420
aggcttgtag caacgaaaac gatttgccac gatttcgcag gtcactccaa agttcgagag   6480
acaccactcc tggatgtagc agtcaacagg ccaaagacca actgtcgggt agtgactttt   6540
atgtctgtcc cagagacgga cgggcctgga agaagactca gacttgtggg ggttatgaac   6600
agtttttctg tgccacttgg ggatgtgaaa cgacagggga tgcttactgg aagccttcat   6660
cctcatggga caagattcaa gtaaccagag gatggcaaaa gggctccacc ggcaccacct   6720
ctatgcctct ccttatttcc tttacggatg agggtaagaa agcaacagaa tggcagaacg   6780
gatatgcttg gggccttcgc tggtacctgt cgggaccaga ccgggggggcc atctttaaaa   6840
ttagactcaa agtaaaaact atcaccaaaa ccatgggccc aaacccagtt ctggcagacc   6900
```

```
agaaacccccc accaagcctc atgggtctcg gccccatagg cctctatccc atctcccacc   6960

ctcatcaaca ccctcatcca atactgccac ccttactctt acgactccag ttcacacccc   7020

cacctcccca tatccaggga caagggacag attacttgaa ctaatacaag gggcttactt   7080

ggccctcaat tcctcagacc ccaacaagac tcaggaatgc tggctatgcc tagtttcccg   7140

gcccccatat tatgaaggca tagcagtact gggcaactac tctaaccaga cctcagcgcc   7200

taccagttgt ggagctgcca tgcagcacaa gctcacaatg tctgaggtct caggaaaggg   7260

gctatgcata ggcagggttc ctccctcaca tcaagagtta tgtaaccaaa cagagccatt   7320

atctcaagac agccgatacc ttgttgcccc ttatggaact tattgggctt gcagtactgg   7380

tttgacaccc tgcgtctcta ccactgtcct caatgccacc attgactttt gtatattgac   7440

agaactttgg cccaaagtca cataccacca acctgagtat gtttacagcg tactagagaa   7500

atcaacccga catcagaggg agccaatgtc cttaaccgtg gccctattat taggaggaat   7560

aacaatgggg ggtatagcag ctggaagagg gaccagtacg gttgccttgc aggaaactag   7620

ttatttcaaa cttctacaac aagccatgca tacagatatc caggccctag aagagtcagt   7680

cagcgcactc gagaaatcct taacatcact ctctgaggta gtcctgcaga acagacgaga   7740

gttagattta ttatttctac aggaacgggg actatgtgct gccctcaagg aagaatgctg   7800

cttttatgca gaccacacag gaatagttag ggacagcatg gccaaactta gagaaagact   7860

taagcagagg caacaactat ttgagtctca acagggatgg ttcgaaggat ggttcgctaa   7920

gtccccctgg ttcactaccc ttatatccat tctcatggga cctctgatta ttctattttt   7980

aatccttata tttggtacct gcattctaaa taagatgact caattcatca gagaacgact   8040

atctgtcata caggccttag tcttaactca acaataccat cagctaaagc aaatagatcc   8100

agaatatcca gagacctctg aatgaaagat tccattcagt tacaagagaa atgggggaat   8160

gaaagaccac tgccccttaa gctctctctc tctctctctt gggctagcta aattacagac   8220

caagagacca agaccaccca gaaccgtttc tgagaataga aggtcagggc gttatgacta   8280

cttgtttgcc acacaggata tctgtggtca gccatctgga cgcggaggga ggaactaccg   8340

ggtctgttgt aaccactgtg tacccaagat agagccaagt cagcttcgtc tgattaccag   8400

accttgagaa cttgctaacc tgaaataact ctgtgcctca tttgaattgt ccaatagaat   8460

ccctgtaact atgcttttcg cttctgtact atgcttttg ctatataagg acccctctcc   8520

cttggctcgg tgcgcttggc ctcacagaag ctaagtcgcc ccgggtaccc gtgtatccaa   8580

taaagcctct tgctgtttgc atccaagttc gtggtctcgc tgattcctgg gtacgggtct   8640

ccttctgtga aagtacctct tctgggg                                    8667
```

```
<210> SEQ ID NO 3
<211> LENGTH: 8181
<212> TYPE: DNA
<213> ORGANISM: Cricetulus griseus
<220> FEATURE:
<221> NAME/KEY: misc_feature
<222> LOCATION: (1)..(8181)
<223> OTHER INFORMATION: Intracisternal A-particule retrovirus like
      sequence of CH0-K1 cell

<400> SEQUENCE: 3

ctgtagagag ctgcagaaaa ccgcacccaa aagatggcgc tggtttccgc cttccgccag     60

cccgacggcg agcgctctct gtggtaaaca actccaaata tggtagaggt catgtatcct    120

cttaattctg cttggagaca acctatcctg gcgcgccacg tagggttagg tgattggtag    180
```

-continued

```
atgtagacta tatcaggccc cgtctccctc ggcctggggc cgccgcctcc attatacatt    240
gtacaaaagc aaagaggttc ccgattaaac tgtgtttgaa gaagattcct cggtgtggcg    300
tctttcttgc tggtcaaggg tggacgccgc aagtggtggc ccgtacgggg aattcagaac    360
ttctcacagt cggggcggcg ccggtaagtt cccaaggtaa gtggaactgt aaagtccgcg    420
gtgaatgcgg agataggtct ccggtaaagg agcaccaagg tcctcaggaa agaggagata    480
ggtctcagta aaagagtacc aaagccctcg ggaagaggc agtaaagtct ccggaaagga    540
gcaacattgt tcgcgacaaa agcgaaccga aagtaaaaaa ccctcgcttc tgctttaatt    600
tgcagagtga aagtaagtta atggaccccg ctattatagt ggtgatttgg ttgcttttta    660
atatcgcagt gtgggctttt gttttctggt ggtgttatcc gacttgcaca ccttcggagc    720
gcgctaatta agacaaaagc acaatgggat cgtcacaatc acatccaatt tttctggctc    780
ttcaagagct acttcattct aacaatttaa ggttaactaa agccacatta cagaggttcc    840
tgagtgaatg cgacaccatt gcaccctggt ttgcagcctc gggcaatctc actgtggata    900
gttgggataa attagggaaa gacctggatt ttgcctggga gcaaggagcg ttgaagccga    960
gtgttcgccc ggtttggcgc ctggtgcgca gctgtctaga ggacaaaggg ggaaataaga   1020
aagctatagc aaatggacag gctgcccttg aaatgctcca agaagaaagg tcagaacagt   1080
cagaaagtga gagaacaaag gagaaacaga aaagggataa gaagcgagtc tatccttctc   1140
taggaaggtt gaggaaggaa ttaaaagaac caggagagga ttcagaatca gaggaggata   1200
tatgtgagga tgaggacatc atggaggaag aggaggaaga gattattgag ctcatggaaa   1260
aacattcatt aaaagtatca gaaaaacagc gtcctaaaat ggcgactgta aagcaagggc   1320
accgccctat cgctcctccc cctactgctc gaaagaggaa gtaggaggtc ctggttgttc   1380
caccttctgt ccggaagtgt ggcgtacggt tcgcactgag tttcgggtta ctcgaccact   1440
ggcttatcca gtttttacag acggtaacca acagagatat catgaaccaa ttgactttaa   1500
aatagtcaaa gctctggcag aatcggtacg cacctatggg gtgacggcag cttttacaat   1560
tgctcaggta gaggcgctcg gtcgctactg tatgacaccc agtgattgga caaatttggt   1620
aagagcttgc ttatcaccag gacaatattt ggattggaga gcttttcaaa ttgagtttgc   1680
caatgatcaa ggtgcgatta atcgtgcagc tggtgatcaa tattgggatg tggacatgct   1740
tcttggtcaa ggacgttttg cacagcaaca aacaggatat cctcctcaag tgtatgatca   1800
gattaatcaa atagccatta gggcttggag gtctctgcct aacaaaggtg aggtcagtgg   1860
aaatcttaca aagatattac agggtcctat ggaacccttt tcagactttg tggcaagaat   1920
ggtagaagct gcaggaagag tgtttgggga tccagatgct gctatgcctt tgatcaaaca   1980
gctgatttat gaacagtgta caaaagagtg tagagctgca ataactccat ataagggtaa   2040
aggccttgaa gtctggatga aagtctgtag ggagttaggg ggtccgctga ctaatgctgg   2100
actagcagct gctgtgatgc aattaactaa gaaaggtgga ggttcaggag cttgctttaa   2160
atgcggcaag caagggcatt tgaaaaagca atgccccgag ggaggaaaca ctaaagtcaa   2220
taactttgct ccgcgcccta agcaacctgg cttatgtcct agatgtaaaa aaggaaatca   2280
ttgggctaag gattgtagat cagtaaaaga catcagtgga cagcctcttg ttcaggggta   2340
tggaggagcc cgttcaaaaa acggacgacg gggcccacga ccccagggcc cacaaatata   2400
tggggccatg gaggatcaga accaggagca gagtcccgaa acctggccct ctcttcgtca   2460
tccgagggac cgaggagagc cactacaggc tccgcggggc tggacttacg ctccaccacc   2520
```

-continued

```
agactcgtat taactcccag aatgggggtc cagcttgttg acaccgattt taagggaccc   2580
cttgagcctg gcacagtagg tttgcttata ggaagatcat ctgcagcatt gaaaggttta   2640
cgagtacatc ctggagttat agatcctgat tacatgggtg tagtaaagat catggtagaa   2700
tctcctagag ggattacggc catttctcct ggagacagga tagcacagtt actgcttttg   2760
ccaagcttgc atgacaagtt tccagcacaa gccagagaga gaggagaggg aaactttggc   2820
tccactggat caaacttaac tttcctagct ttagaccttg atcaacgtcc aacccttgag   2880
ttaatagtga atggtaagaa aatcttaggc ttactagatt ctggagctga taagagcatc   2940
atagccacta aagattggcc ctctggctgg cctatacagg tttcttctca aagtttacaa   3000
ggtttaggct atgctaaggc tcctgatatg agtgctagac aattgccttg gaaagatcag   3060
gaagggcatt cagggaccat gcaaccttat gtgttagact taccaatttc attatgggga   3120
agagatttgt taaaggatat gggttttaaa ctcacaaatg aatactcaga aacatctcaa   3180
ggtatcatga aacgaatggg atacgtccca ggccgaggcc tcgggaaaca tctgcagggt   3240
cgtaccagtc ctattattcc acaaccgaga ccaaagaatc taggtctggg tttttcctag   3300
gggccactga gggaggtatt cctattacct ggaaaacaga ggagccggta tgggttcctc   3360
agtggccact ttcctctgaa aaactggaag ctgctaagac tctagtgcgg gagcagctgg   3420
atctggggca tataaaatcc tctgtatctc catggaatac tcctattttt gtcattaaga   3480
aaaaatctgg taaatggaga ctgcttcacg atcttagagc tattaatcaa cagatgcaaa   3540
ttatgggccc tgtacaacgt ggtcttccac ttttaacttc tttacctgca tcatggccta   3600
tcatctctat agatattaaa gattgcttct tttccatacc tttgtgtgcc aaggattcag   3660
ggcgttttgc gtttacgctg ccctcttgta atcatgaaca acctgattta aggtatgaat   3720
ggatagtgtt gccacagggg atggccaata gtcctactat gtgtcagttg tttgtagcag   3780
aagcaattgc tcctttgaga gtggactttc caaagattag atgtgttcat tatatggatg   3840
atattttatt ggctgccaaa gatgataaaa cgcttaataa ggcatataca aaattggtaa   3900
aattgcttga gatgcataat ttagtcatag cctcagaaaa ggtacaaaag gacactgttg   3960
ttaactatct aggggctaag attctccctc atacaattat tccacaaaag atagagatta   4020
gaaaagataa tttaaaaact cttaatgatt ttcaaaagtt gttgggagat ataaattgga   4080
taagatgtta tttaaaatta ccaaattatg agttgaagcc attgtataat attctcaatg   4140
gtgattcagc attagattca cctaggcagt taactgctga agccagagaa gctttaaaga   4200
aagtggagac agaattacaa aatgccagcc ttaaaaggct aatagaaaat atggatattc   4260
ttttgtgtgt gcttcctaca ttctcccagc ctacagcttt gctgtggcaa gatggtccgt   4320
tactatggat ttattctaaa tcctccccag gaaaaactat tgaatactat cctgcagcgg   4380
ttgctgactt ggctcaaaat gggatacagc aatgtattca atattttggg aaattaccaa   4440
ttaagatcat aatcccttat actgctcaac aagttaagat actttgtgga actgtggatg   4500
attgggcaat tcttcaatgt ggattttcag gagaaataga taatcattat ccaaaacacc   4560
ctctaatgtc attttttaaa gaacatccag tcatttttcc taaaatgact gcagcagctc   4620
ctattgctgg agccgcaaat attttcactg atggatccaa gacgggctgt ggagcctaca   4680
tgatagagca tcaggatcca gtgcaatttc aatatcagcc tggctccccc caaattattg   4740
aatgtaaaat tgttcttgaa gtgtttagaa attgcccgtt ctcctttaat ctgatttctg   4800
attcggcata tgttgtgaat gctgttaagg ccctggaggt tgcaggacct attaaaccta   4860
atagtacagt ttgcaaactc ttacaggagt tgcaaaagtt gatctggcat cgcgatcaga   4920
```

aatttttttat acaacatatt agagctcata ccaacttgcc tggacctcta tcaaaaggca 4980
atgagatcgt agatctctgt actagagggg aatatgtatt tttcgcttcc tctatggaac 5040
gagcacagca ctttcacaaa caatttcatg tatctgcaaa aactttacag caaaggtttc 5100
agctatctcg agcagaagct agacagatag tattgaattg tcaacagtgt ataaccttct 5160 tgcacccccct agcctggggg tcaatcccag agggttattg cccttgaaga tctggcaaat 5220
ggacgtaact catttttcag gatttggaac tcttaaatat atccatgtgt ctgtggatac 5280
ctgttcaggc atcatccatg ccacccctat gagtggggaa aaggctcgca atgtcattgg 5340
acattgcctt gaggcgtggg ctgcctgggg aaaacctcag caattaaaga ctgacaatgg 5400
tcctgcttat acagctcaat cttttacctc cttctgtaaa cagatggaag tccaattaaa 5460
ccatggcctg ccttataatc cccaaggaca aggaatagtt gaaagagccc atcgcacatt 5520
gaaagaatgt ttactaaaac aaaaagggga ataggccatg gtagaacacc aaaggaacaa 5580
ctatctttgg ctctctttac tctgaatttt ttaaatttgg attctcaagg cctttctgct 5640
gccgataggc accagactcg ggcacctgct cagaagggct atgtaaaatg gaaagatatc 5700
cttacgggtc tatggcatgg accggacccg gtattagcat gggcgagagg ttctgtttgt 5760
gttttccctc aggatcagca agacccggtg tggattccag agagactaac gaggaggtgc 5820
aacaaacaag atgaagcctc cgatattgat cctgctgctg atcttgacaa caccgtggct 5880
gatccaggcc agagaacaaa tcctgtgggc catagcgaaa gcgtggccaa ttcctttgcc 5940
tgttcatagc acatctaaag ttttgcctgt tttcttttct actagttgtg aattgggttt 6000
gccttgtgtc aatttagatc ctgacactgc ccagtattca gccactaata tttctctcaa 6060
tggagcatta tgcttctccc ttattaataa ttctaaccca tgcatttggt tgaagaatgg 6120
ttctattggc aattggcttg atcctcttac taataaccag atctcgagtg ctatgctcac 6180
tgaagccctg tctcagttta gtacaggcgc tagttctggc tctggcactg gtacaaatgg 6240
aaccaaagat gtaaatatca ctacatttct gatgctgatg gaggggctcc gaccctcaaa 6300
ttcacgcttt agtcaagaga actccactgc tcgacaagtc ttgccttatt gtgcacccaa 6360
tcgaggctat ccacctcatt ggacgccttg tcagagtccg gatcacaaac ttaagcaaat 6420
agctccaggt tttgaattta ctcccccctct tggcaagtac cagtataacc taactcaggg 6480
aggttcccaa agaacaggca gtaaaaacac ctggccatgg tttcaatggg tactctccaa 6540
cgagcgtgaa acatttactt ctcttgaacc ttttgcagtt ctccagaatc tctgcataag 6600
acttcttaat gtttctggta caagggatga gaagggacct tctcttaaga atctatcaat 6660
acataaagct ttgaataatc tcactgttcc agctagccca gtatgcttaa aagctccttt 6720
tttctttctg ctctctaatg ctattgatgc taccaaagaa gtgatctcgt gcaattcgac 6780
tgatgtctcc tgcattgcta gccaatgttg gaatggttct gctaatacag cagtagtgat 6840
gaggattcct atgtatgttc ctattccagt caaagtggat acaggaacgt ttcccattac 6900
ggaaatcatc agaaccaaac gggattttgg cataactgca gcattggtta ctgccattac 6960
cctttctgca gcagcggcta cgactgccac cgttgccatg gctgctcagg tccaatcagc 7020
tgagacagtc aatgatattg tggaaaaaac agctacaaca ttaactacct tgagatctat 7080
tgatggccac ttaaaagctg gcattctaac tgtgaaccaa agagtggacc tgttgcagga 7140
acaggtggat gatttagtaa ccttaacttc cataggatgc attcattcct tttcttcttt 7200
gtgtatcacc tccaggatgg ccaataattt cacggagaac agcaacctga gttggcagct 7260

```
gagtgcctac cttcagggaa attggagtca acagttcgag aacctgacag acaccctgac   7320

acaacagatt attgccgtga atgctacacg cctgagcctg cccactgtta ataccctctt   7380

aactaccctt aagcgagcct ttagtttagt taaggaatgg gctggaatag gggttatgtt   7440

ttccatgatg ctgttagcca tttttgtttg cttgtggtgc ctatgcagga tcaggaagtc   7500

gcaaaaatcc caagctgcta tgttggtaca ggcctttgct gctgtggaag caggacagtc   7560

ccctcaagca tggttatcca tgctgacaga caaatagatg tctgtctcgc ccttgctgag   7620

tgagtaatgc gtatctgaat cagtcatgct caatgacggg cacctaccct catgctgagc   7680

gaataagcat acgtgtgttg ccttcaacct aagacatgag cctgtgaggg cgacacagtg   7740

actctttgac gggtaagata gggacactgg ggttgaacct aagacagaga tgactgaaat   7800

ctgacaacag atagatactg ctactcctat aatattaaaa caaaaagggg gaactgtagg   7860

gagctgcaga aaaccgcacc caaaagatgg cgccggtttc cgccttccgc cagcccgacg   7920

gcgagcgctc tctgtggtaa acaactccaa atatggtaga ggtcatgtat cctcttaatt   7980

ctgcttggag acaacctatc ctggcgcgcc acgtagggtt aggtgattgg tagatgtaga   8040

ctatatcagg ccccgtctcc ctcggcccgg ggccgccgcc tccattatac attgtacaaa   8100

gcaaagaggt tcccgattaa actgtgtttg aagaagattc ctcggtgtgg cgtctttctt   8160

gctggtcaag ggtggacgcc g                                              8181
```

<210> SEQ ID NO 4
<211> LENGTH: 8369
<212> TYPE: DNA
<213> ORGANISM: Cricetulus griseus
<220> FEATURE:
<221> NAME/KEY: misc_feature
<222> LOCATION: (1)..(8369)
<223> OTHER INFORMATION: Gibbon-ape leukemia virus like ERV of CHO-K1 cell

<400> SEQUENCE: 4

```
aaaaaaaaaa aaagaaaaga aaagaaaaga aaaaacagtt cccagaataa ctacccgagg     60

ttctgatgac ctctatggaa tgtttcaacg ccctaagtgt gcctcaggtg tatgattcat    120

gtgacacatg gtttatggtt taactgaaga atactgtatg actctgatat ttccccattc    180

ttttgtgggt tttttgcctt tataagcctg ttacaaattc agaccggggt cgaactcctc    240

taccccctgtg tggtgtatgg gtttcgaccc cagcatgctg gtctgagatc tcgttccgtt    300

tcactctcaa taaacttcct cgtgtgattg cagcaagtct ggtcttggtg cctactgggt    360

gcgcgccttt cccgaggctt gagtgagggg tctcccttcg ggggtctttc atttgggggc    420

tcgtccggga tttgcgcgac cacccagggg tcctagaccc acttggaggt aaggattttc    480

attcctcgtt gttctgttgt gattctgtgt ttgtggattg ttcagagatc tggtgcgatc    540

gcagttctgg tttttgcaaa cgctctaatc gagtctgctc ctccagaggg gggagcagag    600

tggacgggga tagacgtatc cgggtgtcca ccgtttgttc gccctgggag acgtcccagg    660

aggacagggg aaggaccagg gacgcctggt ggaccccacg aggaaagtcc ggggattagt    720

ttcctccttg acaatctgta gaccgtctga ctcttttcag gatttctggt cgactcaagg    780

tcggcgattt tgtctctctg ttttgttgtc tttgtgattg ttctttttgt gaagtgtgat    840

agaaccagga atgggacaga ccgtgacgac cccgctaaca ctgaccctgg accattggac    900

ggacgttaag acgagggctc ataatctttc tgttgaagtc agaaaagggc catggcagac    960

tttctgctcc tctgagtggc cgagttttgg cgtaggatgg cctccggagg gaactttttaa   1020
```

cctgtctctc atttccgctg tcaagcgaat tatctttcag gcctcagggg gacaccctga 1080
tcaggttcca tacattatcg tatgggagga cctggtccaa aatccgacac cctgggtgag 1140
accctggacg acaggggcag aaacggtgac ggtggccgtg gccgccaaac cgaaagtacc 1200
ccctccagat aaaccggtac ctgctccatc ggcccctacg aagatttatc ctgaaattga 1260
tgatggttcc cttctcctcg actaccctcc acccccgtat cctcaaccag cttcccacgc 1320
acgtccccca caggtgtcgc cccccgccga ctcccggacg gcctctgaaa caggaccggt 1380
ggccggaacc cgaagccgcc ggggtcgtag cccaggggag aaggcgcggg gtttgactct 1440
gctactgccc tacctttacg agcttatgga cccgccccgg ctccgggaga actggtcccg 1500
ctacagtact ggccgttctc atcagccgat atgtataact ggaaaactaa ccactcctct 1560
ttttcagaga atccctcagg cctgacaggg cttcttgagt ccctaatgtt ttctcatcag 1620
cccacctggg atgattgcca gcagcttttg caagtccttt ttaccacgga agagagggag 1680
agaatcctcc tagaagctag aaaaaatgtt ccgggaccag atggagcccc caccaacctc 1740
cctaacctta tagatgcagc ttttcccttg atccgccctg actgggatta taactctgca 1800
gaaggtaggg agcgtctcac ggtctaccgc cgggctctag tggcaggtct caagggagct 1860
gcaaggcgac ccacgaattt ggctaaggta agggaggtcc tacaaggtcc ggtggagcca 1920
ccctctgtct ttttagagcg cttaatggag gcttacagga gatatactcc atttgatccc 1980
tcctcagagg gacagtgggc ggctgtagct atggctttta taggacaatc agcccctgat 2040
atcaagaaga agttacaaag attagagggg ctccaagatt atactttaca ggatttagtg 2100
aaggaagcag agaaagtgta tcacaagagg gagactgagg aagagaagca ggagagagaa 2160
aaaagagaga cggaagaaag ggagaaacgg cgtgaccgcc gccaagagaa gaatctgact 2220
aggattttgg ccgcagtagt aggtgaagaa agggtagaga aaagacagtt agggcacctg 2280
ggcaacaaag caaatagacc cgtgggcgga cagagaccac gacttgaaaa ggaccaatgt 2340
gcatactgca aagagaaagg acattgggcc agagaatgcc ccaaaaagaa acagaagggc 2400
cctaaggtac tggcccttga agaagattag gggagtcggg gctcggtccc cctccccgag 2460
cccagggtaa ctctctctgt ggaggggaac cccgttgact tcttagtgga cactggggct 2520
gaacactcgg tcttgactga accattagga caattaggat caagaaggac tctggtcaca 2580
ggagccactg gtagtaaact ttatccctgg acaacaaaaa gaagtttaaa aataggaaaa 2640
agccaagtga ctcactcttt ccttgtaatc cctgagtgcc ctgcaccgct tctgggcagg 2700
gacttgctga ctaaactaaa ggctcaggtc cagttcacct cgacagggcc ggaagtcacc 2760
tggggggaga cacctatagc atgtttagtc ctaaatctag aagaagaata tcgcctccat 2820
gaacccaaga ttgagaattt gccctccaag gaatggttgg tagcttttcc aggagtttgg 2880
gcagagcaag cgggaatggg actggctaag cgggtaccgc cagtggtggt cgaattaaaa 2940
gcagctgcta cccccatctc agtcaggcag taccccatga ctcaggaggc taaagaaggc 3000
attcgaccac acatccagag gctattacaa caaggtatac tgattcattg ccagtcccct 3060
ggaatactcc cctcttgccg gtacgtaagc ctggaactaa tgactatcga cctgtccagg 3120
acttgagaga ggtcaacaag cgggtactgg acatccaccc gacagtgccc aatccctaca 3180
atttgctaag ttccctgcca ccggagcggt cctggtacac tgttctggat ttaaaagatg 3240
ctttttttctg cctcagacta catccaagta gccaactcct gtttgccttc gaatggcggg 3300
accccgacgg aggacacacc ggtcagctga cctggaccag gcttccacag ggattcaaga 3360
actcgccaac tctcttcgat gaagcgctcc actgtgacct tgcgcccttc agggcacgaa 3420

-continued

```
acccccaaat ctctctctta cagtatgtag atgatttgct gcttgcagcc tcgacctggg   3480
aactgtgcct taatgggacc aaagagcttc taaaagaatt gggtgagttg gggtaccggg   3540
tgtccgcaaa aaaggcccaa ttatgctgtc cagaagttac ctacctggga tacaccctcc   3600
gagaagggaa gcggtggctc actgaagccc gaaagaaaac tgtgatgcag atcccgaccc   3660
ccaccactcc acgacaagta cgtgagtttc tgggaacggc gggcttttgt agactctgga   3720
taccaggatt cgccactttg gcggcccctt tgtaccctct gactaaagac aaagtcccat   3780
ttacatggaa agaagaacat cagaaagcct ttgaaaaaat aaagactgcc ctgctcacag   3840
cccctgcttt gactctgcca gacttgacca aaactttcac cttatacgtt gatgaacggg   3900
ctggaatagc tcggggagtc ctgactcagg ccctgggtcc ttggaagcgg ccggtggctt   3960
acttgtcaaa gaaactagac ccggtagcca gcggttggcc ctcttgtctg aaagccattg   4020
ccgcagtagc cttgcttgtc aaagatgctg acaagctgat cctgggtcaa catgtgacta   4080
taatcgcccc tcatgcctta gagagtattg tacggcagcc ccccgaccgc tggatgacaa   4140
actctcgaat gactcattac cagagcttgt tactaactga tcgaataact tttgctaccc   4200
ctgctatcct caaccctgcc accctactcc ctgaagcaga tgactctact cctgtgcatc   4260
gatgcgctga tatcctggcg gaggagactg gagtcagaac ggacctgact gatcaacctt   4320
ggccaggtgt gcctagctgg tatacggatg gcagcagctt cgtggtggaa ggaaaaagaa   4380
aagcaggagc agcggtggta gatgggaaac aggtgctgtg ggccagcagc ctcccagagg   4440
ggacgtctgc tcaaaaagcc gaacttttgg cactaattca agctctgcgc ctggcagaag   4500
gtaaggctgt caacatctat actgatagcc gctacgcctt tgctaccgcc cacattcatg   4560
gagctatcta taggcagagg gcctactcac atcggcaggg aaagacatta aaaacaaaga   4620
agaaatcctg gctcttctag aagccataca cctacccaag aaattggcca ttgtccattg   4680
tccaggacat caaaagggga ctgacccagt tacacgggga aaccagatgg cagatcagac   4740
agccaagcaa gctgcccatg gaactacggt gctaatagaa gaaatcagaa atcacccacc   4800
agagcccccg gagcacacac ataaaggctg tgccttgact gaagatgggc aaattgtctt   4860
accagctaaa gaagggcagg actatgtaaa aaggttacat caactaactc acctcggaac   4920
tgaaaaactt aaacaactaa ttaaaagttc caaatactgt gttcaagacc tacacaccac   4980
aacaaaacag gtagtggagg catgccaagc ctgtactatg accaatgcgg cccgaccgtt   5040
caaggagcct ggaaaaagaa tgaggggaga ccgaccagga gtctattggg aagtagactt   5100
tactgaagtt aagccaggaa aatatggtaa taaatatctt ctagttttta tagacacttt   5160
ttcaggatgg gtggaagcct ttcccacaaa atctgaaact gctcagatgg tgaccaagaa   5220
gatactagaa gaaattctgc ccagattcgg gattcccaag gtaatcgggt ctgataacgg   5280
cccagctttt gttgcccagg taagtcaaga attggccact caactgggga ttaattggaa   5340
attacattgt gcttacagac cccagagctc aggacaggta gaaaggatga atagaactct   5400
aaaagagacc cttactaaat tagctattga gaccggcggc aaggactggg tgaccctcct   5460
ccccttgca cttcttagag tccgaaactc gcccgggcgt ttcggcctca cccccttatga   5520
aatcctacat gggggaccgc ccccttaac ggagtcgtgc gggatattgg atcctagcac   5580
ttactccccc tcctcttctg ctttatttac tcacttaaag gccttagaag ttattaaaac   5640
acagatctgg agtcgaatta aagaagccta cgctccagga accatcacgg tgccccacgg   5700
gttccaggtc ggagactcag tcctggtcag acgacatcgc gctggcacgc ttgagccccg   5760
```

-continued

```
gtggaaggga ccctacctgg tgctgttgac tacccccctca gcagtcaagg tcgacgggat   5820
tgctgcctgg gtccatgctt cccatgtcaa gaagacaccc agtcagggca agaataacca   5880
tgaagaaaat tggacagtgg caaccagtga caatcctctt aagctgcgcc ttcgccgtag   5940
ccccaacctt gggtaataac ccccatgccc ccaaaaacta acctgggaag tgcttaacga   6000
agagggcgac gtcgtatggt caacaaccgc agtgcatccc ctttggactt ggtggcctga   6060
tcttgcaccc gatgtctgta agttagcagc cggctctatg gcttgggatc tttccagtta   6120
cactgactta gaaaagccac ccccagaaga acagtgtgtc cctcatggca tagggagcac   6180
attggggtgt tcaggacagt ttttccgagc caacctacag gcagcagact tctatgtctg   6240
ccccgggcag ggacaatcca gagaaatgaa gagacggtgc ggaggagctg cagactattt   6300
ttgtaataaa tggggatgtg agactacagg agaggcctac tggaaccctt cctcctcttg   6360
ggatctaatt atggttaaga agggtcgtaa gccagaagag ccagaaaaag gagaaagaga   6420
tccctccaaa tacccagctt ataggactgg gtgtgcctct ggaagctcgg atggccctca   6480
ggggccttgc aaaaacaatt attgtaaccc cttaaatatc agctttaccc cacagggaaa   6540
acaggatcgt caatgggtaa gaggaaatcg gtggggatgg agagtctata ctggcagcgg   6600
ggaccctgga ttcgtttttg tcattaagat aaaaatagaa agtccaccca cacgacccgt   6660
aggccccaat tcggtgcttg ataaccccat acccaggcct gagaggcctc ctcctcccac   6720
cctgtcacca aaggaaggct catattctct ctggactgca cccccacgtg tccctatggg   6780
gactgaggac cttctgttca atctgcttga tagtgcattt gttgttttaa atcgcactaa   6840
ccctgctgct actcagtcct gctggctgtg ttttacttcc aatccccctt actatgaagg   6900
aatagctcag ctacgtagct ataatgttac ttctgatcac tcacattgcc cctggggaag   6960
ccaacgaaag ttaaccctgt ctgcagtgtc aggaactgga ctgtgtatag gaaaagtacc   7020
taccaggcat cagcccctct gtaatgtaac tatctccaac ctgacaactg gcccagataa   7080
atacttagta ccccctctca atacctggtg ggcttgtggt accagcttga cccctgcctc   7140
catacttcac tttttgacaa tactaaagac ttttgtattt tagtccaatt ggtacctagg   7200
gtcatttatc atgatgatgc ctcgtttata gatgaatttg accaccgtgc tcgctacaag   7260
agagaaccta taaccttgac cttagctgtt ttgttaggac tcggagtggc ggcaggaatt   7320
ggaacaggag cagctgccct catccaacag ccctattact ataatgaact cagagcagct   7380
atggatgcgg acttgggagc cttagaacag tccataacca aactggaaga gtcattgact   7440
tcattatcag aggtagtatt acagaacagg aggggattag acctgctttt tctaaaagaa   7500
ggagggctct gtgctgccct aaaagaagaa tgttgctttt acgtagatca ttctggtgtc   7560
ataagagact ctatggcaaa gctcagagat agactagaaa ccagaaaaaa agaaagagaa   7620
acacaccagg gatggtatga aaattggttt aaccggtcac cctggttctc tacgctagtc   7680
tccactttgg tcgggccttt actcatattg ttgctaatcc tgacctttgg gccgtgcatc   7740
ctcaataaac tagtagcctt tgtaaaagaa agagtgagcg ctgtgcaggt aatggtccta   7800
agacaacaat atcaggtatt acaagaagct gagggatcgc tctaagatta gagcttttac   7860
aaaaagaaaa aggagggaat gaagagtaaa aacaaaactt tcaaagaaca ctagcccctg   7920
ccctagggcc ctcttctctg taggtaatca cacccggaac tttcttaaaa aaaaaaaaaa   7980
aaaagaaaag aaaagaaaaa acagttccca gaataactac ccgaggttct gatgacctct   8040
atggaatgtt tcaacgccct aagtgtgcct caggtgtatg attcatgtga cacatggttt   8100
atggtttaac tgaagaatac tgtatgactc tgatatttcc ccattctttt gtgggttttt   8160
```

tgcctttata agcctgttac aaattcagac cggggtcgaa ctcctctacc cctgtgtggt 8220
gtatgggttt cgaccccagc atgctggtct gagatctcgt tccgtttcac tctcaagaaa 8280
cttcctcgtg tgattgcagc aagtctggtc ttggtgccta ctgggtgcgc gcctttcccg 8340
aggcttgagt gaggggtctc ccttcgggg 8369

<210> SEQ ID NO 5
<211> LENGTH: 24
<212> TYPE: DNA
<213> ORGANISM: Cricetulus griseus
<220> FEATURE:
<221> NAME/KEY: misc_feature
<222> LOCATION: (2)..(24)
<223> OTHER INFORMATION: myristoylation target sequence 2 (Myr2), forward strand
<220> FEATURE:
<221> NAME/KEY: misc_feature
<222> LOCATION: (22)..(24)
<223> OTHER INFORMATION: Protospacer adjacent motif

<400> SEQUENCE: 5
gtcctaagcc tagaaactat gggg 24

<210> SEQ ID NO 6
<211> LENGTH: 24
<212> TYPE: DNA
<213> ORGANISM: Cricetulus griseus
<220> FEATURE:
<221> NAME/KEY: misc_feature
<222> LOCATION: (2)..(24)
<223> OTHER INFORMATION: myristoylation target sequence 4 (Myr4), reverse strand
<220> FEATURE:
<221> NAME/KEY: misc_feature
<222> LOCATION: (22)..(24)
<223> OTHER INFORMATION: Protospacer adjacent motif

<400> SEQUENCE: 6
gcatagtttc taggcttagg aggg 24

<210> SEQ ID NO 7
<211> LENGTH: 23
<212> TYPE: DNA
<213> ORGANISM: Cricetulus griseus
<220> FEATURE:
<221> NAME/KEY: misc_feature
<222> LOCATION: (1)..(23)
<223> OTHER INFORMATION: myristoylation target sequence 8 (Myr8), reverse strand
<220> FEATURE:
<221> NAME/KEY: misc_feature
<222> LOCATION: (21)..(23)
<223> OTHER INFORMATION: Protospacer adjacent motif

<400> SEQUENCE: 7
gagtgttagg gacaaaggag tgg 23

<210> SEQ ID NO 8
<211> LENGTH: 23
<212> TYPE: DNA
<213> ORGANISM: Cricetulus griseus
<220> FEATURE:
<221> NAME/KEY: misc_feature
<222> LOCATION: (1)..(23)
<223> OTHER INFORMATION: PPYP5 target, forward strand
<220> FEATURE:
<221> NAME/KEY: misc_feature
<222> LOCATION: (21)..(23)
<223> OTHER INFORMATION: Protospacer adjacent motif -continued

<400> SEQUENCE: 8
gttggttgat ctattaacgg agg 23

<210> SEQ ID NO 9
<211> LENGTH: 23
<212> TYPE: DNA
<213> ORGANISM: Cricetulus griseus
<220> FEATURE:
<221> NAME/KEY: misc_feature
<222> LOCATION: (1)..(23)
<223> OTHER INFORMATION: PPYP6 target, forward strand
<220> FEATURE:
<221> NAME/KEY: misc_feature
<222> LOCATION: (21)..(23)
<223> OTHER INFORMATION: Protospacer adjacent motif

<400> SEQUENCE: 9
gccactgccg cccccaccag agg 23

<210> SEQ ID NO 10
<211> LENGTH: 23
<212> TYPE: DNA
<213> ORGANISM: Cricetulus griseus
<220> FEATURE:
<221> NAME/KEY: misc_feature
<222> LOCATION: (1)..(23)
<223> OTHER INFORMATION: PPYP7 target, forward strand
<220> FEATURE:
<221> NAME/KEY: misc_feature
<222> LOCATION: (21)..(23)
<223> OTHER INFORMATION: Protospacer adjacent motif

<400> SEQUENCE: 10
gcccccacca gaggcagaag cgg 23

<210> SEQ ID NO 11
<211> LENGTH: 23
<212> TYPE: DNA
<213> ORGANISM: Cricetulus griseus
<220> FEATURE:
<221> NAME/KEY: misc_feature
<222> LOCATION: (1)..(23)
<223> OTHER INFORMATION: PPYP13 target, reverse strand
<220> FEATURE:
<221> NAME/KEY: misc_feature
<222> LOCATION: (21)..(23)
<223> OTHER INFORMATION: Protospacer adjacent motif

<400> SEQUENCE: 11
ggcagtggcg gatatggcgg ggg 23

<210> SEQ ID NO 12
<211> LENGTH: 23
<212> TYPE: DNA
<213> ORGANISM: Cricetulus griseus
<220> FEATURE:
<221> NAME/KEY: misc_feature
<222> LOCATION: (1)..(23)
<223> OTHER INFORMATION: PPYP20 target, reverse strand
<220> FEATURE:
<221> NAME/KEY: misc_feature
<222> LOCATION: (21)..(23)
<223> OTHER INFORMATION: Protospacer adjacent motif

<400> SEQUENCE: 12
gcttctgcct ctggtggggg cgg 23

<210> SEQ ID NO 13

<211> LENGTH: 1020
<212> TYPE: DNA
<213> ORGANISM: Cricetulus griseus
<220> FEATURE:
<221> NAME/KEY: misc_feature
<223> OTHER INFORMATION: Rad51

<400> SEQUENCE: 13
atggctatgc agatgcagct tgaagcaaat gcagatactt cagtggaaga agaaagcttt 60
ggtccacaac ctatttcacg gttagagcaa tgtggcataa gtgccaatga tgtgaagaaa 120
ttagaagaag ctggtttcca tacggtggag gctgttgctt atgcaccaaa gaaggaactc 180
ataaatatta agggaattag tgaagccaaa gcagacaaaa ttctggctga ggccgctaaa 240
ttagttccaa tgggtttcac cactgcaact gaatttcacc aaaggcgttc agaaatcata 300
cagattacta ctggctccaa agagcttgac aaactgcttc aaggtggaat tgagactgga 360
tctatcacag agatgtttgg agaattccga actgggaaga cacagatctg tcatacattg 420
gctgtaacat gccagcttcc cattgatcgt ggtggaggtg aaggaaaggc catgtacatt 480
gacaccgagg gtacgtttag gccagaacgg ctgctagcag tggctgagag gtatggtctg 540
tctggcagcg atgtcctaga taatgtagca tatgctcgag ggttcaacac agaccaccaa 600
acccagctcc tttatcaagc atcagccatg atggtagaat ccagatatgc actgcttatt 660
gtagacagtg ctactgccct ctacagaaca gactactcag gtcgaggaga gctttcagcc 720
aggcaaatgc atttggccag atttctgagg atgctgctgc gacttgctga tgagtttggt 780
gtagcagtgg taatcaccaa ccaggtagta gcccaagtgg atggagcagc catgttcact 840
gcagatccca aaaaacccat tggaggaaac atcattgccc atgcatcaac aaccaggctg 900
tacctgagga aaggaagagg ggagaccaga atctgcaaag tctatgactc tccctgtctc 960
cctgaagctg aagccatgtt tgccattaat gcagatggag taggagatgc caaggactga 1020

<210> SEQ ID NO 14
<211> LENGTH: 1053
<212> TYPE: DNA
<213> ORGANISM: Cricetulus griseus
<220> FEATURE:
<221> NAME/KEY: misc_feature
<223> OTHER INFORMATION: Rad51b

<400> SEQUENCE: 14
atgagcaaca agaaactaag acgagtaggt ttatcacaag agctgtgtga ccgtttgagc 60
agacatcaga ttgttaattg tcaggacttt ttaggtcttt ccccactgga acttatgaaa 120
gtgactggcc tgagttatgg aggtgtccag gagcttctgt atatggtcag cagggcctgt 180
gccccacaga tgcaaacagc ctatgatata aagatgcgga ggtctgctga actctcccca 240
gcgttcctgt ctactaccct ttctgctttg gacaaagccc tgcatggtgg tgtggcttgt 300
ggatcgctca cagagattac aggtccgcca ggttgtggga aaactcagtt ttgtataatg 360
atgagtgttt tagctacatt gcccaccaac atgggaggat tagaagggac tgtcgtgtat 420
attgacaccg agtctgcgtt tactgctgaa agactggtcg agattgcaga atcccgtttt 480
ccactctatt ttaacacaga agaaaaactg cttttgatga gcagtaaagt tcatcttcac 540
cgggaactca gctgtgaggc agttctgcaa aggcttgaat ctttggagga agagattatt 600
tccaaaggag ttaagcttgt gattgttgac tctattgctt ctgtggtcag aaaggagttc 660
gatcctcagc ttcagggcaa catcaaagaa aggaacaagt tcttggccaa acaagcatcc 720
ttgctgaagt acctggctga ggaattttca ctcccagtta tcttgacgaa tcaaattacg 780

```
acccatctga gtggagccct cccttctcaa gcagacctgg tgtctccggc tgatgatttg    840

tccctgtctg aaggcacttc tggatccagc tgtgtggtag ccgcactggg aaactcatgg    900

agtcactgtg tgaacacccg gctgattctc cagtaccttg actcagagag aaggcagatt    960

ctcattgcca agtcacctct ggctgccttc acctccttca tctataccat caagggggaa   1020

ggcctagttc ttcaaggcca agaaaggcca tag                                1053
```

<210> SEQ ID NO 15
<211> LENGTH: 1101
<212> TYPE: DNA
<213> ORGANISM: Cricetulus griseus
<220> FEATURE:
<221> NAME/KEY: misc_feature
<223> OTHER INFORMATION: Rad51c

<400> SEQUENCE: 15

```
atgcagcggg agctagtgag tttcccgctg tctcccacgg tgcgagtgaa gctggtggct     60

gcgggtttcc agacggccga ggacgtcctg ggggtgaagc cctctgagct cagcaaagaa    120

gttgggatat ctaaagagga agctttagaa actctacaaa ttgtaagaag agagagtctc    180

acagacaaac ccagatgtgc tggtgcatct gtggcaggca agaagtacac cgcactggaa    240

cttcttgagc aggagcacac ccagggcttc ataatcacct tctgctcagc gctagataac    300

attcttgggg gtggaatacc cctaatgaaa acaacggaag tttgtggtgt accaggtgtt    360

ggaaaaacac agttatgtat gcagttggca gtggatgtgc agattccaga gtgttttgga    420

ggagtggcag gtgaagcagt gtttattgat acggagggaa gttttatggt tgatagagtg    480

gtcacccttg caaatgcctg cattcagcac cttcacctta tagcaggaac acacaaggat    540

gaagaacacc agaaagcctt ggagggcttt actcttgaaa atattctttc tcatatttat    600

tatttccgtt gtcatgatta tactgagttg ctggcacaag tctatctcct tccagatttc    660

ctttcaaatc attcaaaggt gcagttagtg ataatagatg gcattgctct tccttttcga    720

catgaccttg atgatctatc ccttcgtact cgattactaa atggccttgc ccaacaaatg    780

atcagcctgg caaataatca cagattagct gttattttaa ctaatcagat gacaacaaag    840

attgataaaa atcaagcatt gcttgttcct gcattagggg aaagctgggg acatgctgct    900

acaataagac ttatttttca ctgggagcaa aagcaaaggt ttgcaacatt gtacaagtca    960

ccaagccaga aggagtccac aataccattt cagatcacac cacagggatt tagagatgct   1020

gctgtcactg cttcttcatc acagacagaa ggttcttcaa atctccggaa acggtcacga   1080

gaaccagagg aaggatgctg a                                             1101
```

<210> SEQ ID NO 16
<211> LENGTH: 1002
<212> TYPE: DNA
<213> ORGANISM: Cricetulus griseus
<220> FEATURE:
<221> NAME/KEY: misc_feature
<223> OTHER INFORMATION: Rad51d

<400> SEQUENCE: 16

```
aaacatgggc gtgctcaggg tggggctgtg cccgggcctc accgaagaga tcgtccagct     60

tctgaagggc caaaggatca agacagtggc ggacctggca gctgctaacc tggaggaggt    120

agcccagaag tgtggcttgt cctacaaggc cctggttgcc ctgaggaggg tattgctggc    180

gcagttctcg gctttcccat taaacggagc agacctatat gaggaactga agacttccac    240
```

```
tgccatcctg tccacaggca ttggaagcct ggacaaacta cttgatgctg gcctctatac    300

aggggaggtg actgaaattg taggaggtcc aggtagcgga aaaacccagg tgtgcctgtg    360

tgtggctgca aatgtggccc atagcctgca gcagaatgta ctgtatgttg attccagtgg    420

aggaatgaca gcatcccgcc tcctgcagct actacaggct agaacccaag atgaggagaa    480

acaggcaggt gctctccaga ggatacaggt ggtgcatgta tttgacatct tccagatgct    540

ggatatgcta caggaccttc ggggctccat ggcccagcag tcgacatctt cttcaggcac    600

tgtgaaggtt gtgattgtgg attctgtcac tgccgtgatt gccccacttc tgggaggtca    660

gcagagggaa ggcctggcct tgatgatgca gctggcccga gagctcaaga tcctggcccg    720

ggacctagct gtggcagtgg tggtgaccaa ccacttgacc cgagacaggg atggtaggag    780

gttcaaacct gctctgggac gctcctggag ctttgtgccc agtacccgga ttctcctgga    840

tgtcaccaaa ggggctggaa cattaggcag aggccaacgc acagtgtgtc tgaccaagtc    900

tccccgccag ccaacaggtc tacaggaggt gatagacatt gggacattgg ggactgagga    960

gcagagccca gaattgcctg ccaaacagac atgatgctgt tt                      1002
```

<210> SEQ ID NO 17
<211> LENGTH: 1257
<212> TYPE: DNA
<213> ORGANISM: Cricetulus griseus
<220> FEATURE:
<221> NAME/KEY: misc_feature
<223> OTHER INFORMATION: Rad52

<400> SEQUENCE: 17

```
atggctggag ctgaggaaac agtccgtgga ggctgtgaca cccatcctcc ctttgctggt     60

gggaaatctg tgctgtgctt tgggcagagc cagtacacag cagaggaata ccaggctatc    120

cagagggctc tgaggcagcg gctgggcccg gagtacatca gcagccgcat ggctggagga    180

ggccagaagg tgtgttatat tgaaggtcat cgagtaatta acctggccaa tgagatgttt    240

ggttacaatg gctgggcaca ctccatcacc cagcagaatg tggattttgt tgacttcaac    300

aatggcaaat tctacgtggg agtctgtgca tttgtaaggg tgcagttaaa ggatggttcc    360

tatcatgagg acgtgggtta tggagttagt gagggcctaa ggtcaaaggc cttgtcactg    420

gagaaggcca ggaaggaggc tgtgactgac gggctgaagc gggcactcag gagttttgga    480

aatgcacttg gaaactgcat tctggacaaa gactatctga ggtcactaaa taagcttcca    540

cgacagctcc ctcttgaagt ggatttaact aaagcaaaga gagaagattt tgaaccatct    600

gtggaacagg caagatataa tagctgccta cagaatgaag caccgggacc cccaaaacca    660

caagaagcgg cttccccttg cagaccaagc cacccacatg attcgaacat taggctgcag    720

ggggctaagg actgcagcag ctcctgcagt ctggccgccc ccatggagag tgatgccatt    780

caccagcgca agctccggaa gctccggcag aaacagctgc agcagcagtt ccggcagcag    840

atggaggccc acctacaggg ccacacacct gccgtaaaag tgaaagccga gcgtgaggca    900

gtgcttccag accttcctcc aaaacacagt acccctgtaa ctgctgcctc agaactcctc    960

agggagaaag ccatttttcc agataaccct gaagacaacc ttgaaatgtg ggacctgact   1020

ccggatttag aggacatcat taagcccttg tctagaccag aaccacctca aacctctgcc   1080

accagagtcc aggtgatcca ggatggtgtc ctacacggcc tttgccacca gatgccacca   1140

gaaaaacatg aagctggtca cctgcaggcc cacagcactc accagcatgt attaggaaac   1200

tctgactctc ataggaagag ccaggacctg aagaaaagga aactggatcc atcctga      1257
```

-continued

<210> SEQ ID NO 18
<211> LENGTH: 2235
<212> TYPE: DNA
<213> ORGANISM: Cricetulus griseus
<220> FEATURE:
<221> NAME/KEY: misc_feature
<223> OTHER INFORMATION: Rad54

<400> SEQUENCE: 18

```
atgaggagga gcttagctcc cagccagttg gccaggagga aaccagaagg cagatcatct     60
gatgatgaag actggcagcc tgggacagta actcctaaga aacaaaaatc cagtaatgag    120
acccagtgct tcctgtctcc ttttcggaaa cctttgactc agttaatcaa ccgaccgcct    180
tgtctggata gcagtcaaca tgaagcgttt attcgaagca ttttgtcaaa gcctttcaag    240
gtccccattc caaattatca aggtcctctg ggctgtcgag cattgggctt gaaaaaggct    300
ggtattcgtc gtgccctcca tgaccctctg gaagaaggtg ccttggttct gtatgagcct    360
cccccactaa gcgtccatga ccaactgaag ctggacaagg agaaactccc tgtccacgtg    420
gttgttgatc ctattctcag taaggtgttg cggcctcatc agagagaggg agtgaagttc    480
ctatgggagt gtgtcaccag tcgtcgaatc cctggaagcc atggctgtat catggctgat    540
gagatgggcc tgggaaagac actacagtgc atcacattga tgtggacact tttacgccag    600
agcccagagt gcaagccaga aattgagaaa gcagtggtag tgtcaccttc cagcttggtg    660
aagaactggt acaatgaggt tggaaagtgg cttggaggca ggatccaacc tctggccatc    720
gacggaggct ctaaggacga gatagaccga aaactggaag gattcatgaa ccagcgtgga    780
gcgagagtgc cttctcctat tctcatcatt tcctatgaga cttttcgcct tcatgtcgga    840
gtccttaaaa aaggaaatgt tggactggtc atatgtgatg agggacacag gcttaaaaac    900
tctgagaatc agacttacca ggccctggac agcttgaata ccagtcgtcg ggtgctcatc    960
tctgggaccc ccatccaaaa tgacttgctt gaatatttca gcttggtgca cttcgttaat   1020
tcaggcattt tgggaactgc ccaggagttc aagaagcatt ttgagctgcc aattttgagg   1080
agtcgagatg cagctgccag cgaggcagac aggcagctag ggaggaacg tcttcgagag    1140
ctcatcagta tagtgaatag gtgcctgata cggagaacat cagatatcct ctctaaatat   1200
ctgccagtga agattgagca ggtggtttgt tgtaggctga caccccttca aactgagtta   1260
tataagagat ttctgagaca ggctaagcct gaagaagaat tgcgtgaagg caagatgagc   1320
gtgtcttccc tgtcttctat cacctctcta aagaagctat gtaaccatcc agccctaatc   1380
tatgacaagt gtgtgtcagg ggaagatggc tttgaggata ctttggatat cttcccacct   1440
ggttatactt ctaaagctgt agaaccacag ctttcaggta aaatgctggt ccttgattac   1500
attctggcca tgactcgaag ccgcagcagt gataaagttg tgctggtgtc taattatact   1560
caaacgttgg atctctttga aaagctgtgc cgagctcgaa ggtacttgta tgttcgcctg   1620
gatggtacaa tgtccattaa gaagcgagcc aaggttgtgg agcgcttcaa tagtccatcg   1680
agtcccgatt ttgtcttcat gctgagcagc aaagctgggg gctgtggact taatctcatt   1740
ggtgctaacc ggctggtcat gtttgatcct gactggaacc cagccaatga tgaacaagct   1800
atggcccgag tctggcgtga tggtcaaaag aagacctgct atatttaccg actgctatct   1860
gctggaacca tagaagagaa gatctttcag cggcagagcc ataagaaggc actgagcagc   1920
tgtgtggttg atgaggagca agatgtagag agacatttct ctcttggcga gctcaaagag   1980
ctgtttaccc tggatgaagc tagcctcagc gacacacatg acaggctgca ttgccgccgt   2040
```

-continued

```
tgtgtaaaca gacgccaggt ctggccaccc cctgacggtt ctgactgtac ttcagatctg   2100

gctcagtgga accatagcac agataaacgg ggactccagg atgaggtact ccaggctgcc   2160

tgggatgctt cacctacagc catcaccttc gtcttccatc atcgttctca tgaggagcag   2220

cggggtctcc actga                                                    2235
```

<210> SEQ ID NO 19
<211> LENGTH: 837
<212> TYPE: DNA
<213> ORGANISM: Cricetulus griseus
<220> FEATURE:
<221> NAME/KEY: misc_feature
<223> OTHER INFORMATION: Xrcc2

<400> SEQUENCE: 19

```
atgtgcagcg actttcgtaa ggccgagtcc gggacggagc tccttgcccg gcttgaaggc     60

agaagctccc tgaaagaact agaacccaac ctgtttgctg atgaagattc accagtacat    120

ggtgatgttc ttgaatttca tggtccagaa ggaacaggaa aaacagaaat gctttatcat    180

ttaacagccc gatgtatact tccaaaatca gagggtggac tgcaaataga agtcttattt    240

attgacacag attaccactt tgacatgctc cggcttgtga cagtgctcga gcacagactg    300

tctcgaagct ccgaggagac catcaagctc tgcctgggaa gattgttcct ggcctactgc    360

agcagcagct tgcagctact gctcacgctg cactcactgg aagccctgtt ctgtagtcac    420

ccctctctct gccttctcat tgtggatagc ctgtcggctt tttactggac agaccgcgcc    480

agtggaggag agagtgtggc cctgcaggaa tccactctga agaagtgttc tcagctccta    540

gagaggcttg tcactgagta ccgcttggtg cttttcacaa caacacaaag tctaatgcag    600

aaagcctctg actcagcgga gcagcctgct tcctccaagc tcccaggtga cggagacaca    660

gactacagag cctatctctg caaggcctgg cagaaggtgg tgaagcacag agtcatcttc    720

tccagagagg acgaggctaa gagcagccgc ttctcattag tttcacgtca tttaaaaagt    780

aacagtttaa aaaaacatgc ttttatgatc agagaaagtg gggtggaatt ctgttga       837
```

<210> SEQ ID NO 20
<211> LENGTH: 1050
<212> TYPE: DNA
<213> ORGANISM: Cricetulus griseus
<220> FEATURE:
<221> NAME/KEY: misc_feature
<223> OTHER INFORMATION: Xrcc3

<400> SEQUENCE: 20

```
atggacttgg atcaactgga cctaaatccc agaattactg ctgcaattaa gaaggggaga     60

ctgaggtcag tgaaggaggt tctgtgctac tcgggaccag acctgcagag gctcaccagc    120

ctgtccaccc acgatgtgca gcacctactg agagtggccg ctctgcacct ccagggcagc    180

cgggtcctca cagcactgca gctgttccag cagagggaga gcttccccga gcagcatcaa    240

cgcctgagcc tgggctgccc ggtcttggat cagttcctgg gtggcggcct gcccctggag    300

ggcatcactg acctggctgg tcgaagctct gcagggaaga cccagctggg gctacagctc    360

tgcttgactg tgcagttccc acgacaatat ggaggcctgg aggctggggc tgtctacatc    420

tgcacagagg atgccttccc cagcaagcgg ctgtggcagc tcattgaaca gcaacagcag    480

ctgcggacgg atgttcctgg ggaggtgatc cagaagatca gattcagcaa ccacatcttc    540

atcgagcatg cggccgacgt ggacgccttg ctggagtgtg tgagcaagag ggttcccatt    600

ctgctgtcaa gggggatggc ccgcctggta gtggttgact ctgttgctgc cccattccgt    660
```

tgtgagtatg atgctcaggc cttggccacc agggccaagc acctgcagtc tctgggagcc 720
gcgctccgca gactgagcag taccttccgg agccctgtgc tgtgcatcaa ccaggtgatg 780
gaaacggtgg aggagcaaga gtctatgccc aggccactgg gggcctggga tgagcacctc 840
tctccagccc ttggcatcac ctgggccaac cagatcctga tgagactgat ggttgaccgg 900
gcacatgagg acgatgcctc catgggctta cccagaagcc cggcacggac catacgggtg 960
ctctctgccc cgcacctgcc cctctcctcc tgctgctaca cggtcagtgc ggaaggcatc 1020
agagggatac cgggaaccga gtcctgctaa 1050

<210> SEQ ID NO 21
<211> LENGTH: 5373
<212> TYPE: DNA
<213> ORGANISM: Cricetulus griseus
<220> FEATURE:
<221> NAME/KEY: misc_feature
<223> OTHER INFORMATION: Brca1

<400> SEQUENCE: 21
atggatttat ctgctgttca aatcgaagaa gtacaaaatg tccttcatgc tatgcagaaa 60
atcctggagt gtccaatctg tttggaattg atcaaagaac ccatttccac aaagtgtgac 120
cacatatttt gcaaattttg tatgctgaaa cttcttaacc agaagaaagg gccttcacaa 180
tgtcctttgt gtaagaatga gataaccaaa aggagcctgc aaggaagcac gaggtttagt 240
cagcttgttg aagagctgtt gaaaatcact gatgcttttg agcttgacac aggaatacag 300
tatgcaaacg gttacagtat ttcaaaattg aaaaattctt ctgaaccttt gaatgaggaa 360
gcttccatca tccagagtgt gggctaccga aaccgcggca aaagacttag acagattgaa 420
tctggaaatg ccaccttgaa ggacagtctc agtgtccagc tgtctaacct tggaattgtg 480
agatcaacaa agaaaaatca tcagacacag cctcgaaata aatctgtgta cattgaatta 540
gagtctgatt cttctgaaga gacagttagt aaaccagatg actgcagtgt gagagaccag 600
gaactgttac aaaccacctc tctgggagct ggagatgaag tcagtttgga ttcttcaacc 660
agagctgctt gtgagttttc tgaggacgta acaaatattg atctgcacca gtgcagtaat 720
aaagatttgg accccattga gaatcatgca actggaagat atccagaaaa atgtcaggat 780
atttctgttt caaacttaca tgtggagcca tgtggcacag atattcatgc cagctcgtta 840
cagcatgaga acagcagctt attactcact gaagacagaa tgaatgtaga aaaggctgag 900
ttctataata aaagcaaaca gtctggctta gccaggagcc aacagaacag atgggctgaa 960
agtaaagaaa catgtaatga taggcagatt cccagcactg agaaaaaggt agatccaaat 1020
actgattcct tctgtgggag aaaaaaatgg aaaaatcaga aaagtctgtg tcctgagaat 1080
tctagagcta cccaggatgt tccttggatg acactgaata gcagcattca gaaagtcaac 1140
gagtggtttt ccaaaactgg tgaaatgcta acttgtgatg gcacatctga caggaggcat 1200
gagtcaaatg ctggagcagc tgttgtgtta gaagtttcag atgaagtaga tggatgttcc 1260
agttcttcaa aagaaatgga cttagtggcc tctgatcccc ataatgcttt aaagtgtaaa 1320
agtgaaagcg acctctccaa accagtagag aacaatatcc gagataaaat atttgggaaa 1380
acgtatcaga gaaagggaag tctccctcac ttgaaccacg taactgaaat tataggcaca 1440
tttattgcag aaccacagat aacacaagaa cacccccttca caaataaatt aaaacgtaaa 1500
aggagaacta catgccttca tcctgaggat tttatcaaga aagcagattt aacagttact 1560
caaaagactt ctaaaaatgt aaatcaagga actgaccaaa tggagccaga tggcctagtg 1620

-continued

```
atgggtatta ccagtaatgg tcaagagaat gaaacacaag gtaataatct tcagaaagag   1680
aaaaatgcta atccagtgaa gtccttggaa aaggggtctg tttccacaac taaagccaaa   1740
actataagca acagtataag tgatttggag ctagaattaa atgtccacaa ttcacaggca   1800
cctaagaaaa gtcggctgag gaggaagtct tcaaccagat gtgttcttgc actggaacca   1860
gtcagtagga atccaagccc acctgcttgt actgaatttc aaattgatag ttgtagcagc   1920
agtgaagaaa cagagaaaaa caattccaac ccaacaccag tcaagaacat tagaaagcct   1980
caactcacgg aggacacaga acctgcagca gattccaaga agaataaaga gccaaatgaa   2040
caaagaagga agagaagggc cagtgatcct ttcccagaag agaaatttat gcctggctta   2100
ttaactaact gtccaagttc tagtaaacct caaggacctg ccaatcctag ccctcagaga   2160
aaggaagtag agaaacttga aacaagccaa atgtctgaca gtaccaaaga cctgagggat   2220
ctgttgctgg atggagaaca gggtttgccc actgagaggt cggaggagag taccagtgtt   2280
tcattggtgc ctgacactga ttatgacact cagaacagtg tgtcattgct ggaagctaat   2340
gctgtcagat atgcaaaaac agtatcaagc cagtgtatga cccagtttgt agcaagtgat   2400
aaccctaacg aactggtcca tggttctaaa gatgctggaa gtggcacaga gtgcttcaag   2460
catccattga gacacgaact tagccacatt caggagacca tagaaatgga agagagtgaa   2520
cttgatactc agtatttaca gaatacattt caagcttcaa agcgtcagtc atttacttta   2580
ttttcaaaac caagagatcc ccaagaggag tgtgtaacag cttgtgcttc ctctgtgtcc   2640
ttaagggaca tgagtccaaa agtgacttct gaaggtgaac aacaagaaga aagtcgggga   2700
cacgaagagg ctgaaatcag tcacatacag gcagggcctg cgacagtggg cgtgcctctg   2760
cctcgtcagg aaggtgatcc aggcgctgat acaatgcatg ctgcagtgtg cagcctttgt   2820
ccatcatctc agtacagaag caatgaaaac tcacatccta aacaatcagc ttctcccatc   2880
atgtcttcta taaaaactgg ccatgggaaa accctgtcag aggaacaatc tgagaaacat   2940
acattgtcaa atgaaaaggc aatgggaaat gagacctttg ttcaaagcac aatgcacaca   3000
attagccaaa accacagaaa aaatggttgt caagaagcca actcaggcag tattaatgaa   3060
gtgccttcca gtggtgaaaa cttccaagga cagctaggcc gaaacagaag gactaagtta   3120
aacactgtgc ttccactagg tcttatgcaa cctggagtct gtaagcatag ttttcctgtc   3180
agtgattata aatatcttga aataaaaaag caggaaggtg agaatgttgg tgcacacttc   3240
tcttcgtgtc tgttttcaga taagctcgaa caacctgtag ggagtggtaa tgtttttcag   3300
atttgttctg agacacctga tgacctgttg gatgatgttg aaatacagga aaatactagc   3360
tttggtgaag ttgacataat ggagaagtct gctgttttta acgggagtgt ccagagacga   3420
gagctcagta ggagccctag ccctttaacc catgcatcgc tggctcggaa tctccagaga   3480
cggtctagga agttagagtc ctcagaagac agcggatctt gtgaggatga agaccttccc   3540
tgcttccaac acttacttgg ccaagtaagc aaaacacctg aacctagcag tgttgtgaca   3600
cagcctctgt cagagaaagc agaggggacc caagtgccat ggaagagtag tgttggtgac   3660
tctgataacg aggtgatctt gatagaggca tctcaggaac atcaccctag tgaggatgca   3720
aaatactctg gcagcatgtt ctcttctcag cccagtgctg tacaaggttc aactgcaaat   3780
acaagctccc aggacccctt gtttaacctt tccaaacaaa agagtcacca gtctgaggat   3840
gaggaagatt ttctaagtga caaggaattg atttcagatg atgaggaaat gggaacttgc   3900
ctagaagaag ataatgatca agaagaggat attataatcc cagattcagc tgaagcggca   3960
```

-continued tctggatatg agagtgaaac aaacctttct gaagattgct cacagagtga tattttaacc 4020
actcagcaga gggccaccat gaaggataac ctgataaagc tccagcagga gatggcccac 4080
ctggaggctg tgctagaaca gcaaggggac cagccttctg tccactcctc gtctctcaca 4140
gctgaacctt gtgcccctga agacctacca aacgcagaac aaaacttatc aggaacagca 4200
attttaactt caaagaatat taatgaaaat cctgtaagcc ggaatccagc atgcgtttct 4260
gctgacaagt tccaaccaca acctccagac agttccagca gtgaaaataa agagtcaagg 4320
gaaggaaggc cttccctttt taaatctccg ttggcaggca gtaggtgctc tgcacacagc 4380
cgctctggga gtcttcaaaa cagaaactgc ccatctcaag aggagctcct ttggactgtt 4440
gaagcaggga agtcagaagg aacgccatac ctggaatctg gaatcagcct tttctctaat 4500
agagaccctg aatctgagtc ccctaaagag ccagcttatg tttgcaccac accagcttca 4560
acctctgcac ggacaatatc ccagtatcag gtttctgact ctttcgagag tccggctgct 4620
actcatgctc atactgcagt gatagaaact gtgagcaaga aaaagccaga attgacatct 4680
tcaaaaggaa gagccaataa aggaatatcc atggtggtgt caggcttgac ccccaaagaa 4740
gtaatgattg tgcaaaagtt tgctgaaaaa taccgcctca ctttaactga tgcaattact 4800
gaggagacta cccatgtcat tatgaaaaca gatgctgagc ttgtgtgtga acggacactg 4860
aaatattttc tgggaattgc aggaggaaaa tggatagtta gctattcatg ggtgattcag 4920
tctattcaag aaagaaaact tctgagtgtg catgaatttg aagtcagagg agatgttgtg 4980
actggaagaa accaccaagg tccaaagcga tccagagaat cccaggaaaa gctcttcaaa 5040
ggcctaacaa tctgttgttg tgagcccttc accaacatgc ccaaagatga gctggagaag 5100
atgctgcagc tgtgtggggc ttccgtggtg aaggagcttt cgtcactcac ccctgacacc 5160
ggtgttcatc caattgtgat tgtacagcca agtgcctgga cagaagagaa tggctgccct 5220
gagattgacc agctgtgtgg ggcgcacctg gtgatgtggg actgggtgtt ggacagtata 5280
tccgtctacc ggtgtcggga tctggacgcc tacctggtac agaatatcac ccatggccac 5340
gacagcagcg agccacagga ccccaatgat tag 5373

<210> SEQ ID NO 22
<211> LENGTH: 10098
<212> TYPE: DNA
<213> ORGANISM: Cricetulus griseus
<220> FEATURE:
<221> NAME/KEY: misc_feature
<223> OTHER INFORMATION: Brca2

<400> SEQUENCE: 22
atgtccaatg aatacaaaag gagaccaact ttttttgaaa tttttaaggc acgatgcagc 60
acagcagact taggacctat aagcctgaat tggtttgaag aactttcttc agaagcccca 120
ccatataatt ttgagcctcc agaagaatat gaatataaga ccaacaatta tgagccacag 180
ctgtttaaaa cgccacagag gaagctctct taccatctgt tggcttcaac tccaataata 240
ttcaatgaac aaggtcaaac tctaccagta gaccagtcgc ctttcaaaga actagggaag 300
actcttggaa atagtagaca taaaaatcac cacagaacca aggccaaaat ggactccatg 360
gttgatgttg ccagtccacc tctgaagtct tgtctcagtg aaagccctct tactctgcga 420
tgcacacagg ttgtaccaca aagagaaaag ccagtgatgt gtggaagttt attttctaca 480
ccaaaaatcg aggagggtca gacacctaaa cctatttctg aaagtctggg agttgaggtg 540
gatcctgata tgtcttggtc cagttcatta gctacaccac caacccttag ttccactgtg 600

-continued

```
ctcatagccc gagatgggga agcacgagga attgtgtttc ctgaagactc ccccgctgtt    660
ttgaaaagct acttttccag ccacaatgaa agtctgaaaa agagtggtat atcagttccc    720
tctgtgactg acagcgagaa caaaaaccag agggaagctt ttagtcatgg attggggaaa    780
acgttagagg attcatctgg caaaacaaac agcttcaaag attgccttag gcagtcaata    840
ccaaatgttc tagaagatgg ggagacagct gcagatactt ctgaagaaga tagtttctca    900
ttatgttttc ctaagcataa aaccagaaaa atgcaaaaaa tgagaatggg caagaccagg    960
aagaaaattt tcagtgaaat aagaactgat gaattaagtg aagaaactag aagtggagct   1020
gatggaaaac attcatttgc acttgaaatt gacccaagag atagtgatcc cttagatcca   1080
gatgtgacaa accagaaatg ctttgacaat gggaatgagg aaatctgcga ggaagttgta   1140
cagtcttcag acactcgatg gtctcagcta accctttctc gtctaactgg tacccagaag   1200
ggaaaaatac ctctacctcc tatttcttct tgtaaccaaa ataattcaga aaaagacttc   1260
atagatacga aggaagaagg tattgactct gttactttag aaaattcttt gcctcatatt   1320
tctagttttc cagaaccaga aaagatgttc tgtgagaaaa ctctggtaga taaggaacat   1380
gagggacagc atcttgaatc acatgagaac tccattgcag ggaagcaagt ggtatctgga   1440
acttgtcaag cagcttgcct attgagagag ccacttgaag agtctctggg taatctcttc   1500
tcagagagtg tgactagctc agcctttaca gaagaaccca gtgcctctgc aagtggattg   1560
ggaatatgtg ctgtgtcctc acagagagag gattctttgt gtcctagttc aggtgacact   1620
ggaaactggc catcaactct cactcacact tctgcaactg tgaacaatac aggtttaata   1680
tccagtctaa aaactaaaag aagaaagttt atttactctg tcggtgacag tgcatctcat   1740
caaggaaaaa tactacaggc agacagaaag tcagagctca ctaacacttc tgctcagttc   1800
gaaacaagtg cttttgaagc gccattcacg tttacaaatg ggaattcagg tttatcagat   1860
tcttctctcc aaagaagctg tttacagaat gatgctgaag agccatcttt gtccttatcc   1920
acctcatttg tgactgcttc caagaaagaa agtagttata gtaatgcatt gatatctcag   1980
gatctccatg acaaagaagc aatagtcagt gaagaaaaac tgcagccaca tacagccctg   2040
gaaactgatt gtctgtcgtg cttgccagaa agacaatgtg aatatgatcc aaagggtccc   2100
aaagtttcag atggaaaaga agaagtctta gtctcagcat gtcatcctgc aggacagcac   2160
acagcagcag cacagcccag cagcattagc tttgaattac aggaagaccc tgtcaatggc   2220
cacaatagta caagtcctaa agaaactcct agcttgaagg tgcttctgtc aaagccagtt   2280
gtgctttcta gaggaaaagt gtcatgtaaa atgccagaga aactgcagtg tgagagttat   2340
aaagataata ctgaattaag caaaagcatt cccttgggag gaaataaaat acacatccta   2400
agtgaaaatt ctaaacctcc tgagcttctg ccacctggaa aatatgtaac agaagcatcc   2460
cccacagtga agtctcagtt caatcagaat acaaatctag cagtcaaaaa aaatgaccaa   2520
gaagaaacgc cttttatttc agaagtaaca gtcaatgtga gttctggaga acttttccca   2580
gacaatgaga ataatttcgc ctttcaagta actcatgaaa ataataagac tgccttagga   2640
agtactgtgg aactgcagga agaagacctc cgccatgcta aagggcctaa tctcaacaac   2700
tctcccacag cagtagatgg agacataggt gatgagcaag cagctcatgc actgattatg   2760
gaagactccg attcctcagc tttagtccat gagtgtgcaa agaagagcag aaatactata   2820
gagcagcatc tgaaaggaac cacagacaaa gatttcaatt cctccttgga tgtgaaatca   2880
gatgggaaca atgactatac agacaaatgg ccaggatttt tggatccagt ttttaagcat   2940
aaatttggag gtagcttcag aacagcttcc aataaagaaa taaaactttc agaacataat   3000
```

```
gttaagaaaa gcaaaatgtt cttcaaagat attgaagagg agtatcctac tagtttaacc   3060
tgtattgaca tagttaatgc ctcaccatta gcaaaccagg agatactaag tggaccttat   3120
acatttgatt tgcagtcagt cactaccatg tctgcccatc cacagagtca ggcatctgtt   3180
tcttgtgaag atactcacac atcacttcag gtgttacctt caaagcaaga ttttcattcg   3240
aatcacaatt taacacccag ccaaaaggca gaaattacag aactttctac tatcttggaa   3300
gaatcaggaa gtcagtttga attcacacag ttcaaaaagc caagccatgt agcacagaat   3360
aatatacctg aagtgcctgg aaaacagacg gttgccataa atactacttc tgaggggtgg   3420
aaaaggattg gtcttcatct cacagtggat cctgcctctg tagctcagac agatgacagc   3480
aagaaatttg aaggttctgc tggatttaga caaagctttc cttgcctgtt gaaaagcagt   3540
tgtaacaaaa atacatctag tttttagca aatgtaaatg aaatggagtt tcgaggattt   3600
cgttctgctc ttggcacaaa gcttagtgtg tctagtgagg ctctgcaaaa agctgtgaaa   3660
ctcttcagtg acattgaaag tggtagtgag gagacttcca caaaagtcga cccaagagct   3720
ttgtcttcag gtgctcgtca tgattctggt gcttctgtgt ttaagataag gaaacaaaac   3780
agtggtaaaa gttttgatga gaaaactagt aagtgccaag taacattaca gaataatacc   3840
gaagtgacta ctggtatttt tgttgacaga aatcctgaaa attatgcaag aaatacaaaa   3900
tgtgaagata acaactctac tggttttcaa agaagtcctt ataaattaaa aaactcggag   3960
gatagtgaat caagtacaag cggcacagtt tctgttcatc aagatgatgg tgacttacca   4020
tgtgctgctg atcactgcag caagtaccct gagtcgtgtt cccaatatgt aagggaggaa   4080
aacacacaaa ttaaggaatg tgtatcagat ttaacatgtt tggaagtcat gaaagctgag   4140
gaaacatgct atattcaacc ttcagataaa gaacaattac cttcaggtaa gatggaacaa   4200
aatagaaaag attttaatat atcctttcag actgcaagtg ggaaaaatgt cagagtctct   4260
gaggagtcat taagtaaaag tatgaatatt ttaaatcaag taacagatga atcgatcatc   4320
tcttcagatt ctttgaattc taaatttcat tgtggcacaa ataacaacaa gatgggtatt   4380
tcacatcaca aggaaactac cagtactaaa aaggtatttg aagaacgttt cccagttggg   4440
actgtcagtc aattaccaac tctccagcag catcctagat gtgaaataga aagtatcaaa   4500
gaacctgctc tgttgggttt tcataccgct agtggaaaaa aagtcaaaat tatgcagaaa   4560
tctttagaca aagtgaaaaa cctttttgat gagacacagt atgttagtca tcaagggtca   4620
aaacccttga aggacagaga gaactgcaaa gaaggacttg cattaggatg tgagacaatt   4680
gaaatacctg cctccaagtg tgaagaaatg cagaagagct ttctctctaa ggagtctgaa   4740
gtgctatcta agcaaagtga tcgtttgtat aggtcgactg aaaatctcag aacatcaaat   4800
ggtacctctt ctaaagctaa tgtacatgga aacatagaaa gtgaaataga aaaaagtcct   4860
acaacttgct gcattagtca tttatcttat tcagtcactg aagattctgc tttgacatgt   4920
gacacaggac acggtagaaa aacttgtgtc agtgagtctt ctctatccaa agacagaaaa   4980
tggcttagag accgactggg tgataagctt caaaaaagag atgctgccga aattgaatgt   5040
gtaaaagaac atactgaggg ttatgctgga gatgcctcat gtgagcatag tttagacagt   5100
atcagaaatg aagttgatat aaattgtgtc tctgaaaatc aaacttcagc cctctttagt   5160
gaccctagca tgtgtcatag ctgtccatcc cattttggtt gtcattgtga taacaagcat   5220
aatgactcag gatatttctc aaaaaataaa atttattctg atactcagcc agacacgaag   5280
aatgaagaca ctgccaattt ttccagtgta tatgctacaa aagaagtaaa tatatacccg   5340
```

-continued

```
ccaactgtaa atgaagatat ttgtgttcag aaacttgaga ctaactcttc accacataca   5400

aataaaaatg tagccattga cttggctata gcagattcaa ggaattgtaa ggtatgccca   5460

tccaagttca ttacagatca ctcacaagaa actgtgaaaa cagtaaaagc aatatttaca   5520

cataacagtg ataaaacaat taagcaaaac acaaagagta aaccagatac ttgccggaca   5580

agctgtcaga aagcattgga taattcagag gattttatat gtcctagctc tttagaagat   5640

gactatatga actcacataa gacttctgtt tatacccacg atgaacaaat attacagcat   5700

aacctaagtg tgtctggact ggagaaagct caaataccac ctgttcactt ggaaacttgg   5760

gataagtgta aatctacaag ggaacttgca caggcagcct gttcttcaca catgccgggg   5820

atttttagca cagcaagtgg aaaagctgta caggtatcag acgcttcatt agaaaaggca   5880

aggcaagtgt tttctgagat ggatggtggt gctaaacagt tactttccac attgtctctg   5940

gaaagtcatg aacaatcaga ccactctggg agaagagaaa actctgtgac acataaccct   6000

gaggatgtat tgtcactccc aaaaaccttt gcaagcaatg ccaattcatc tgtattctct   6060

ggatttagta cagcaggtgg taaacgggtc acagtttcag aaagtgcctt acacaaagtt   6120

aagggaatgt tagaggaatt tgatttgatc ggaactgaac atactctcca gtgtccacct   6180

acatctgaag gtgtatcaaa aatacttcct caatattgtg ttgaaaagag aaccccagaa   6240

taccctataa actctaaatt gcagaaaacc tatgatgata aattcagttt accaaacaac   6300

tataaagaaa gtgcttcttt ggggaatact cattctcttg aagcttctcc ccaactctct   6360

cagtttaagc aagacacacg gttggtatta ggaaccaaag tatcccttct ggaaaaagaa   6420

caaaccttcc ctcaaaatat aaaaacagaa agtggtgtaa tggaaacttg tcctgatgtc   6480

cctgtgagaa caaatgtagg agactgttct gctttcgaca aaaagccaga gaactgtttt   6540

gaaacagaag cggtggagat tgccaaagct tttatggaag atgatgagct gacggattct   6600

gaaccaagtc acgacaaata ctcattgttt acctgccccc aaaatgaggc tttgttaaat   6660

ttgagaacta gaaagagaag aggaatggct gttgatgcag ttggacaacc cccaatcaaa   6720

agaagcttat taaatgagtt tgacaggata atagaaaata aaggaaaatc cttaaagcct   6780

tcaaaaaagtg ctccagatgg tacaataaaa gacagaagat tgttcacgca ccacatttct   6840

ctagagccag ttacctgtgg acccttctgc tctaccagag aaaggcaaga aatgcagagt   6900

ccacatttca ctgcacctgc tcaaggactt ctgtctaaag ggcatccttc tgtgcgttcg   6960

gctttggaaa aatcttcaag caattctaca gtttcagtcc agccgactca taaagtttct   7020

gctacaagga atgaaaggac aggatgctca gtcacaggca aatcccacaa agtcttcgtc   7080

ccacctttca aaatgaaatc acagtttcac agagataaac atttgaataa caagaatatt   7140

aattcagagg aaaagaacca aaagagcaga gatggagaca gtgaagatgt gaacgacggt   7200

gacattcgtc aatttaaaaa aggcagcttc catcaagagg ccgctagaat tgtcacagag   7260

tgtgaagaag agcctttaga tttaatgaca agccttcaga atgccagaga cctacagaat   7320

atacgaatta aaaagaaaga aaggcatcag ctctgtccac agccaggcag tctgtatctt   7380

accaagtcat ccactctgcc tcggatctct ctgcaggccg cagtaggagg ccggcttccc   7440

tctgcgtgtt ctcataagca gctctatatg tatggcgttt ctaaagagtg cataagcatt   7500

aacagcaaaa atgcggaata ttttcagttt gacattcagg attattttgg taaagaggac   7560

ctgtgtgctg gaaagggcat tcagctggct gatggtggat ggctgatccc ctccaatgaa   7620

gggaaggctg gaaaagaaga attctatagg gctctgtgtg acactccagg tgtggatcca   7680

aagcttattt ctagcctctg ggtctctaat cactaccggt ggattgtgtg gaaactggca   7740
```

-continued gctatggaat ttgcttttcc taaggaattt gctaacagat gcctaacccc agaaagagtg 7800
ctgcttcaac taaaatacag atacgatgtg gaaattgaca acagcagcag atcagcccta 7860
aagaagatcc tggaaaggga tgatactgct gcaaaaacac tcgttctctg tgtttctgac 7920
gtcatgtcac taagcacaac tggatcagaa acttcaggcg gcaaaactag tggtgcagat 7980
cccaagagca tagacacgat cgaactcaca gacggatggt atgctgtcaa ggcccagcta 8040
gaccctccac ttgtggctct tgtaaagagc aggagactga ctgtgggtca gaaaatcatt 8100
acccaagggg cagaactggt gggatctcct gatgcctgcg cacctctgga agcaccagac 8160
tctcttagac tgaagatttc tgccaacagc acacggcctg ctcgctggca cagcaaactg 8220
gggttctttc atgaccccag gcctttccct ctgcccttgt cctcactgtt cggtgatgga 8280
ggaagcgttg gctgtgtgga catcattgtt cagagagtgt accctttaca gtgggtggag 8340
aagacggcat caggattgta catattccgt aatgagagag aagaggagaa ggaagcagtg 8400
agatttgcag cggcccaaca gaagaaactg gaggccttgt tcaccaaaat ccaggcagag 8460
tttaaagacc atgaagaaga ctcagcgcag cggcgcgtgc tgtcccatgc actcacaagg 8520
cagcaggtct atgctctgca agatggtgca gagctctatg cagcggtgca gagtgcattg 8580
gatccagatc accttgaggg ttgtttcagt gaagagcagc tgagagcctt gaacaaacac 8640
agacaaatgt tgaatgataa gaagcaagca cagatccaat cagaattccg gaaggccgtg 8700
gagtccgctg agcaagagga gggcttatca agggatgttt caactgtgtg gaagcttcga 8760
gttacaagct acgagagaaa agaaaagtca gctctgctga gtatctggcg tccatcatca 8820
gacttacact ccctgttaac agaaggaaag agatacagaa tctatcatct ggcagtatca 8880
aaatctagga gtacatttga acgacctagc atccagttaa cagctacgaa aagaactcag 8940
tatcagcagc taccggctgc cagtgaaacc gtattccagg tttaccagcc gagggagccg 9000
cttgacttca gcagactgtt agagacagcc tttcagcctc cttgttctga agtggacctc 9060
gtaggagctg tagtttctgt tgtaagaaca acaggtcttg ctcctttggt ctacctatca 9120
gacgaatgcc ttaatttatt agtggtaaag tttgggatag accttaatga agacataaag 9180
ccacatgtgc taattgctgc aagcaacctc cagtggcacc cagaatccag atcaggagtg 9240
ccaacgttat ttgccgggaa tctttccata gtttctgcca gtccaaagga ggtctacttc 9300
cagaagcgag tcaacagaat gaggcaaact gttgagaata tcgatacatt ttacaaggag 9360
gcagaaaaga agcttttaca tctgcttaat ggaaacagtc ccaagtggtc caccccaaat 9420
aaagactcta ctcagccggc ctacacttgc cctgcttcag agctccttgc tacaggaggt 9480
cagctaatga ggttctcacc taatagtgag caaagttatc caagtccttt atcacattgc 9540
acaccaaaag aaaagtctac acccctggct cggtcagccc agatggcatc aaagtcttgt 9600
aacagggaga gagagactga tgaccgaaaa acctgcagaa aaagaagagc cttggatttt 9660
ctgagtcggc tgcccttacc tcccccggtc agtcccattt gtacctttgt ctctccggct 9720
gcacagaagg cttttcagcc gccacggagt tgtggcacca aatatgcaac acctatgaag 9780
aaaaaagaac ccagttcccc tcagaggagg acgccatttc agaaggacag tggcatttct 9840
cttctggaac aagattcggt agctgatgaa gaacttgcct tcctcaatac ccaagctctt 9900
gtacctggct caccagaaga aaatcaacaa gtacttcctg gtgactccac aagaacctct 9960
gtgccccaca acaaaagaac ccccagccag cacagaggcc agaccagcat gtaggacccc 10020
gatccaggaa ggggagtcta tctcagggat tacagaggtg gcaagggcag tgatggaaaa 10080
ttagctgtcg agtcttag 10098

<210> SEQ ID NO 23
<211> LENGTH: 888
<212> TYPE: DNA
<213> ORGANISM: Cricetulus griseus
<220> FEATURE:
<221> NAME/KEY: misc_feature
<223> OTHER INFORMATION: Cyclin D1

<400> SEQUENCE: 23
atggaacacc agctcctgtg ctgcgaagtg gagaccatcc gccgcgcgta ccctgacacc 60
aacctcctga acgaccgagt gctgcgagcc atgctcaaga ccgaggagac ctgcgcgccc 120
tccgtgtctt acttcaagtg cgtgcagagg gagattgtgc cgtccatgcg gaaaatcgtg 180
gccacctgga tgctggaggt ctgcgaggag cagaagtgcg aagaggaggt cttccctctg 240
gccatgaact acctggaccg tttcctgtct ctggagcccc taaaaaagag ccgcctgcag 300
ctgctagggg ccacctgcat gttcgtggcc tccaagatga aggagaccat tcctttgacc 360
gccgagaagt tgtgcatcta cactgacaac tctatccggc ccgaggagct gctgcaaatg 420
gaactccttc tggtgaacaa acttaagtgg aacctggccg ccatgactcc ccacgatttc 480
atcgaacact tcctctccaa aatgccagag gcggatgaga acaagcagat catccgcaag 540
catgcgcaga cctttgtggc cctctgtgcc acagacgtga agttcatttc caacccgccc 600
tccatggtgg ctgccgggag cgtggtggct gcaatgcaag gcctgaacct gggcagcccc 660
aacaactacc tgtcctgcta ccgcacaacg cactttcttt ccagagtaat caagtgtgac 720
ccggactgcc tccgcgcctg ccaggaacag attgaggccc ttctggagtc cagcctgcgc 780
caggcccagc agaacatcaa ccccaaggcc accgaggaag agggagaagc agagggagag 840
actgacctgg cctgcacacc caccgatgta cgagatgtgg acatctga 888

<210> SEQ ID NO 24
<211> LENGTH: 882
<212> TYPE: DNA
<213> ORGANISM: Cricetulus griseus
<220> FEATURE:
<221> NAME/KEY: misc_feature
<223> OTHER INFORMATION: Ercc1

<400> SEQUENCE: 24
atggaccttg ggaaagacga gggaagcctg ccgcagccca ccaggaagaa gtttgtgatc 60
ccactggaag acgaggcccc tcctgcaggg gccaagccct tattcagatc ctcacggaac 120
cccagcacca cggccccctc ggtcccagcg gcccctcaga cgtacgccga gtatgccatt 180
gcccagcctc caggaggggc tgggcccaca gggcccacag gctctgaacc tgtgaaggga 240
gagaaccccg gccagacggt gaaaacggga gcgaaatcca atagcatcct tgtgagcccc 300
cggcagaggg gcaaccctgt gttgaagttc gtgcgcaacg tgccctggga attcggcgag 360 gtgaccccctg actatgtgct gggacagagc acttgcgccc ttttcctcag cctccgctac 420
cacaatctcc atccagacta catccacgaa cggctgcaga gcctggggaa gagctttgcc 480
ctgcgtgtgc tgttggtcca agtggatgtg aaagatcctc agaaggccct gaaggacctg 540
gctaaaatgt gtatcttagc ggactgcacc ctggtcctgg cctggagtgc cgaggaagca 600
ggacggtacc tggagaccta caaggcatat gagcagaagc ccgctgacct cctcatggag 660
aagctggagc agaacttcct gtcccgggcc accgagtgtc tgaccaccgt gaagtcagtc 720
aacaaaaccg acagccagac cctcctggct acatttggat cccttgaaca gctcttgacg 780
gcatcacggg aggacctagc cttgtgcccc ggcctgggcc cccagaaggc ccgcaggctc 840
tttgacgtcc tccatgaacc cttcctcaaa gtgccccgat ga 882

<210> SEQ ID NO 25
<211> LENGTH: 4473
<212> TYPE: DNA
<213> ORGANISM: Cricetulus griseus
<220> FEATURE:
<221> NAME/KEY: misc_feature
<223> OTHER INFORMATION: MDC1

<400> SEQUENCE: 25
atggaaaaca cccaggttat tgactgggat gctgaagagg aggaggagac agaaataccc 60
agtgggtcct tggggtatag cttggagcct atagggcagc tgcgtctctt cagtagtact 120
catggaccag aaagagattt cccactctac cttggcaaga atgtaattgg ccgaagcccc 180
gactgctctg tggccctgcc ttttccatcc atctctaaac agcatgcagt aattgaaatc 240
tcagcttgca acaaagcccc tatcctccag gattgtggga gcctcaatgg cactcaactg 300
gtaaagcccc caaaggtcct aacccctgga gtgagccatc gtctgaagga ccaggaatta 360
attctgtttg cagactttcc ctgccagtac cgtcgcttgg atgtccctcc acctttggtc 420
tctcggggac ttctaactat agagaagacc cccagaatac agggagggtc ccaaacctcc 480
agagttttgt tggctgagga ttcggaggag gaagtagatt ttccttctgg aaggtatgtg 540
gcaaatggat caaggaatcc aacgtctcca tcagcaacag tagtaccaga aagtgatgaa 600
gaggggtctt ctccagccca aagtgtccgt gggccgtctt tgccctttga cttgggcagt 660
gacacagatg aagagctatg tccacagcca gcagttgggg agtcctcttc agttgccagg 720
gatggtgctg ctgcagaggc caagcagctg gaagctaatg gagtgacatc tggtatccag 780
ctggtactgg ctcagcctgc tgagcaaaag ctcagagatg caaaagtcaa gagtgaggct 840
ggcaatggag cggctgtggt tgggaggggc tccactgtgg gtaaggacag caacacggaa 900
atgggtgaag aacaccagcc ttccggcttt gtggacagcg atacagacgt ggaagaagac 960
aggatccctg tgaccccccc tgtagttccg gggaagaagc aagtcctgct tggagttggt 1020
aaaaaggacc ctggagcacc tgtcgtgacc catctgcagg acagcccagc tggtcgtggc 1080
acaggtgtgg aagaaggcaa gactccagtg gctggccctc cagagagaaa ccacacggcc 1140
atggtgatca gcagcgacac agatgaggaa gatggagtct cagcagcagt caccttggcc 1200
catctgaaag acagggggat ggctctgtgg agcagggagc caggcatgga agaggtcaag 1260
tcccaaccac aggtcctcgt agaacgaagc cagagtgcct ctgggaaaga cagtgacaca 1320
gacgtggagg aggaaaagag agaagtggtc cctgacagcc ccatggacac agatgaggct 1380
cttactgtcc cacattcaga gagccaagct ccccatagag ccagtgatga tgtagaccag 1440
ggtgtggata tgggctcccc tggtggtcag ctagagggaa accaggcctc ctctgccaca 1500
gtagaagaca gtagtgcaca agcagggaag gaagtcctgc ctcctgagga ggcctgggaa 1560
acagctgtgg aggaaggctc atcttcagca gcggcagatg taagacaaag caagcagcca 1620
ggagtagaag atgctgggac agagtgggct gcaactgttt gtgagcaggc gagcatgctt 1680
gaggtggggg tccaaggcag gtcacctgct acactggtag agccagtggt ggtgcctaca 1740
gctactctgg gggatcccac tcagccacag agagagggag cccagacccc cacaggaaag 1800
gagagaggag tacaaatggg caggaccaag aatgccaaag actgccgtga tgcagagtct 1860
gaagatgtgt gccttccggc tacccagtgc tttgtagaca gggagggcca gagctcagaa 1920
gctgtccaga gtttggaaga tgagcctacg caagtctttc catgcactct tccccaagag 1980
cctgggcctt cccacctcag cctgcagacg ccaggtccag gtgcccagga tgtgccttgg 2040
gaagtcttag ctacacagcc gttttgtctg agagaagctg aggcctctga actgcagctc 2100
atggacaccc accctgcagc tcatgaatcc cacccatctg tgtctagtgc atcagcagga 2160
cagcagcatc tggttcacac agagccgctg ggaattgaag gcggagagat gcaaactgtg 2220
gagaaagcca tgggccaatt gagttgcaag atggcatctg ctggagagga ctcaaggggt 2280
gatccagaac cctcggccca tcgcctgctt tctccagttc ctgaagcttc ttctccacct 2340
cagagtctgc tcacctctca gagccaaaag ccgtctacac cccagtctct gttacttacc 2400
tctccccctt ctgagctaca ccttcctgaa actcctcaca ccaagcctaa tgtcaggcct 2460
cggcggtcct ccaggatgac ctcctcccca cactcctctg ctgcccttaa gccctatact 2520
acctgcccca caaacctgcc tgctgcccct agaccaacat ctcgggctac tcggggcagg 2580
ggcagggcaa ataggtcctc taccaggacc ccggaaccag ttgtccctac agactctgag 2640
cttcaacctc ccacctccac agaacagtct gtcatcccca aacccacatc tccagtcact 2700
cagggcagca taaatggttc ctttgttaaa acgcctgaac cagttgttct cacaggtccc 2760
aaaatccagc ctcccacctc cacagaacag cctgttaccc caaaccccac acctcaggcc 2820
actcggggca ggccacatag gtcttccatc cagaccccag aaccacttac tcccactggt 2880
cctgacctcc agcctcccac ctccacagaa cagcctgtca tacctaaacc cacatctcgg 2940
gctgctcggg gcaggtcacg taagtcttct accaggaccc cagaaccagc tgtccccact 3000
ggtcctgacc tccagcctcc cacctccaca gaacagcctg tcacacctaa acccacatct 3060
cgggccactc ggggcaggtc acgtaagtct gtcagaaccc cagaaccagc tgtccccact 3120
ggtcctgacc tccagcttcc cacctccaca gctctgggca ctttgggaag ggcatgtaag 3180
tcctccattg aggattctga atcagttgga ccagtagcct ctgattttga acctcccatc 3240
tccacagacc ttgttgcccc tgaggtgaca ggtcagagca taacactaaa gtcttcacca 3300
ctaagtgctt ctccagtttc tgccacctct gaactccagc cacctgtccc cacagcccag 3360
cctgttctcc tggagcccat tcctcaagcc aaccaccgaa ggcggcggaa ggctgctggg 3420
aaacggggct cccacacagt tcccattggc caaaagcctt actctgcacc ctctgaacct 3480
ggttcccaat cttcaatcaa tcaaggcttg gcattggaag ccgctgagtc tattactgtt 3540
gctcctgagc ctgctgtttc ccaggctcca gagacctcca ctcagaatcc cgtggtgcaa 3600
aatgaagcag ctgggagatc agggctcatt cccaagcccc agcctgaggt ttctcgatcc 3660
cgcaagaagc cttctactac cacaacctca ccaattcaaa aacgtccccg aagacaaata 3720
ccccagaaga caatagtccc caaggaagaa gatcctgagg aaatgccagt gaaggaagag 3780
cctcaggaga tagcaattcc aacacccggc aaaagaaaga gggaccgtgt agaggatgag 3840
acccagggaa acccaagtcg gagccggcgg gctaaaccta accaagaagc agcagccccc 3900
aaggtactgt tcacaggagt tgtggattct cggggagagc gtgcagtcct ggctctgggt 3960
ggcagtctag ccagctcagt aaatgaggcc tcccacttgg tcactgatcg catccgaaga 4020
acggtcaagt tcttgtgtgc cctggggaag ggcatcccta tcctctccct gaactggctg 4080
tatcagtcca gaaaggctgg tcacttcctg ccacctgatg actacttggt gactgaccct 4140
gaacaagaga agaactttag cttcagcctt cgggactccc tgagccgggc tcggcaacaa 4200
aaactgctgg agggctatga gatttacgtg acccctggag tgcagccacc cccacctcag 4260

```
atgggcgaga tcatcagctg ctgtgggggc accaacctgc ccagcatgcc ccagtcctat   4320

aagccttacc gagttgtcat aacttgcact gaagacctac ctcgctgcgc tatcccatct   4380

cgactggggc tgcccctcct ctctcctgag ttcctcctga ctggagtgct aaagcaggaa   4440

gtcacaccag aggcctttgt cctttcaaat tag                                4473
```

<210> SEQ ID NO 26
<211> LENGTH: 2412
<212> TYPE: DNA
<213> ORGANISM: Cricetulus griseus
<220> FEATURE:
<221> NAME/KEY: misc_feature
<223> OTHER INFORMATION: Bard1

<400> SEQUENCE: 26

```
atgcaacttt ctgagtctgt ggttggacta ctaggtaggt acacaagccc tgctcgggaa     60

cgaaacccac gaggagcccc gccccttggc gttgagggcg tggccttggg ccgcgctcct    120

ctcagaaatt cgagcgcgct ctcattgcct ctcccctccc tcttacttgc tataaaggag    180

caacccagga tggtctgctg tctgcttcgg ctcatcatca tccagagtgt cgagttcttt    240

gaaatcatca ctaatattct gaaggagcca gtatgcttag gagggtgtga gcacatcttc    300

tgtagtgtgt gtataagtga ttgcgttgga tcaggatgtc ccgtgtgtta cacaccagcc    360

tggatcctag acctcaagat aaacagacaa ttggacaaca tgattcagct ttataggaag    420

cttcaaaatt tgctacatga caataaactt tcagatccaa aagacaacac atctaggaca    480

ggttcatttg atgatgcaga aagcaagaag aattcaataa aaatgtggtt tagtcctcga    540

agtaagaagg ttagatgtgt tgtgaataaa gtatcagtgc caacccagcc tcaaaagaca    600

aaagatgaca aagcccagga agcctccata tacgaatttg tttccacaag tcccccctgaa    660

gttgtttcta agagggctaa aacagcttct agaacatctg caaaaaagca gcagaagaaa    720

tctttagctg agatcaacaa gaaggggaat tcaaggccag aaacagaaga tagcaggttt    780

gattctaaag aggaactgaa agaggagagg gttgtctcct gtagccaaat accagttatg    840

gaaagtccac aggtaaatgg tgaaatagac ttgttagcta gtggttctgt tgcagaatct    900

gaatgttctg gaagattgac cgaagtttct ttaccattgg ctgagcatat agtatctcca    960

ggcactgtga gcaagagtga agagactcct gagaagaaag tctgtgtaaa agatcttctt   1020

tcagtagggc gtaatgaaaa tcacaaatac tgtagcaggc ctcctgatcc tacttctaag   1080

aattgtgaga gaagcattcc gagcaccagc agagatgtca ttaaaccaac agtgcttgca   1140

gaaaatatac tgttggttga ctgttcttca ctgccttcag accagcttca agttgatgtc   1200

acactcagga gaaagagtaa catatcagat aactccctta gcctttcacc aggcacaccc   1260

ccaccactgc tgaataattc aactcccaga caaatgatgt caaaaccctc catagtgaag   1320

ctgtcaccca gcattaccgc caggaaaaga aaccacagag gagagactct gcttcatatt   1380

gcttctatta agggcgatat accttctgtt gaatacctct tgcaaaacgg aaacgacccc   1440

aatgttaaag accatgctgg atggacacca ttgcatgaag cctgcagtca tgggcacctg   1500

aaggtagtgg aattgctgct ccagcataac gctttggtga ataccacagg ctatcagaat   1560

gacacaccac tgcacgatgc agtcaagaac ggccatgtgg atatagtcag ggtgttactg   1620

tccaatggcg cctccaggaa tgctgttaac atatttggtg tacggcctgt ggattataca   1680

gacaatgaaa atataagatc attattgctg ctaccagaga agagtgaatc atcctcaact   1740

agccagtgtg cagttgtgac tgctggacag cgaagaaatg ggcctctggt gcttataggc   1800
```

agtgggcttt cttcccaaca gcagaaaatg ctcagcaaac ttgagacagt tctcaaggct 1860
aaaagatgtg ctgagtttga cagtacagta actcatgtca ttgttcctga tgatgaagct 1920
caaagtactc tgaagtgtat gcttgggatt ctcaatgggt gttggatcct gaagtttgac 1980
tgggtgaaag cttgtttgca cagcaaagta cgtgaacagg aagaaaagta cgaagttcct 2040
ggaggtccgc agaagagcag gctcaacaga gagcagctgt tgccaaagct atttgatgga 2100
tgctacttct ttttgggggg aaacttcaaa catcatccaa agaatgatct ccttaagctc 2160
attactgcag caggaggcaa ggtgctcagt agaaagccca agccagacag tgacgtgact 2220
cagaccatca acactgttgc ataccatgcc aaccctgact ctgaccagcg cttctgtaca 2280
cagtacatcg tctatgaaga tctgtttaat tgtcgcccag aaagggttcg gcagggcaaa 2340
gtctggatgg ctccttccac ttggcttatc agctgtgtga tggcctttga attgcttcct 2400
cttgacagct ga 2412

<210> SEQ ID NO 27
<211> LENGTH: 2796
<212> TYPE: DNA
<213> ORGANISM: Cricetulus griseus
<220> FEATURE:
<221> NAME/KEY: misc_feature
<223> OTHER INFORMATION: Lig1 (Ligase 1)

<400> SEQUENCE: 27
atgagaaaaa aagaaccaga gaggaaaggg gagaactctg ctgccaccat gcagaaaagt 60
atcaggtcat ttttccaacc catgaaagag ggtaaagcac agaagccgga gaaggagaca 120
gctaacagca ccaaagagaa ggagccacct ccaaaggtgg cactgaagga gaggaatcga 180
gcagtgcctg agagtgattc tccagtgaag aggcctggaa ggaaggcagc ccaggtccta 240
agcagcgaag gggaggagga agatgaagcc cccagcaccc ctaaagtcca gaagtctgtg 300
tcagactcca aacaaagctc tcctcccagc cctgacgcat gtcctgagaa cagtcctttc 360
cacagtagcc cctccatgga gatctcccca tcaggattcc cgaagcgtcg cactgctcgg 420
aagcagctcc cgaaacggac aattgaggac actgtggagg agcagaatga ggacaaaggc 480
agagcagcca agaaaaggaa gaaggaagaa gaagcacaga ctccaatgga aagcctcaca 540
gagagtgaag atgtaaaacc caaggaagaa aaggaggagg gcaagcatgc tgaggcttcc 600
aagtcccctg agtcgggaac cttgacaaag acagagacca tcccagtgtg taaggccggc 660
gtgaaacaga agcctcagga agaggagcag agcaagcctc ctgccagagg cgccaagaca 720
ctcagcagct tcttcactcc ccggaagcca gcagagaaag ccatagtgaa acaagaagag 780
ccaggtactc cagggaagga agagaccaag ggagccctgg atccaacaaa ttacaatcct 840
tccaagagaa actaccaccc cattgaagat gcctgctgga aacatggcca gaaagtccct 900
tttctcgctg tggcccggac ctttgagaag attgaggagg tttctgctcg gctcaagatg 960
gtggagacac tgagcaactt gctgcgctcg gtggtggccc tgtcacctcc agacctgctt 1020
cctgttcttt acctcagcct caaccgcctt gggccacctc agcagggact agagctgggt 1080
gttggtgatg gtgtcctcct taaggcagtt gcccaggcca caggccgtca gctggagtcc 1140
atccgggctg aggtagctga gaagggtgac gtgggactgg tggccgagaa cagccgcagc 1200
actcagagac tcatgctgcc ccctcctccg ctcaccacct ccggggtctt taccaaattc 1260
tgtgacattg cccggctcac tggcagtgct tccatggcca agaagttgga tgtcatcaag 1320
ggcctgtttg ttgcctgccg tcactcggaa gcccggttca ttgccaggtc cctaagtgga 1380

```
cgcctgcgcc tcgggctggc tgagcagtcc gtcttggctg cccttgccct ggctgtgagc   1440

ctcacacccc ctggccaaga atttccccca gctgttgtgg atgctgggaa gggcaagacc   1500

acagaggcca gaaagacatg gttggaagaa caaggcatga tcttgaagca gaccttctgt   1560

gaggtacctg acctggaccg aatcatcccg gtgctgctgg aacatggcct ggaacgcctc   1620

ccagagcact gcaggctgag cccaggggtc cctcttaaac caatgctggc tcatcccact   1680

cggggtgtca gcgaggtact gaaacgcttt gaggaggtgg actttacctg cgagtacaaa   1740

tatgacgggc agcgggccca gattcatgtt ctggaaggtg gagaggtgaa gatcttcagt   1800

aggaaccagg aagacaacac aggaaagtac ccggacatca tcagccgcat ccccaagatt   1860

aaactcccct cggtcacctc ctttatcctg gacactgagg ctgtggcctg ggaccgggaa   1920

aagaagcaga tccagccatt ccaagtgctc accacacgca agcgcaagga ggttgacgcc   1980

tcggagatac aggtgcaggt gtgtctgtat gcctttgatc tcatctacct caacggagag   2040

tccctgattc gccagcccct gtctcgacgt cggcagctgc tccgggagaa ctttgtggag   2100

acagagggtg agtttgtctt cgccacctcc ctggacacca aggacatcga gcagatcgct   2160

gagttcttgg agcagtccgt gaaggactcc tgtgagggac tgatggtgaa gaccctggat   2220

gttgatgcca cctatgagat tgccaagagg tctcacaact ggctcaagct aaagaaggac   2280

taccttgacg gtgtgggcga cactctggac cttgtggtga ttggcgccta cctgggccgg   2340

gggaagcgtg ccggccggta tgggggcttc ctcttggctg cctatgatga ggagagtgaa   2400

gagctgcagg ccatatgcaa gctgggaact ggattcagtg atgaagagct ggaggagcat   2460

caccagagcc taaaggccct agtgttgccg accccacgcc cctatgtgag gatcgatggg   2520

gcagttgccc cagaccactg gctggaccca aaggtcgtat gggaggtgaa gtgtgcggat   2580

ctctccctgt cccctatcta ccctgctgcg cggggcctgg tggacaaaga gaaagggatc   2640

tcccttcgtt tccctcggtt cattcgtgtc cgtgaagaca agcagccaga gcaggccacc   2700

accagtgacc aggtggcctg tttgtaccgg aagcagagtc agatacagaa ccagcacaac   2760

tcagacttgg actccgactt tgaggactgc tattaa                             2796
```

<210> SEQ ID NO 28
<211> LENGTH: 2121
<212> TYPE: DNA
<213> ORGANISM: Cricetulus griseus
<220> FEATURE:
<221> NAME/KEY: misc_feature
<223> OTHER INFORMATION: Mre11

<400> SEQUENCE: 28

```
atgagccctg cagatccact tgatgatgaa gacactttta aaatcctggt tgccactgat     60

attcaccttg gatttatgga gaaagatgca gttcgaggaa atgatacatt tgtgacactt    120

aatgaaattt taaaacttgc cctggaaaat gaagtggatt ttattttgtt aggtggtgat    180

cttttccatg aaaacaagcc ctcaaggaaa actcttcata gttgcttgga gttgcttagg    240

aagtactgta tgggtgatcg ccctgtgcag tttgagatca tcagtgacca gtcagtcaac    300

tttggtttta gtaggtttcc atgggtgaac tatcaggatg gcaatctcaa catttccatt    360

ccagtgttta gtatccatgg caaccatgac gatcccacag gggcagatgc cctctgtgcc    420

ctggatattt taagctgtgc tgggtttgtg aatcactttg gacggtcaat gtctgtggag    480

aagattgaca ttagtccagt tctgctgcag aaaggaagca caaaacttgc tctgtacggc    540

ctagggtcca ttcctgatga aaggctctat cggatgtttg tcaataaaaa agtaacaatg    600
```

```
ctgagaccaa aggaagatga gaactcatgg tttaacttat ttgtgattca tcagaacagg    660

agtaaacatg gaagtaccaa cttcatccca gaacagtttt tggatgactt cattgacctc    720

gttatctggg gccatgaaca cgagtgtaaa attggcccaa ccaaaaatga gcagcagctc    780

ttctatgtgt ctcagcctgg aagctcagtg gtgacttctc tttcccctgg agaagctgtt    840

aagaaacacg tgggcttgct gcgcgttaaa gggaggaaga tgaacctgca gaagctgcct    900

ctccgcacag tgcggcagtt cttcatggag gatgtggttc tcgctaacca cccaaacctg    960

ttcaaccctg acaatcctaa ggtgacccag gccatccaga gcttctgctt ggagaagatt   1020

gaagaaatgc ttgaaaatgc cgagcgcgaa cggctaggga attctcttca accagagaag   1080

cctcttatcc gactacgggt ggactacagt ggaggctttg aacctttttag tgttcttcgc   1140

tttagccaga aatttgtgga tcgggtcgct aaccccaaag atatcatcca ctttttcagg   1200

catagggagc aaaagggaaa aacaggtgaa gagatcaact ttgggaagct tgtttcaaaa   1260

tctccttcgg aaggaacgac actcagagta gaagacctgg tgaagcagta tttccagact   1320

gcggagaaga atgttcagct ctcactgctg acagaaagag ggatgggtga agccgttcaa   1380

gaatttgtgg acaaggaaga aaaagatgcc atcgaggaat tagtgaagta ccagctggag   1440

aaaacacagc ggtttcttaa ggagcgccat atcgatgctc tggaagacaa gattgacgaa   1500

gaggtccggc gtttcagaga aagcagacag agaaatacca acgaagaaga cgatgaagtg   1560

cgagaggcca tgagcagggc ccgggcgctc agatcgcagt cagagaactc tgcctcagcc   1620

ttcagtgctg acgacctgag tttcgatata gcagaacaga cagcaaatga ctctgatgac   1680

agcctgtcag cagtgcccag cagaggccgg ggccgaggcc gaggtcgaag aggaggcaga   1740

gggcagagca ccgcatcaag aggaggatct cagagaggcc gagacactgg gcaggagacg   1800

gctactcgag gcagatgctc aaaggccact acatcgacct ctagaaatat gtccattcta   1860

gacgctttca gatctactcg acagcagcct tccagaaaca ctgccactaa aaattactca   1920

gagactattg aagtggatga atctgatgaa gatgacattt ttcctaccag ttccaaggct   1980

gatcaaaggt ggccaggcac aacatctagc aaacggatgt cccagagcca gatagccaag   2040

ggggttgact ttgaatcaga tgaggacgat gacgatgacc ctttcatgag cagtagttct   2100

ctaagaagcc gaagataata a                                             2121
```

<210> SEQ ID NO 29
<211> LENGTH: 5973
<212> TYPE: DNA
<213> ORGANISM: Cricetulus griseus
<220> FEATURE:
<221> NAME/KEY: misc_feature
<223> OTHER INFORMATION: 53BP1

<400> SEQUENCE: 29

```
atgccagggg agcagatgga ccctactgga agtcagttgg attcagattt ctctcagcaa     60

gatactcctt gcctgataat tgaagattct cagcctgaaa gccaggttct ggaagaagat    120

gcgggctctc acttcagtgt gctgtctcga caccttccca atctgcagat acacaaagag    180

aaccctgtgt tggatattgt gtccaatccg gaacaagcag ctgcagaaga gcaaggagac    240

aataatagct ccttcaatga acatctgaaa gagaacaaag ctgctgcaga tcctgtggat    300

tccactcatt tgggcacatg tgattccatc agtcaggtca tagaacagtt gcctcagcca    360

aacaggacaa gcagtgttct gggagtgaca gtggaagctg cttctcttcc agaagaggag    420

aaggaggaag agctggaaga ggagaatgaa gaggtgggag cagatgctgc tgatgccgct    480
```

-continued

```
ccgtgctccc ttggtgctga agattctgct tcatcacagt tgggctttgg ggttctggaa    540
ctgtcccaga gccaggatgt tgaagaacat acagtgccat atgatgtcaa ccaagaacat    600
atgcagttgg ttaccaccaa ctcgggttct tcccagctgt ctgacatgga tgcaaataat    660
gttaaatgtg aagaacagtc cactgaagat acctccatgg cagaacaacc taacaaagac    720
atccctgtta cagtcgagca cagtaaaggt atccctgtgg tagatgagca aaatctacca    780
ccggcaaggc cagaggatct gccttccagt cctcaagcct ctgctgcagc tgtggaaaca    840
aaggaagagg tacctgccca agagttgcca gaaggggcgc tggaggttca gatgtcctcg    900
gagcctgagg tctcgtccac tcaggaggac ttgtttgagc agagtagtaa aacagcttct    960
gatggttgtt ctactccttc aagggaggaa ggtgggtgtt ctccggtttc cacacccgcc   1020
accaccctgc aactcctgca gctgtctggt cagaggcccc ttgtccagga cagtctttcc   1080
acgaattcct cagatcttgt tgctccttcc cctgatgctt tccgacctac ccccttttatc   1140
gttcctagca gtcccacaga gcaaggaggg agaaaagttg agcccttgga tatgtcagtg   1200
atgcctgaag aaggaggggga gactttgcag aagcttcagg atgacgaagc agtggagata   1260
gaaaagcccc atctcccatc tcagccggct gtttccccac aagtgtcaac accagtgtct   1320
cagagcacac ctgtcttcac tccaggctct cttcccatcc cgtcccagcc tgaattttct   1380
catgacattt tcattccatc accaagtttg gaagaaccat caagtgatgg gaagaaaggt   1440
ggcgatttgc acagctcatc tttgactgtg gagtgttcta agacttcaga gagtgaacca   1500
aagaatttca ctgctgatct tgggctctcc ttgacagggg agtcttgcaa actgatgctt   1560
tcttcaagtg agtatagtca atcctcaaag atggagagct tggcttctcc caggagtgag   1620
ggagatggag agaataccca gattgaggac actgaaccgt tgtctccagt caccaattct   1680
aaacttcctg ctgaaagtga tgatgtcctg atgaatccag caccagatga ccaagtagaa   1740
atgaatcaga atgatgacaa agtaaaagag ggtgacacag agaacacagg tgaccatggt   1800
gttttagctg ctggtagtaa aggcagagaa gaaaccgttg ctgaagatgt ttgcattgat   1860
ctcacttgtg attctgggag tcaggcagtt ccgtctcccg ctactcggtc cgaggcactt   1920
tctagtgtct tagatcagga ggaagctatg gaaattaaag aacagcatcc agaggagggg   1980
ttttcgggat ctgaggtaga agaagtcccc gagactccct gtgaaagtca cagagaggag   2040
cccaaggaag aaacgatgga gagtatccca ctgcaccttt ctcttactga aacacagtcc   2100
caggcattgt gtcttcagaa ggaaatgccc aaagaagaat gcccagaggc catggaagtg   2160
gaaccctctg tgattagtgt tgactctccc cagaagctgc cggtactcga ccaggagtca   2220
gagcataagg agccagaggc ctgggaagaa gccgcgtcgg aggactcaag tgtggaggac   2280
tcaagtgtgg ttatcgttga tgtgaaggag ccctcgccaa gagttgtccc ctgcgaacct   2340
ttggagggag cagagaaatg ctcagattcc cactcctggg aggatgtggt gcccgaggtg   2400
gaaccgtgtg ctgcaaatag agtagacact ccggaggaaa agattgtaga atgtgacgga   2460
gatgtgaaag cagagaccac aagaaaggac tctgtagagg aagactcccc acagcctcct   2520
ttgccttcag tgaaagacga gcctcccaga gacgagcctc ccagacccga ccaggagatg   2580
cagcagtccc agcttcaaga gaaagagagc ccagtgacca tagatgcaaa agtggctgat   2640
gccaagcagc tggagtcaga gggagcatcc cagcagcttt cgaaagcccc tgcccgcgac   2700
tcacaaagtt tctgtgaaag ttctagtgaa accccatttc atttcacttt gcctaaagaa   2760
ggtgatatta tcccaccatt gactggtgca accccacctc acattgggca cctaaaattg   2820
gatcgcaaca gacatagtac tccaattggg attggcaact atccagaaag caccatagca   2880
```

-continued

```
accagtgatg tcatgtctga aagcatggtg gagatcaatg atcctctact tgggagtgaa   2940
aaaggagatt ctgagtctgc cccagaaatg gacggaaaac tgtatctgaa aatgaaactg   3000
gttagtcctg agacagaggc cagtgaagaa tctttgcagt ttagcctgga aaagcctgct   3060
actgctgaga gaaaaaatgg atcaactgct gttgctgagc ctgttgcaaa aaatggatca   3120
actgctgttg ctgagcctgt tgccagtccc cagaagaccg tgcctgtgtt tagctgcagg   3180
caagaggagg tttggagtga ggaccctccc tctgtaccca tcagggcaaa cttgctccat   3240
tttccaagtg ttgaagaaga ggacaaagaa aaactggatg gtaccccaaa gcttaggcag   3300
agtgaacagc ctgtgaggcc cgttgggctg gtcaaggatg ctgctacttc tgaggactct   3360
gcttcttctg ttccccagca gagagcaaca caggggtcat tcagccctca aggagaagtg   3420
atggaaacag acctgctaga aggactgagt gctaaccagg aaaaaccgtg taaggtcttg   3480
atggaaaggc ccacccagag taacatagga atccagacca tggaccattc cctgtgtgct   3540
ccagaaactg tttcagcagc aacccagact gtgaagagtg tatgtgaaca agggaccagt   3600
acagtggacc agaactctgg gaaacaagat gccactgtgc agaccgagag ggggggtgtc   3660
gagaaacagg cccctgtgga cgatacagaa tccctccaca gccagggaga agaagaattt   3720
gaaatgcccc agcctccaca tggccatgtc ttgcatcgtc acatgagaac catccgtgaa   3780
gtccggacac ttgtcacccg tgtcatcaca gatgtttact atgtggatgg gacagaagtg   3840
gaaaggaaag taactgagga gactgaagaa ccaattgtag aatgtcagga atgtgaaaca   3900
gaggtttccc cttcccagac tggaggctct tctggagacc tgggagacat cagttccttc   3960
tcctccaaag catccagctc acaccataca tcaagtggga caagtctctc agccatgcat   4020
agcagtggca gctcaggacg aggagccggg ccactcaaag ggaaaaccag cgggacagaa   4080
cctgcagatt ttgctttacc cagttcccga ggaggcccag gaaaactgag tcctagaaaa   4140
gggatcaatc agacaggggc accagtgtgt gaggaagatg gtgatgcagg ccttggcatc   4200
agacagggag ggaaggctcc tgtcacacct cgtggtcgtg gtcgaagggg ccgcccacct   4260
tctcggacca ctggaacaag agatgcagtt gtgtctggtc cgttgggcat agaagacatt   4320
tcacctagca tgtcaccaga tgacaagtcc ttcacccgaa ttgtgccccg tgtaccagac   4380
tctaccaaac gaattgatac cagttctact gttttgaggc ggagtgattc cccagagatt   4440
ccttttcagg ctgctactgg gtcttctgat ggcttggatg cctcatctcc aggaaatagc   4500
tttgtcgggc tccgtgttgt agccaagtgg tcatccaatg gctattttta ctctgggaaa   4560
atcacacggg atgttggagc tgggaagtat aagctgctct tcgatgatgg gtatgaatgt   4620
gatgtgctgg gcaaagacat tctcctgtgt gaccctatac ccctggacac tgaagtgaca   4680
gccctctcag aagatgagta tttcagtgca ggagtggtca aaggacacag aaaggagtct   4740
ggggagctgt actacagcat tgaaaaagaa ggccaaagga agtggtataa gcggatggca   4800
gtcatcctgt ccttggaaca aggaaacagg ttaagagagc aatatgggct tggcccatat   4860
gaagctgtta cacccctcac aaaggcagca gacatcagcc tagataattt ggtggaagga   4920
aagcggaaac gtcgcagtaa catcagctcc ccagccaccc ccactgcctc cagcagcagc   4980
agcagcagca gcacaacacc cacccgtaaa accacagaga gtccccgtgc ttccacggga   5040
gttccatcag gcaaaaggaa actcatcact tctgaagagg aacggtcccc agctaagcga   5100
ggccgcaagt ctgtcaccgt gaaacctggt acagtggggg caggagaatt tgtgagcccc   5160
tgcgagagtg gagacaacac aggtgaacct tctgtcctgg aagagccaag agggcctttg   5220
```

-continued

```
ccccctcaaca agaccttgtt tctgggctat gcctttctcc ttaccatggc cacaaccaat   5280

gacaagctgg ccagccgctc taaactgcta gatggtccta caggaagcag tgaagaagag   5340

gaggaatttt tagaaattcc tcctttcaac aagcagtata cagaatgcca gcttcgagca   5400

ggagctgggt atatccttga agacttcaat gaagcccagt gtaacacagc ctaccagtgt   5460

ctcctaattg ctgatcagca ttgtcgaacc cggaagtact tcctgtgcct tgccagtgga   5520

attccttgtg tgtctcatgt ctgggtccat gacagctgcc atgccaacca gctccaaaac   5580

taccgtaatt atctgctgcc tgctgggtat agccttgagg agcagcgaat tctggattgg   5640

caacctcgtg aaaacccttt ccagaatctg aaggtactct tggtgtcaga tcaacaacag   5700

aacttcctgg agctctggtc tgagatcctc atgactggag gggcagcctc tgtgaagcag   5760

caccattcaa gtgcccataa caaagacatt gctttagggg tatttgatgt ggtggtgaca   5820

gacccctcat gcccagcctc ggtgctcaag tgtgctgaag ccttgcagct gcctgtggtg   5880

tcacaagagt gggtgatcca gtgcctcatt gttggggaga gaattggatt caagcagcat   5940

ccaaaatata aacatgatta tgtttctcac taa                                5973


<210> SEQ ID NO 30
<211> LENGTH: 47
<212> TYPE: DNA
<213> ORGANISM: Cricetulus griseus
<220> FEATURE:
<221> NAME/KEY: ERV group 1 consensus sequence
<222> LOCATION: (1)..(47)

<400> SEQUENCE: 30

gcccccgcca tatccgccac tgccgccccc accagaggca gaagcgg                   47


<210> SEQ ID NO 31
<211> LENGTH: 47
<212> TYPE: DNA
<213> ORGANISM: Cricetulus griseus
<220> FEATURE:
<221> NAME/KEY: Group 1 PPYP motif sequence
<222> LOCATION: (1)..(47)

<400> SEQUENCE: 31

gcccccgcca tatccgccac tgccgccccc accagaggca gaagcgg                   47


<210> SEQ ID NO 32
<211> LENGTH: 37
<212> TYPE: DNA
<213> ORGANISM: Cricetulus griseus
<220> FEATURE:
<221> NAME/KEY: PPYP motif sequence with out-of-frame deletions via
      PPYP7 sgRNA
<222> LOCATION: (1)..(36)

<400> SEQUENCE: 32

gcccccgcca tatccgcccc accagaggca gaagcgg                              37
```